(12) United States Patent
Horn

(10) Patent No.: US 12,128,036 B2
(45) Date of Patent: Oct. 29, 2024

(54) COMPOSITIONS AND METHODS FOR STORAGE STABLE OPHTHALMIC DRUGS

(71) Applicant: Lenz Therapeutics Operations, Inc., Solana Beach, CA (US)

(72) Inventor: Gerald Horn, Highland Park, IL (US)

(73) Assignee: LENZ THERAPEUTICS OPERATIONS, INC., Solana Beach, CA (US)

( * ) Notice: Subject to any disclaimer, the term of this patent is extended or adjusted under 35 U.S.C. 154(b) by 0 days.

(21) Appl. No.: 18/239,087

(22) Filed: Aug. 28, 2023

(65) Prior Publication Data
US 2023/0414587 A1 Dec. 28, 2023

Related U.S. Application Data

(63) Continuation of application No. 17/242,398, filed on Apr. 28, 2021, now abandoned, which is a continuation-in-part of application No. 17/069,155, filed on Oct. 13, 2020, now Pat. No. 11,273,150, which is a continuation-in-part of application No. 16/595,789, filed on Oct. 8, 2019, now Pat. No. 10,836,760.

(60) Provisional application No. 62/743,720, filed on Oct. 10, 2018.

(51) Int. Cl.
| *A61K 31/439* | (2006.01) |
| *A61K 47/02* | (2006.01) |
| *A61K 47/12* | (2006.01) |
| *A61K 47/14* | (2017.01) |
| *A61K 47/18* | (2017.01) |
| *A61K 47/20* | (2006.01) |
| *A61K 47/22* | (2006.01) |
| *A61K 47/26* | (2006.01) |
| *A61K 47/38* | (2006.01) |
| *A61J 1/16* | (2023.01) |

(52) U.S. Cl.
CPC ............ *A61K 31/439* (2013.01); *A61K 47/02* (2013.01); *A61K 47/12* (2013.01); *A61K 47/14* (2013.01); *A61K 47/183* (2013.01); *A61K 47/186* (2013.01); *A61K 47/20* (2013.01); *A61K 47/22* (2013.01); *A61K 47/26* (2013.01); *A61K 47/38* (2013.01); *A61J 1/165* (2013.01)

(58) Field of Classification Search
CPC .................................................. A61K 31/439
USPC ......................................................... 514/290
See application file for complete search history.

(56) References Cited

U.S. PATENT DOCUMENTS

| 4,474,751 A | 10/1984 | Haslam et al. |
| 4,906,467 A | 3/1990 | Schwartzman et al. |
| 5,073,560 A | 12/1991 | Wu et al. |
| 5,286,864 A | 2/1994 | Walther et al. |
| 5,451,587 A | 9/1995 | Walther et al. |
| 5,488,050 A | 1/1996 | Neufeld |
| 6,120,758 A | 9/2000 | Siddiqui et al. |
| 6,241,124 B1 | 6/2001 | Hoyt |
| 6,291,466 B1 | 9/2001 | Gwon et al. |
| 6,353,022 B1 | 3/2002 | Schneider et al. |
| 6,410,544 B1 | 6/2002 | Gwon et al. |
| 7,067,261 B2 | 6/2006 | Bencherif et al. |
| 8,299,079 B2 | 10/2012 | Kaufman |
| 8,455,494 B2 | 6/2013 | Kaufman |
| 8,501,800 B2 | 8/2013 | Bowman et al. |
| 8,524,758 B2 | 9/2013 | Benozzi |
| 9,089,562 B2 | 7/2015 | Horn et al. |
| 9,314,427 B2 | 4/2016 | Horn et al. |
| 9,320,709 B2 | 4/2016 | Horn et al. |
| 9,833,441 B2 | 12/2017 | Horn et al. |
| 9,844,537 B2 | 12/2017 | Horn et al. |
| 9,968,594 B2 | 5/2018 | Horn et al. |
| 10,052,313 B2 | 8/2018 | Horn et al. |
| 10,064,818 B2 | 9/2018 | Horn et al. |
| 10,307,408 B2 | 6/2019 | Horn et al. |
| 10,319,154 B1 | 6/2019 | Chakravarthula et al. |
| 10,520,730 B2 | 12/2019 | Bouchier et al. |
| 10,617,763 B2 | 4/2020 | Horn et al. |
| 10,775,628 B2 | 9/2020 | Samec et al. |
| 10,836,760 B2 | 11/2020 | Horn |
| 10,959,990 B2 | 3/2021 | Horn |
| 11,179,327 B2 | 11/2021 | Horn et al. |

(Continued)

FOREIGN PATENT DOCUMENTS

| CN | 101262886 A | 9/2008 |
| CN | 101616640 A | 12/2009 |

(Continued)

OTHER PUBLICATIONS

Barot et al. Prodrug Strategies. Ocular Drug Delivery Med. Chem. 8(4):753-768 (2012).

(Continued)

*Primary Examiner* — Taofiq A Solola
(74) *Attorney, Agent, or Firm* — WILSON SONSINI GOODRICH & ROSATI

(57) ABSTRACT

The present invention is related to methods of stabilizing an ophthalmic drug by adding a surfactant and a viscosity enhancer to the ophthalmic drug to create a composition wherein the composition has a viscosity of about 25 centipoise or less at a shear rate of 1/1000 per second at 25 degrees Celsius and a viscosity of about 70 centipoise or more at shear rate of 1 per second at 25 degrees Celsius, filling the composition into a container; and storing the container at a temperature from about 2 degrees Celsius to about 25 degrees Celsius. The present invention is further directed to a container prepared by the methods of the present invention.

20 Claims, 4 Drawing Sheets

(56) References Cited

U.S. PATENT DOCUMENTS

| | | |
|---|---|---|
| 11,179,328 B2 | 11/2021 | Horn |
| 11,214,569 B2 | 1/2022 | Horn |
| 11,273,150 B2 | 3/2022 | Horn |
| 11,344,538 B2 | 5/2022 | Horn |
| 11,648,247 B1 | 5/2023 | Horn |
| 2002/0035264 A1 | 3/2002 | Kararli et al. |
| 2002/0036264 A1 | 3/2002 | Nakasuji et al. |
| 2003/0104996 A1 | 6/2003 | Li et al. |
| 2003/0140996 A1 | 7/2003 | Thomson |
| 2003/0165545 A1 | 9/2003 | Huth et al. |
| 2003/0232089 A1 | 12/2003 | Singh et al. |
| 2004/0106644 A1 | 6/2004 | Randazzo |
| 2004/0142829 A1 | 7/2004 | Tsao et al. |
| 2005/0196370 A1 | 9/2005 | Yu et al. |
| 2006/0172972 A1 | 8/2006 | Bhushan et al. |
| 2006/0177430 A1 | 8/2006 | Bhushan et al. |
| 2007/0297990 A1 | 12/2007 | Shah et al. |
| 2009/0074786 A1 | 3/2009 | Dor et al. |
| 2009/0156581 A1 | 6/2009 | Dillon et al. |
| 2009/0297565 A1 | 12/2009 | Müller et al. |
| 2009/0297566 A1 | 12/2009 | Brinkman et al. |
| 2010/0016395 A1 | 1/2010 | Benozzi |
| 2010/0310476 A1 | 12/2010 | Tamarkin et al. |
| 2011/0172302 A1 | 7/2011 | Dalton et al. |
| 2011/0250294 A1 | 10/2011 | Tien et al. |
| 2011/0251285 A1 | 10/2011 | Tien et al. |
| 2012/0028910 A1 | 2/2012 | Combal et al. |
| 2012/0094962 A1 | 4/2012 | Skulachev |
| 2012/0165295 A1 | 6/2012 | Painter et al. |
| 2012/0315265 A1 | 12/2012 | Lai et al. |
| 2013/0245030 A1 | 9/2013 | Kaufman |
| 2014/0113946 A1 | 4/2014 | Abad |
| 2014/0200211 A1 | 7/2014 | Abad |
| 2014/0221446 A1 | 8/2014 | Meyer |
| 2014/0378401 A1 | 12/2014 | Horn |
| 2015/0010634 A1 | 1/2015 | Knappe et al. |
| 2015/0065511 A1 | 3/2015 | Horn et al. |
| 2015/0290125 A1 | 10/2015 | Horn et al. |
| 2015/0290126 A1 | 10/2015 | Horn et al. |
| 2015/0290216 A1 | 10/2015 | Khopade et al. |
| 2016/0008278 A1 | 1/2016 | Horn et al. |
| 2016/0008337 A1 | 1/2016 | Horn et al. |
| 2016/0018671 A1 | 1/2016 | Waite et al. |
| 2016/0193193 A1 | 7/2016 | Horn et al. |
| 2016/0193194 A1 | 7/2016 | Horn et al. |
| 2016/0346259 A1 | 12/2016 | Horn et al. |
| 2016/0354315 A1 | 12/2016 | Li |
| 2018/0140708 A1 | 5/2018 | Horn et al. |
| 2018/0228729 A1 | 8/2018 | Lee et al. |
| 2018/0235946 A1 | 8/2018 | Horn et al. |
| 2018/0280363 A1 | 10/2018 | Horn et al. |
| 2019/0000755 A1 | 1/2019 | Horn et al. |
| 2019/0038609 A1 | 2/2019 | Horn |
| 2019/0240152 A1 | 8/2019 | Horn et al. |
| 2019/0321337 A1 | 10/2019 | Robinson et al. |
| 2020/0115377 A1 | 4/2020 | Horn |
| 2020/0146976 A1 | 5/2020 | Horn |
| 2020/0181136 A1 | 6/2020 | Horn |
| 2020/0186839 A1 | 6/2020 | Horn |
| 2020/0246310 A1 | 8/2020 | Pitlick et al. |
| 2020/0281906 A1 | 9/2020 | Horn |
| 2020/0308168 A1 | 10/2020 | Banerjee et al. |
| 2021/0038574 A1 | 2/2021 | Horn |
| 2021/0251970 A1 | 8/2021 | Horn |
| 2022/0031608 A1 | 2/2022 | Horn |
| 2022/0105090 A1 | 4/2022 | Horn |
| 2022/0233434 A1 | 7/2022 | Horn |
| 2022/0347170 A1 | 11/2022 | Horn |
| 2023/0151000 A1 | 5/2023 | Horn |
| 2023/0190738 A1 | 6/2023 | Horn |
| 2023/0190739 A1 | 6/2023 | Horn |
| 2023/0248644 A1 | 8/2023 | Horn |
| 2023/0310392 A1 | 10/2023 | Horn |
| 2023/0398064 A1 | 12/2023 | Horn |
| 2023/0398113 A1 | 12/2023 | Horn |
| 2023/0404912 A1 | 12/2023 | Horn |
| 2023/0414494 A1 | 12/2023 | Horn |
| 2024/0091207 A1 | 3/2024 | Horn |

FOREIGN PATENT DOCUMENTS

| | | |
|---|---|---|
| EP | 0197718 A2 | 10/1986 |
| JP | S62194861 A | 8/1987 |
| JP | H06211666 A | 8/1994 |
| JP | H07330604 A | 12/1995 |
| JP | 2852607 B2 | 2/1999 |
| JP | H11292151 A | 10/1999 |
| JP | 2002521429 A | 7/2002 |
| JP | 2004168709 A | 6/2004 |
| JP | 2008536866 A | 9/2008 |
| JP | 2010514517 A | 5/2010 |
| JP | 2012508793 A | 4/2012 |
| WO | WO-9612711 A1 | 5/1996 |
| WO | WO-0006135 A2 | 2/2000 |
| WO | WO-02080915 A2 | 10/2002 |
| WO | WO-02100437 A2 | 12/2002 |
| WO | WO-2007011874 A2 | 1/2007 |
| WO | WO-2008083118 A1 | 7/2008 |
| WO | WO-2009015286 A2 | 1/2009 |
| WO | WO-2009077736 A2 | 6/2009 |
| WO | WO-2010070664 A1 | 6/2010 |
| WO | WO-2010125416 A1 | 11/2010 |
| WO | WO-2010135731 A1 | 11/2010 |
| WO | WO-2012119070 A2 | 9/2012 |
| WO | WO-2013041967 A2 | 3/2013 |
| WO | WO-2014161002 A2 | 10/2014 |
| WO | WO-2015031186 A1 | 3/2015 |
| WO | WO-2015031187 A1 | 3/2015 |
| WO | WO-2015094392 A1 | 6/2015 |
| WO | WO-2016205068 A1 | 12/2016 |
| WO | WO-2016205069 A1 | 12/2016 |
| WO | WO-2016205071 A1 | 12/2016 |
| WO | WO-2017053646 A1 | 3/2017 |
| WO | WO-2017160548 A1 | 9/2017 |
| WO | WO-2019135927 A1 | 7/2019 |
| WO | WO-2020076769 A1 | 4/2020 |
| WO | WO-2020117637 A1 | 6/2020 |
| WO | WO-2020219707 A1 | 10/2020 |
| WO | WO-2022081204 A1 | 4/2022 |
| WO | WO-2022232205 A1 | 11/2022 |
| WO | WO-2023091439 A1 | 5/2023 |
| WO | WO-2023114347 A1 | 6/2023 |

OTHER PUBLICATIONS

Co-pending U.S. Appl. No. 18/369,737, inventor Horn; Gerald, filed on Sep. 18, 2023.
Krise et al. A novel prodrug approach for tertiary amines. 2. Physicochemical and in vitro enzymatic evaluation of selected N-phosphonooxymethyl prodrugs. J Pham Sci 88(9):922-927 (1999).
Mäntylä et al. Design, synthesis and in vitro evaluation of novel water-soluble prodrugs of buparvaquone. Eur J Pharm Sci 23(2):151-158 (2004).
Pramanik et al. A new route to cevimeline. Tetrahedron Letters 54(24):3043-3045 (2013).
PubChem CID-22416839, Dec. 5, 2007.
U.S. Appl. No. 17/988,366 Office Action dated Jan. 8, 2024.
U.S. Appl. No. 18/239,072 Office Action dated Nov. 21, 2023.
PCT/US2024/024819 International Search Report and Written Opinion dated Jul. 15, 2024.
Akorn Incorporated MSDS: Tropicacyl (R); Rev. 11-11 (date unknown).
Berge et al. Pharmaceutical Salts. Journal of Pharmaceutical Sciences 66(1):1-19 (Jan. 1977).
Bijsluiter: Glaucocare. Available at https://consumed.nl/bijsluiters/glaucocare. Machine Translation Provided.
CAS printout for Mashkovskii, The Relation Between the Chemical Structure and Pharmacological Activity of Some Esters of 3-Hydroxyquinuclidine (Quinuclidine-3-ol), Proc. Intern. Pharmacol., 7:359-366 (1961).
Chung et al., The effect of dioptric blur on reading performance. Vision Res 47(12):1584-94 (2007).

(56) References Cited

OTHER PUBLICATIONS

Cowan et al., Clinical evaluation of a new mydriatic-mydrilate. Br J Ophthalmol 46(12):730-6 (1962).
Davidson., General medicine and visual side effects. Br Med J 1(6166):821 (1979).
Drance et al., Dose response of human intraocular pressure to aceclidine. Arch Ophthalmol 88(4):394-6 (1972).
Edwards., Behaviour of the fellow eye in acute angle-closure glaucoma. Br J Ophthalmol 66(9):576-9 (1982).
Edwards et al., Effect of brimonidine tartrate 0.15% on night-vision difficulty and contrast testing after refractive surgery, J Cataract Refract Surg. 34(9):1538-41 (2008).
Ehlert et al. The interaction of the enantiomers of aceclidine with subtypes of the muscarinic receptor. J Pharmacol Exp Ther 279(3):1335-1344 (1996).
Fechner et al., Accomodative effects of aceclidine in the treatment of glaucoma. Amer J Ophth. 79 (1):104-106 (1975).
Francois et al. Ultrasonographic study of the effect of different miotics on the eye components. Ophthalmologica 175(6):328-338 (1977).
Fricke et al. Global Prevalence of Presbyopia and Vision Impairment from Uncorrected Presbyopia: Systematic Review, Meta-analysis, and Modelling. Ophthalmology 125(10):1492-1499 (2018).
Gardiner., ABC of Ophthalmology: accidents and first aid. Br Med J 2(6148):1347-50 (1978).
Gardiner., ABC of Ophthalmology: Methods of examination. Br Med J 2(6152):1622-6 (1978).
Glaucadrine, poudre et solvant pour collyre en solution, boite de 1 acon de lyophilisat + acon le solvant de 10 ml GI. Available at Http://www.doctissimo.fr/medicament-GLAUCADRINE.htm Machine Translation Provided.
Glaunorm toma all'Indice farmaci. Available at http://www.anibaldi.eu/farmaci/schedetecniche/GLAUNORM.html. (last updated Dec. 15, 2012) Machine Translation Provided.
Grünberger et al., The pupillary response test as a method to differentiate various types of dementia. Neuropsychiatr 23(1):52-57 (2009).
Hoyng et al., The combination of guanethidine 3% and adrenaline 0.5% in 1 eyedrop (GA) in glaucoma treatment. Br J Ophthalmol 63(1):56-62 (1979).
Ishikawa et al. Selectivity of muscarinic agonists including (+/−)-aceclidine and antimuscarinics on the human intraocular muscles. J Ocul Pharmacol Ther 14(4):363-373 (1998).
Josefa Valcarcel, Glaucostat(R) 2% colirio. Machine Translation Provided.
Kaufman et al. Presbyopia and Glaucoma: Two Diseases, One Pathophysiology? The 2017 Friedenwald Lecture. Invest Ophthalmol Vis Sci 60(5):1801-1812 (2019).
Kibbe. Handbook of Pharmaceutical Excipients. 3rd Edition, American Pharmaceutical Association and Pharmaceutical Press (pp. 416-419) (2000).
Latanoprost Label (2006).
Lubrizol Pharmaceutical Bulletin 21 (Lubrizol Advanced Materials, Inc.) May 31, 2011.
Mayama et al. Myopia and advanced-stage open-angle glaucoma. Ophthalmology 109(11):2072-2077 (2002).
Mayo Clinic: Tropicamide (Opthalmic Route), 2015, http://www.mayoclinic.org/drugs-supplements/tropicamide-ophthalmic-route/description/drg-20066481.
Mohan et al., Optimal dosage of cyclopentolate 1% for cycloplegic refraction in hypermetropes with brown irides. Indian J Ophthalmol 59(6):514-6 (2011).
Muller and R.P. Dessing (Eds.) 4th Edition, European Drug Index, European Society of Clinical Pharmacy, Jeutscher Apotheker Verlag Suttgart (p. 550) (1997).
Nayak et al., A comparison of cycloplegic and manifest refractions on the NR-1000F (an objective Auto Refractometer). Br J Ophthalmol 71(1):73-5 (1987).
Park., The comparison of mydriatic effect between two drugs of different mechanism. Korean J Ophthalmol 23(1):40-2 (2009).

PCT/US2014/052256 International Search Report and Written Opinion dated Dec. 18, 2014.
PCT/US2016/036687 International Search Report and Written Opinion dated Sep. 9, 2016.
PCT/US2016/036692 International Search Report and Written Opinion dated Sep. 22, 2016.
PCT/US2016/036694 International Search Report and Written Opinion dated Oct. 26, 2016.
PCT/US2017/021244 International Search Report and Written Opinion dated May 22, 2017.
PCT/US2019/055116 International Search Report and Written Opinion dated Dec. 19, 2019.
PCT/US2019/063923 International Invitation to Pay Additional Fees dated Feb. 3, 2020.
PCT/US2019/063923 International Search Report and Written Opinion dated Apr. 23, 2020.
PCT/US2021/029536 International Search Report and Written Opinion dated Aug. 9, 2021.
PCT/US2022/026435 International Invitation to Pay Additional Fees dated Jul. 5, 2022.
PCT/US2022/026435 International Search Report and Written Opinion dated Sep. 28, 2022.
PCT/US2022/050028 International Search Report and Written Opinion dated Mar. 2, 2023.
Primožič et al. Influence of the acyl moiety on the hydrolysis of quinuclidinium esters catalyzed by butyrylcholinesterase. Croatica Chemica Acta 84(2):245-249 (2011).
Prospectus/Technical Sheet for Glaucostat Josefa Valcarecel Glaucostat® 2% colirio (2000).
PubChem 233021624 deposited on Feb. 12, 2015 (Feb. 12, 2015).
PubChem 427198483 deposited Aug. 13, 2020 (Aug. 13, 2020).
PubChem-CID-22416839, Create Date: Dec. 5, 2007.
Romano., Double-blind cross-over comparison of aceclidine and pilocarpine in open-angle glaucoma. Br J Ophthalmol 54(8):510-21 (1970).
Smith et al., Subsensitivity to cholinoceptor stimulation of the human iris sphincter in situ following acute and chronic administration of cholinomimetic miotic drugs. Br J Pharmacol 69(3):513-8 (1980).
Stella. Prodrugs: Some Thoughts and Current Issues. J Pharm Sci 99(12):4755-4765 (2010).
Tataru et al., Antiglaucoma pharmacotherapy. J Med Life 5(3):247-51 (2012).
Trinavarat et al., Effective pupil dilatation with a mixture of 0.75% tropicamide and 2.5% phenylephrine: A randomized controlled trial. Indian J Ophthalmol 57(5):351-4 (2009).
U.S. Appl. No. 14/223,639 Office Action dated Jan. 5, 2015.
U.S. Appl. No. 14/223,639 Office Action dated Sep. 30, 2014.
U.S. Appl. No. 14/742,903 Office Action dated Dec. 2, 2015.
U.S. Appl. No. 14/742,903 Office Action dated Jul. 17, 2015.
U.S. Appl. No. 14/742,903 Office Action dated Jul. 15, 2015.
U.S. Appl. No. 14/860,770 Office Action dated Dec. 13, 2016.
U.S. Appl. No. 14/860,777 Office Action dated Mar. 9, 2017.
U.S. Appl. No. 15/073,089 Office Action dated May 8, 2017.
U.S. Appl. No. 15/073,089 Office Action dated Nov. 30, 2016.
U.S. Appl. No. 15/073,139 Office Action dated Dec. 1, 2016.
U.S. Appl. No. 15/235,431 Office Action dated Mar. 9, 2018.
U.S. Appl. No. 15/864,703 Office Action dated Apr. 8, 2019.
U.S. Appl. No. 15/864,703 Office Action dated Feb. 11, 2019.
U.S. Appl. No. 15/864,703 Office Action dated Mar. 26, 2018.
U.S. Appl. No. 15/956,931 Office Action dated Oct. 2, 2018.
U.S. Appl. No. 15/956,936 Office Action dated Feb. 11, 2019.
U.S. Appl. No. 15/956,936 Office Action dated Sep. 28, 2018.
U.S. Appl. No. 16/106,730 Office Action dated Jun. 11, 2021.
U.S. Appl. No. 16/106,730 Office Action dated Jun. 2, 2020.
U.S. Appl. No. 16/106,730 Office Action dated Oct. 19, 2020.
U.S. Appl. No. 16/156,276 Office Action dated Jun. 26, 2020.
U.S. Appl. No. 16/156,276 Office Action dated Oct. 22, 2020.
U.S. Appl. No. 16/700,088 Office Action dated May 28, 2021.
U.S. Appl. No. 16/700,088 Office Action dated Nov. 2, 2021.
U.S. Appl. No. 16/747,070 Office Action dated Jun. 25, 2021.
U.S. Appl. No. 16/747,070 Office Action dated Oct. 30, 2020.
U.S. Appl. No. 16/796,364 Office Action dated Apr. 30, 2021.

(56) References Cited

OTHER PUBLICATIONS

U.S. Appl. No. 16/796,364 Office Action dated Dec. 30, 2020.
U.S. Appl. No. 16/796,364 Office Action dated Jun. 11, 2021.
U.S. Appl. No. 16/881,570 Office Action dated Oct. 7, 2020.
U.S. Appl. No. 17/069,155 Office Action dated Aug. 19, 2021.
U.S. Appl. No. 17/242,398 Office Action dated Apr. 27, 2023.
U.S. Appl. No. 17/242,398 Office Action dated Oct. 14, 2022.
U.S. Appl. No. 17/502,066 Office Action dated Jun. 22, 2023.
U.S. Appl. No. 17/502,066 Office Action dated Mar. 31, 2022.
U.S. Appl. No. 17/502,066 Office Action dated Nov. 14, 2022.
U.S. Appl. No. 17/552,622 Office Action dated Feb. 9, 2023.
U.S. Appl. No. 17/552,654 Office Action dated Apr. 20, 2022.
U.S. Appl. No. 17/552,654 Office Action dated Dec. 2, 2022.
U.S. Appl. No. 17/988,366 Office Action dated Jul. 19, 2023.
Varma et al. Concentration of Latanoprost Ophthalmic Solution after 4 to 6 Weeks' Use in an Eye Clinic Setting. Invest Ophthalmol Vis Sci. 47(1):222-225 (2006).
Ward et al., 1,2,5-Thiadiazole analogues of aceclidine as potent ml muscarinic agonists. J Med Chem 41(3):379-392 (1988).
Wood et al., Pupil dilatation does affect some aspects of daytime driving performance. Br J Ophthalmol (11):1387-90 (2003).
Zhang et al. Reactive impurities in large and small molecule pharmaceutical excipients—A review. TrAC Trends in Analytical Chemistry 101:34-42 (2018).
Aceclidine (Hydrochloride) Item No. 1790. Product Information. Cayman Chemical Company (1 pg) (Dec. 2, 2022).
Charman, W. Neil. Pinholes and presbyopia: solution or sideshow? Ophthalmic Physiol Opt 39(1):1-10 (2019).
Co-pending U.S. Appl. No. 18/763,722, inventors Horn; Gerald et al., filed on Jul. 3, 2024.
Co-pending U.S. Appl. No. 18/765,066, inventors Horn; Gerald et al., filed on Jul. 5, 2024.
Co-pending U.S. Appl. No. 18/765,156, inventors Horn; Gerald et al., filed on Jul. 5, 2024.
Co-pending U.S. Appl. No. 18/766,429, inventors Horn; Gerald et al., filed on Jul. 8, 2024.
Drug information Q&A "Q29. What is the expiry date of drugs and how to store them properly?", Japan Pharmaceutical Manufacturers Association [online], Mar. 2014, [retrieved on Mar. 25, 2024], Retrieved from the Internet: URL: https://www.jpma.or.jp/about_medicine/guide/med_qa/q29.html (English translation provided).
Jiao, Jim. Polyoxyethylated nonionic surfactants and their applications in topical ocular drug delivery. Advanced Drug Delivery Reviewed 60:1663-1673 (2008).
Randazzo et al., Pharmacological management of night vision disturbances after refractive surgery Results of a randomized clinical trial. J Cataract Refract Surg 31(9):1764-1772 (2005).
Santvliet, et al. Determinants of Eye Drop Size. Survey of Ophthamology 49(2):197-213 (2004).
U.S. Appl. No. 17/502,066 Office Action dated Mar. 27, 2024.
U.S. Appl. No. 17/730,376 Office Action dated Jul. 17, 2024.
U.S. Appl. No. 17/988,366 Office Action dated Apr. 29, 2024.
U.S. Appl. No. 18/239,045 Office Action dated Jan. 26, 2024.
U.S. Appl. No. 18/239,072 Office Action dated Mar. 27, 2024.
U.S. Appl. No. 18/241,733 Office Action dated Jan. 30, 2024.
U.S. Appl. No. 18/369,737 Office Action dated Jun. 6, 2024.
U.S. Appl. No. 18/465,918 Office Action dated Feb. 1, 2024.
Xu, Renfeng et al. Effect of Target Luminance on Optimum Pupil Diameter for Presbyopic Eyes. Optom Vis Sci 93(11):1409-1419 (2016).

COMPOSITIONS AND METHODS FOR STORAGE STABLE OPHTHALMIC DRUGS

CROSS-REFERENCE

This application is a continuation of U.S. application Ser. No. 17/242,398, filed Apr. 28, 2021, which is a continuation in part of U.S. Application Ser. No. 17/069,155, filed Oct. 13, 2020, now Issued U.S. Pat. No. 11,273,150, which is a continuation in part of U.S. application Ser. No. 16/595,789, filed Oct. 8, 2019, now Issued U.S. Pat. No. 10,836,760, which claims the benefit of U.S. Provisional Application No. 62/743,720, filed Oct. 10, 2018, each of which are incorporated by reference herein in their entireties.

BACKGROUND OF THE INVENTION

Several ophthalmic drugs must be diluted just prior to instillation or if pre-formulated have a limited shelf life or require cold storage. Current ophthalmic drugs that suffer from stability issues include aceclidine, latanoprost, latanoprost-timolol, chloramphenicol, azasite, cyclopentolate, proteins, peptides, amino acids and their derivatives.

Aceclidine has been shown effective for the treatment of glaucoma. Current aceclidine formulations require lyophilization of the aceclidine and mixing with a diluent just prior to instillation. Aceclidine has also been demonstrated to treat presbyopia, an eye condition that effects almost every person starting around 40 years of age. See U.S. Pat. Nos. 9,089,562; 9,314,427; 9,320,709; 9,833,441; 9,844,537; 9,968,594; 10,052,313; 10,064,818; 10,307,408; 10,617,763 and 10,959,990.

Latanoprost has also been shown to effectively treat glaucoma. Like aceclidine, latanoprost requires cold storage due to a limited shelf life at room temperature.

The instability of these ophthalmic drugs including aceclidine and latanoprost cause inconvenience, reduced efficacy and increased costs for both the subjects in need of these treatments and the companies that manufacture, sell and package these drugs.

Thus, there is a need in the art for a method of stabilizing ophthalmic drugs such that an increase in shelf life is achieved.

SUMMARY OF THE INVENTION

In certain other embodiments, the present invention is directed to a method of stabilizing an ophthalmic drug comprising the following steps:
a) adding a surfactant and a viscosity enhancer to the ophthalmic drug to create a composition wherein the composition has a viscosity of about 25 centipoise or less at a shear rate of $\frac{1}{1000}$ per second at 25 degrees Celsius and a viscosity of about 70 centipoise or more at shear rate of 1 per second at 25 degrees Celsius;
b) filling the composition from step a) into a container; and
c) storing the container at a temperature from about 2 degrees Celsius to about 25 degrees Celsius, preferably from about 2 to about 8 degrees Celsius and more preferably at about 5 degrees Celsius.

In certain other embodiments, the ophthalmic drug is selected from the group consisting of aceclidine, latanoprost, latanoprost-timolol, chloramphenicol, azasite, cyclopentolate, proteins, peptides, amino acids, salts thereof, derivatives thereof and combinations thereof.

In certain other embodiments, the container of the present invention comprises a closure and a vessel wherein a portion of the closure and a portion of the vessel are sealed with an anti-leaching material selected from the group consisting of biaxially-oriented polyethylene terephthalate, polytetrafluorethylene and aluminum foil, preferably biaxially-oriented polyethylene terephthalate.

In certain other embodiments, the container of the present invention is disposed in a second container that is formed with or lined with an anti-leaching material selected from the group consisting of biaxially-oriented polyethylene terephthalate, polytetrafluorethylene and aluminum foil, preferably biaxially-oriented polyethylene terephthalate.

In certain other embodiments, the present invention is directed to a method of stabilizing a composition comprising aceclidine comprising storing the composition in a container having a headspace at a temperature from about 22 degrees Celsius to about 25 degrees Celsius, wherein the container comprises a closure and a vessel wherein a portion of the closure and a portion of the vessel are sealed with an anti-leaching material selected from the group consisting of biaxially-oriented polyethylene terephthalate, polytetrafluorethylene and aluminum foil and/or the container is disposed in a second container that is formed with or lined with biaxially-oriented polyethylene terephthalate, polytetrafluorethylene and aluminum foil.

In certain other embodiments, the second container comprises a second closure, wherein the second closure provides an airtight seal.

In certain other embodiments, the airtight seal is resealable.

In certain other embodiments, the ophthalmic drug is aceclidine is at a concentration from about 0.25% to about 4.0% w/v aceclidine.

In certain other embodiments, the methods of the present invention provide at least 90% stability of the ophthalmic drug for at least 7 months, at least 8 months, at least 12 months, at least 15 months, at least 18 months, at least 20 months or at least 22 months or at least 24 months.

In certain other embodiments, the compositions of the present invention have a viscosity of about 0.5 centipoise or less at a shear rate of $\frac{1}{1000}$ per second at 25 degrees Celsius and a viscosity of about 150 centipoise or more, preferably 300 centipoise or more at at shear rate of 1 per second at 25 degrees Celsius.

In certain other embodiments, the compositions of the present invention has a viscosity from about 75 to about 1,000 centipoise at a shear rate of 0.

In certain other embodiments, the present invention is directed to a method of stabilizing a composition comprising aceclidine, hydroxypropylmethyl cellulose, polysorbate 80, mannitol, sorbate and an antioxidant selected from the group consisting of sodium ascorbate, sodium bisulfate, sodium metabisulfite, n-acetyl cysteine or a combination thereof comprising storing the composition in a container having a headspace at a temperature from about 2 degrees Celsius to about 8 degrees Celsius, wherein the composition is filled into the container under an inert gas overlay, preferably nitrogen and the headspace is purged with an inert gas, preferably nitrogen.

In certain other embodiments, the aceclidine is at a concentration from about 0.25% to about 4.00% w/v, the hydroxypropylmethyl cellulose is at a concentration from about 0.75% to about 1.25% w/v, polysorbate 80 is at a concentration from about 2% to about 4% w/v, mannitol is at a concentration from about 2% to about 4% w/v, sorbate is at a concentration from about 0.10% to about 0.12% w/v and the antioxidant is at a concentration from about 0.10% to about 0.25% w/v.

In certain other embodiments the present invention is directed to a container comprising an ophthalmic drug prepared by the process comprising the steps of:
  a) providing a container;
  b) filling the container with a composition comprising an ophthalmic drug, a surfactant and a viscosity enhancer, preferably under an inert gas overlay, preferably nitrogen, wherein the composition has a viscosity of about 25 centipoise or less at a shear rate of $1/1000$ per second at 25 degrees Celsius and a viscosity of about 70 centipoise or more at shear rate of 1 per second at 25 degrees Celsius;
  c) optionally, purging a headspace created during the filling step b) with an inert gas, preferably nitrogen;
  d) capping the container; and
  e) optionally, storing the container at a temperature from about 2 to about 25 degrees Celsius, preferably from about 2 to about 8 degrees Celsius and more preferably at about 5 degrees Celsius.

In certain other embodiments, the present invention is directed to a method of stabilizing a composition comprising aceclidine comprising storing the composition in a container having a headspace at a temperature from about 2 degrees Celsius to about 8 degrees Celsius, preferably at about 5 degrees Celsius.

In certain other embodiments, the compositions of the present invention are filled into the container under an inert gas overlay, preferably nitrogen, preferably the headspace is purged with an inert gas overlay, preferably nitrogen.

In certain other embodiments the present invention is directed to a composition comprising from about 0.25% to about 4.0% w/v aceclidine and one or more means of stabilizing the composition selected from the group consisting of filling the composition into a container under an inert gas overlay, preferably nitrogen and purging a headspace created during filling with the inert gas overlay, preferably nitrogen, having a total viscosity of the composition of at least 50 centipoise or more, adding a preservative to the composition selected from the group consisting of sorbate, benzalkonium chloride, sodium ascorbate, sodium bisulfate, sodium metabisulfite, n-acetyl cysteine and a combination thereof,
  wherein the composition is stored at a temperature from about 2 to about 8 degrees Celsius and
  wherein w/v denotes weight by total volume of the composition.

In certain other embodiments, the present invention is directed to a method of treating presbyopia comprising administering to a subject in need thereof a composition of the present invention.

In certain other embodiments, the present invention is directed to a method of treating a refractive error of the eye in a subject in need thereof comprising administering to a subject in need thereof a pharmaceutically acceptable amount of a composition of the present invention wherein the refractive error of the eye is selected from presbyopia, myopia, hyperopia, astigmatism or a combination thereof.

The present invention is further directed to a method of increasing the visual depth of field (i.e. depth of focus) secondary to pupil miosis, comprising administering to a subject in need thereof a pharmaceutically effective amount of an ophthalmological composition of the present invention.

The present invention is further directed to a method of reducing the side effects of ophthalmic aceclidine administration by modulating the agonist effect on the ciliary body of the eye such that ciliary spasm, ciliary induced brow ache, and/or ciliary induced headache are substantially reduced or eliminated.

The present invention is further directed to a method of allowing binocular physiologic topical presbyopic correction.

The present invention is further directed to a method of eliminating the need for monocular limitation due to distance blur, or reduced to treatment of mild hyperopes to counteract induced myopic blur, as typically associated with pilocarpine, or pilocarpine and alpha agonist combinations.

The present invention is further directed to a method of improving near vision by increasing accommodation without reduction in distance vision sharpness. This is achieved by simultaneously increasing incremental accommodation, modulated so that while sufficient to provide additive near vision enhancement, it remains at a rate of induction and total degree of accommodation such that the associated myopic blur does not break through the ability of the simultaneously induced pupil miosis pinhole effect to filter the refractive error and maintain distance sharpness.

The present invention is further directed to a method of increasing the visual depth perception upon improving near vision unaided comprising administering to a subject in need thereof a pharmaceutically effective amount of an ophthalmological composition of the present invention in both eyes (binocular vision), wherein such binocularity further enhances near vision beyond that of either eye separately.

The present invention is further directed to a method of improving vision in a subject with ametropia (vision abnormality), comprising administering to a subject in need thereof a pharmaceutically effective amount of a composition of the present invention.

The present invention is further directed to a method of improving vision in a subject with ametropia, comprising administering to a subject in need thereof a pharmaceutically effective amount of a composition of the present invention, wherein ametropia is selected from the group consisting of nearsightedness, farsightedness, regular astigmatism, irregular astigmatism and high degrees of regular astigmatism.

The present invention is further directed at eliminating optical aberrations induced by corneal irregularity, opacities, or very high degrees of regular astigmatism that include regions adjacent or peripheral to the central 1.5 mm optical zone, and thereby inducing improved visual acuity and quality of vision by filtering out these aberrant optics in those suffering from irregular astigmatism or high degrees of more regular astigmatism, such as occurs in conditions such as keratoconus, photorefractive keratectomy induced corneal haze, diffuse lamellar keratitis ("DLK") (post-lasik DLK), other iatrogenic corneal induced irregularity such as cataract incision, glaucoma filtering blebs, implanted glaucoma valves, corneal inlays with or without removal, ectasia post corneal surgery (lasik), and secondary to infection.

The present invention is further directed at improving acuity relative to existing uncorrected refractive error. Upon this improved acuity, patients now requiring toric contact lenses for astigmatism with reduced comfort and optics that may shift during each blink may in many cases require only non-toric soft contact lenses or no contact lenses. Further, those requiring gas permeable contact lenses may no longer require contact lenses or only require much more comfortable soft contact lenses. Patients with high degrees of astigmatism may now require no correction or reduced astigmatic correction. Patients with small to moderate degrees of nearsightedness may require less correction or no longer require correction. Patients with small to moderate degrees of hyperopia (farsightedness) may require no correction or reduced correction.

The present invention is directed to methods and ophthalmological compositions for improving eye sight. In a preferred embodiment the present invention is directed to methods and ophthalmological compositions for the treatment of presbyopia. In a more preferred embodiment the present invention is directed to ophthalmological compositions comprising aceclidine.

The present invention is directed to methods of treating irregular astigmatism, keratoconic ectasia, and low myopia, or hyperopia, with or without astigmatism, comprising administering to a subject in need thereof an ophthalmological composition of the present invention.

The present invention is further directed to a method of stabilizing aceclidine comprising providing a first composition comprising about 1.75% w/v aceclidine and about 2.5% w/v mannitol in a first chamber and a second composition comprising about 0.01% w/v tropicamide, about 4.0% w/v polysorbate 80, about 1.25% w/v hydroxypropylmethyl cellulose, about 0.10% to 0.12% w/v sorbic acid, about 0.1% w/v ethylenediaminetetraacetic acid dihydrate, about 0.02% w/v benzalkonium chloride and optionally, about 0.1% w/v sodium citrate or citrate buffer in a second chamber, wherein upon mixing the first composition and the second composition the efficacy of aceclidine is maintained for at least one month.

The present invention is further directed to a method of stabilizing aceclidine comprising storing a composition of the present invention at from 0 degrees Celsius to 8 degrees Celsius.

DETAILED DESCRIPTION OF THE INVENTION

Figure 1:
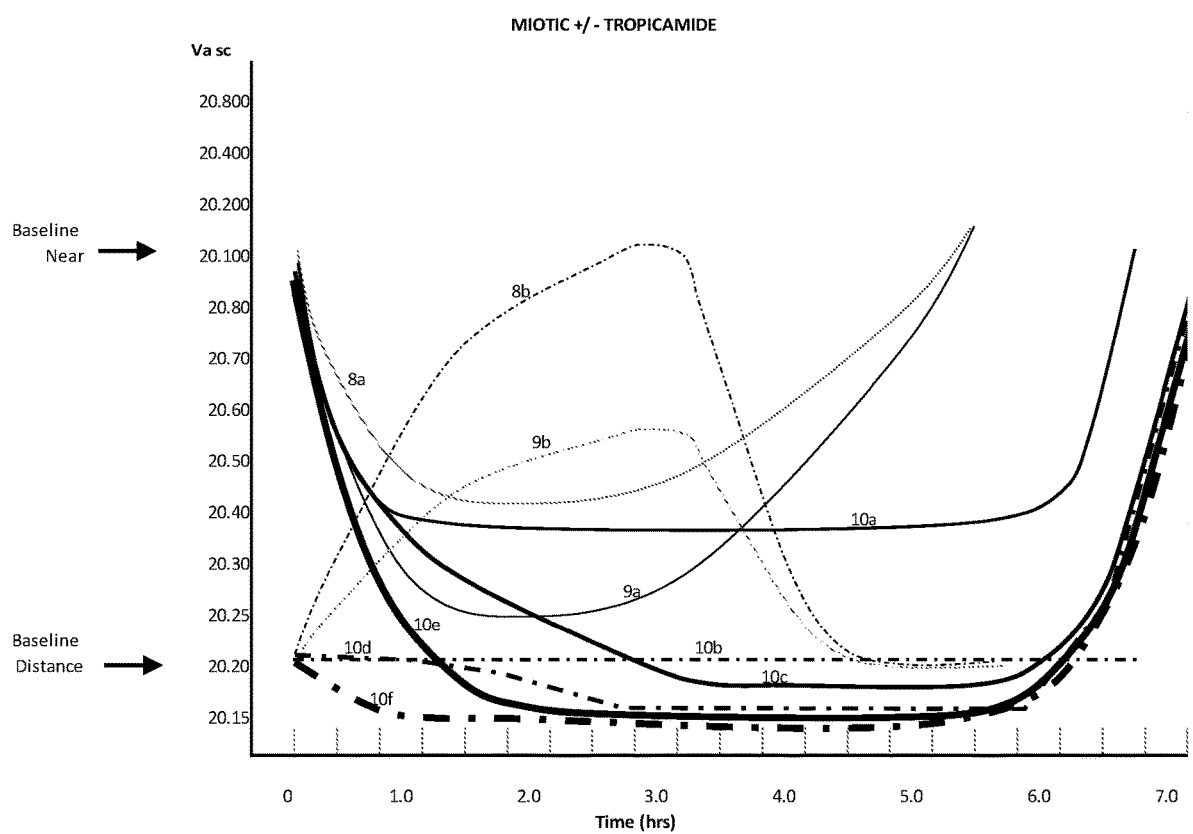
FIG. 1 is a graphical representation of the effects of pilocarpine and aceclidine with or without tropicamide and with or without a carrier on near and distance vision in a patient over the age of 45.

The present invention is directed to compositions and methods of stabilizing an ophthalmic drug by formulating the drug in a combination of surfactants and viscosity agents that achieve a nonlinear viscosity for the composition and storing the composition in a container.

Definitions

As used herein, the term "composition" is intended to encompass a product comprising the specified ingredients in the specified amounts, as well as any product which results, directly or indirectly, from a combination of the specified ingredients in the specified amounts.

The term "stabilizing", as used herein, refers to any process which facilitates and/or enables an active agent to remain in solution. The term "stabilizing", as used herein, also refers to any means or process which inhibits and/or reduces the tendency of an active agent including a muscarinic agonist, including aceclidine, to degrade.

As used herein, all numerical values relating to amounts, weights, and the like, that are defined as "about" each particular value is plus or minus 10%. For example, the phrase "about 5% w/v" is to be understood as "4.5% to 5.5% w/v." Therefore, amounts within 10% of the claimed value are encompassed by the scope of the claims.

As used herein "% w/v" refers to the percent weight of the total composition.

As used herein the term "subject" refers but is not limited to a person or other animal.

As used herein, the term "container" refers to a pharmaceutically acceptable container comprising a chamber suitable to house a liquid drug product. Containers include, for example, vials, syringes, capsules, and ampoules.

As used herein "headspace" refers to the area within the chamber of the container between the composition and the cap when the cap is oriented away from the pull of gravity.

As used herein, the term "cap" or "closure" refers to any article capable of preventing the composition from exiting the container.

The term muscarinic receptor agonist ("muscarinic agonist") encompasses agonists that activate muscarinic acetylcholine receptors ("muscarinic receptors"). Muscarinic receptors are divided into five subtypes named M1-M5. Muscarinic agonists of the present invention include those muscarinic agonists that preferentially activate M1 and M3 receptors over M2, M4 and M5 receptors ("M1/M3 agonists"). M1/M3 agonists include but are not limited to aceclidine, xanomeline, talsaclidine, sabcomeline, cevimeline, alvameline, arecoline, milameline, SDZ-210-086, YM-796, RS-86, CDD-0102A (5-[3-ethyl-1,2,4-oxadiazol-5-yl]-1,4,5,6-tetrahydropyrimidine hydrochloride), N-acylurea-substituted 3-morpholine arecolines, VUO255-035 (N-[3-oxo-3-[4-(4-pyridinyl)-1-piperazinyl]propyl]-2,1,3-benzothiadiazole-4-sulfonamide), benzylquinoline carboxylic acid (BQCA), WAY-132983, AFB267B (NGX267), AC-42, AC-260584, chloropyrazines including but not limited to L-687, 306, L-689-660, 77-LH-28-1, LY593039, and any quinuclidine ring with one or more carbon substitutions particularly that include an ester, sulfur, or 5 or 6 carbon ring structure including with substituted nitrogen(s) and or oxygen(s), or any pharmaceutically acceptable salts, esters, analogues, prodrugs or derivatives thereof. A preferred M1/M3 agonist is aceclidine. In a preferred embodiment, muscarinic agonist of the present invention include those muscarinic agonist that preferentially activate M1 and M3 over M2, M4, and M5; and even more preferably activate M1 over M3. In a more preferred embodiment muscarinic agonist of the present invention include those muscarinic agonists that only activate M1.

The term "aceclidine" encompasses its salts, esters, analogues, prodrugs and derivatives including, but not limited to, aceclidine as a racemic mixture, aceclidine (+) enantiomer, aceclidine (−) enantiomer, aceclidine analogues, including, but not limited to, highly M1 selective 1,2,5 thiadiazole substituted analogues like those disclosed in Ward. J. S. et al., 1,2,5-Thiadiazole analogues of aceclidine as potent m1 muscarinic agonists, *J Med Chem,* 1998 Jan. 29, 41(3), 379-392 and aceclidine prodrugs including but not limited to carbamate esters.

The term "selective α-2 adrenergic receptor agonists" or "α-2 agonist" encompasses all α-2 adrenergic receptor agonists which have a binding affinity of 900 fold or greater for α-2 over α-1 adrenergic receptors, or 300 fold or greater for α-2a or α-2b over α-1 adrenergic receptors. The term also encompasses pharmaceutically acceptable salts, esters, prodrugs, and other derivatives of selective α-2 adrenergic receptor agonists.

The term "inert gas" refers to gases that are chemically inert and do not react with other compounds. Inert gases include, but are not limited to, helium, neon, argon, krypton, xenon, radon and nitrogen.

The term "low concentrations" or "low-dose" of alpha-2 adrenergic receptor agonists refers to concentrations from between about 0.0001% to about 0.065% w/v; more preferably, from about 0.001% to about 0.035% w/v; even more preferably, from about 0.01% to about 0.035% w/v; and even more preferably, from about 0.03% to about 0.035% w/v.

The term "brimonidine" encompasses, without limitation, brimonidine salts and other derivatives, and specifically includes, but is not limited to, brimonidine tartrate, 5-bromo-6-(2-imidazolin-2-ylamino)quinoxaline D-tartrate, and Alphagan®.

The terms "treating" and "treatment" refer to reversing, alleviating, inhibiting, or slowing the progress of the disease, disorder, or condition to which such terms apply, or one or more symptoms of such disease, disorder, or condition.

The term "pharmaceutically acceptable" describes a material that is not biologically or otherwise undesirable (i.e. without causing an unacceptable level of undesirable biological effects or interacting in a deleterious manner).

As used herein, the term "pharmaceutically effective amount" refers to an amount sufficient to effect a desired biological effect, such as a beneficial result, including, without limitation, prevention, diminution, amelioration or elimination of signs or symptoms of a disease or disorder. Thus, the total amount of each active component of the pharmaceutical composition or method is sufficient to show a meaningful subject benefit. Thus, a "pharmaceutically effective amount" will depend upon the context in which it is being administered. A pharmaceutically effective amount may be administered in one or more prophylactic or therapeutic administrations.

The term "prodrugs" refers to compounds, including, but not limited to, monomers and dimers of the compounds of the invention, which have cleavable groups and become, under physiological conditions, compounds which are pharmaceutically active in vivo.

As used herein "salts" refers to those salts which retain the biological effectiveness and properties of the parent compounds and which are not biologically or otherwise harmful at the dosage administered. Salts of the compounds of the present inventions may be prepared from inorganic or organic acids or bases.

The term "higher order aberrations" refers to aberrations in the visual field selected from starbursts, halos (spherical aberration), double vision, multiple images, smeared vision, coma and trefoil.

The term "cold chain" refers to storage at temperatures from about 2 to about 8° C. from manufacture to immediately prior to administration.

The compounds of the present invention can be used in the form of pharmaceutically acceptable salts derived from inorganic or organic acids or bases. The phrase "pharmaceutically acceptable salt" means those salts which are, within the scope of sound medical judgment, suitable for use in contact with the tissues of humans and lower animals without undue toxicity, irritation, allergic response and the like and are commensurate with a reasonable benefit/risk ratio. Pharmaceutically acceptable salts are well-known in the art. For example, S. M. Berge et al. describe pharmaceutically acceptable salts in detail in J. *Pharmaceutical Sciences,* 1977, 66: 1 et seq.

The salts can be prepared in situ during the final isolation and purification of the compounds of the invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, hyaluronic acid, malic acid, sulphuric acid and phosphoric acid and such organic acids as oxalic acid, malic acid, maleic acid, methanosulfonic acid, succinic acid and citric acid.

Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium and aluminum salts and the like and nontoxic quaternary ammonia and amine cations including ammonium, tetramethylammonium, tetraethylammonium, methylammonium, dimethylammonium, trimethylammonium, triethylammonium, diethylammonium, and ethylammonium among others. Other representative organic amines useful for the formation of base addition salts include ethylenediamine, ethanolamine, diethanolamine, piperidine, piperazine and the like.

The term "ester" as used herein is represented by the formula —OC(O)A$^1$ or —C(O)OA$^1$, where A$^1$ can be alkyl, cycloalkyl, alkenyl, cycloalkenyl, alkynyl, cycloalkynyl, aryl, a heteroaryl group or other suitable substituent.

Methods of the Invention

In certain embodiments, the present invention is directed to a method of stabilizing an ophthalmic drug comprising the following steps:

a) adding a surfactant and a viscosity enhancer to the ophthalmic drug to create a composition wherein the composition has a viscosity of about 25 centipoise or less at a shear rate of $1/1000$ per second at 25 degrees Celsius and a viscosity of about 70 centipoise or more, preferably of about 150 centipoise or more and more preferably at about 300 centipoise or more at at shear rate of 1 per second at 25 degrees Celsius;
b) filling the composition from step a) into a container; and
c) storing the container at a temperature from about 2 degrees Celsius to about 25 degrees Celsius, preferably from about 2 to about 8 degrees Celsius and more preferably at about 5 degrees Celsius.

In certain other embodiments, the compositions of the present invention are filled into the container under an inert gas overlay, preferably nitrogen, preferably the headspace is purged with an inert gas overlay, preferably nitrogen.

In certain other embodiments, the ophthalmic drug is selected from the group consisting of aceclidine, latanoprost, latanoprost-timolol, chloramphenicol, azasite, cyclopentolate, proteins, peptides, amino acids, salts thereof, derivatives thereof and combinations thereof.

In certain other embodiments, the container of the present invention comprises a closure and a vessel wherein a portion of the closure and a portion of the vessel are sealed with an anti-leaching material selected from the group consisting of biaxially-oriented polyethylene terephthalate, polytetrafluorethylene and aluminum foil, preferably biaxially-oriented polyethylene terephthalate.

In certain other embodiments, the container of the present invention is disposed in a second container that is formed with or lined with an anti-leaching material selected from the group consisting of biaxially-oriented polyethylene terephthalate, polytetrafluorethylene and aluminum foil, preferably biaxially-oriented polyethylene terephthalate.

In certain other embodiments, the present invention is directed to a method of stabilizing a composition comprising aceclidine comprising storing the composition in a container having a headspace at a temperature from about 22 degrees Celsius to about 25 degrees Celsius, wherein the container comprises a closure and a vessel wherein a portion of the closure and a portion of the vessel are sealed with an anti-leaching material selected from the group consisting of biaxially-oriented polyethylene terephthalate, polytetrafluorethylene and aluminum foil and/or the container is disposed in a second container that is formed with or lined with biaxially-oriented polyethylene terephthalate, polytetrafluorethylene and aluminum foil.

In certain other embodiments, the second container comprises a second closure, wherein the second closure provides an airtight seal.

In certain other embodiments, the airtight seal is resealable.

In certain other embodiments, the ophthalmic drug is aceclidine is at a concentration from about 0.25% to about 4.0% w/v aceclidine.

In certain other embodiments, the methods of the present invention provide at least 90% stability of the ophthalmic drug for at least 7 months, at least 8 months, at least 12 months, at least 15 months, at least 18 months, at least 20 months or at least 22 months or at least 24 months.

In certain other embodiments, the compositions of the present invention have a viscosity of about 0.5 centipoise or less at a shear rate of $1/1000$ per second at 25 degrees Celsius and a viscosity of about 150 centipoise or more, preferably 300 centipoise or more at at shear rate of 1 per second at 25 degrees Celsius.

In certain other embodiments, the compositions of the present invention has a viscosity from about 75 to about 1,000 centipoise at a shear rate of 0.

In certain other embodiments, the present invention is directed to a method of stabilizing a composition comprising aceclidine, hydroxypropylmethyl cellulose, polysorbate 80, mannitol, sorbate and an antioxidant selected from the group consisting of sodium ascorbate, sodium bisulfate, sodium metabisulfite, n-acetyl cysteine or a combination thereof comprising storing the composition in a container having a headspace at a temperature from about 2 degrees Celsius to about 8 degrees Celsius, wherein the composition is filled into the container under an inert gas overlay, preferably nitrogen and the headspace is purged with an inert gas, preferably nitrogen.

In certain other embodiments, the aceclidine is at a concentration from about 0.25% to about 4.00% w/v, the hydroxypropylmethyl cellulose is at a concentration from about 0.75% to about 1.25% w/v, polysorbate 80 is at a concentration from about 2% to about 4% w/v, mannitol is at a concentration from about 2% to about 4% w/v, sorbate is at a concentration from about 0.10% to about 0.12% w/v and the antioxidant is at a concentration from about 0.10% to about 0.25% w/v.

In certain other embodiments the present invention is directed to a container comprising an ophthalmic drug prepared by the process comprising the steps of:
a) providing a container;
b) filling the container with a composition comprising an ophthalmic drug, a surfactant and a viscosity enhancer, preferably under an inert gas overlay, preferably nitrogen, wherein the composition has a viscosity of about 25 centipoise or less at a shear rate of $1/1000$ per second at 25 degrees Celsius and a viscosity of about 70 centipoise or more at at shear rate of 1 per second at 25 degrees Celsius;
c) optionally, purging a headspace created during the filling step b) with an inert gas, preferably nitrogen;
d) capping the container; and
e) optionally, storing the container at a temperature from about 2 to about 25 degrees Celsius, preferably from about 2 to about 8 degrees Celsius and more preferably at about 5 degrees Celsius.

In certain other embodiments the present invention is directed to a composition comprising from about 0.25% to about 4.0% w/v aceclidine and one or more means of stabilizing the composition selected from the group consisting of filling the composition into a container under an inert gas overlay, preferably nitrogen and purging a headspace created during filling with the inert gas overlay, preferably nitrogen, having a total viscosity of the composition of at least 50 centipoise or more, adding a preservative to the composition selected from the group consisting of sorbate, benzalkonium chloride, sodium ascorbate, sodium bisulfate, sodium metabisulfite, n-acetyl cysteine and a combination thereof,
wherein the composition is stored at a temperature from about 2 to about 8 degrees Celsius and
wherein w/v denotes weight by total volume of the composition.

Compositions of the Invention

Ophthalmic drugs suitable for use in the present invention include, but are not limited to, aceclidine, latanoprost, latanoprost-timolol, chloramphenicol, azasite, cyclopentolate, proteins, peptides, amino acids, salts thereof, derivatives thereof and combinations thereof.

Surfactants suitable for use in the present invention include nonionic, ionic and amphoteric (zwitterionic) surfactants. In a preferred embodiment, the surfactant used in the present invention are at a concentration above the critical micellar concentration for that surfactant.

Nonionic surfactants suitable for the present invention include cyclodextrins, polyoxyl alkyls, poloxamers, polysorbates or combinations thereof. Preferred embodiments include Poloxamer 108, Poloxamer 188, Poloxamer 407, Polysorbate 20, Polysorbate 80, ionically charged (e.g. anionic) beta-cyclodextrins with or without a butyrated salt (Captisol®) 2-hydroxypropyl beta cyclodextrin ("HPβCD"), alpha cyclodextrins, gamma cyclodextrins, Polyoxyl 35 castor oil, and Polyoxyl 40 hydrogenated castor oil or combinations thereof. Further, substitution of other nonionic surfactants compatible with ophthalmological use allows for similar formulation advantages, which may included but is not limited to one or more of a nonionizing surfactant such as poloxamer, poloxamer 103, poloxamer 123, and poloxamer 124, poloxamer 407, poloxamer 188, and poloxamer 338, any poloxamer analogue or derivative, polysorbate, polysorbate 20, polysorbate 40, polysorbate 60, polysorbate 80, any polysorbate analogue or derivative, cyclodextrin, hydroxypropyl-β-cyclodextrin, hydroxypropyl-γ-cyclodextrin, randomly methylated β-cyclodextrin, β-cyclodextrin sulfobutyl ether, γ-cyclodextrin sulfobutyl ether or glucosyl-β-cyclodextrin, any cyclodextrin analogue or derivative, polyoxyethylene, polyoxypropylene glycol, an polysorbate analogue or derivative, polyoxyethylene hydrogenated castor oil 60, polyoxyethylene (200), polyoxypropylene glycol (70), polyoxyethylene hydrogenated castor oil, polyoxyethylene hydrogenated castor oil 60, polyoxyl, polyoxyl stearate, nonoxynol, octylphenol ethoxylates, nonyl phenol ethoxylates, capryols, lauroglycol, polyethylene glycol ("PEG"), Brij® 35, 78, 98, 700 (polyoxyethylene glycol alkyl ethers), glyceryl laurate, lauryl glucoside, decyl glucoside, or cetyl alcohol; or zwitterion surfactants such as palmitoyl carnitine, cocamide DEA, cocamide DEA derivatives cocamidopropyl betaine, or trimethyl glycine betaine, N-2(2-acetamido)-2-aminoethane sulfonic acid (ACES), N-2-acetamido iminodiacetic acid (ADA), N,N-bis(2-hydroxyethyl)-2-aminoethane sulfonic acid (BES), 2-[Bis-(2-hydroxyethyl)-amino]-2-hydroxymethyl-propane-1,3-diol (Bis-Tris), 3-cyclohexylamino-1-propane sulfonic acid (CAPS), 2-cyclohexylamino-1-ethane sulfonic acid (CHES), N,N-bis(2-hydroxyethyl)-3-amino-2-hydroxypropane sulfonic acid (DIPSO), 4-(2-hydroxyethyl)-1-piperazine propane sulfonic acid (EPPS), N-2-hydroxyethylpiperazine-N'-2-ethane sulfonic acid (HEPES), 2-(N-morpholino)-ethane sulfonic acid (MES), 4-(N-morpholino)-butane sulfonic acid (MOBS), 2-(N-morpholino)-propane sulfonic acid (MOPS), 3-morpholino-2-hydroxypropanesulfonic acid (MOPSO), 1,4-piperazine-bis-(ethane sulfonic acid) (PIPES), piperazine-N,N'-bis(2-hydroxypropane sulfonic acid) (POPSO), N-tris (hydroxymethyl)methyl-2-aminopropane sulfonic acid (TAPS), N-[tris(hydroxymethyl)methyl]-3-amino-2-hydroxypropane sulfonic acid (TAPSO), N-tris(hydroxymethyl) methyl-2-aminoethane sulfonic acid (TES), 2-Amino-2-hydroxymethyl-propane-1,3-diol (Tris), tyloxapol, Solulan™ C-24 (2-[[10,13-dimethyl-17-(6-methylheptan-2-yl)-2,3,4,7,8,9,11,12,14,15,16,17-dodecahydro-1H-cyclopenta[a]phenanthren-3-yl]oxy]ethanol) and Span® 20-80 (sorbitan monolaurate, sorbitan monopalmitate, sorbitan monostearate, and sorbitan monooleate). In other embodiments the addition of polysorbate 80 is preferred. In addition to the above nonionic surfactants any nonionic surfactant is suitable for use in the present invention as long as the concentration of the nonionic surfactant is such that it is above the critical micellar concentration for that non-ionic surfactant. Preferably, the nonionic surfactants used in the present invention achieve submicron diameter micelles, more preferably less than 200 nanometers and more preferably less than 150 nanometers in diameter.

Ionic surfactants suitable for use in the present invention include, but are not limited to, anionic surfactants and cationic surfactants. Anionic surfactants suitable for use in the present invention include, but are not limited to, ammonium lauryl sulfate, dioctyl sodium sulfosuccinate, sodium laureth sulfate, linear alkylbenzene sulfonate, sodium dodecyl sulfate, perfluorooctanesulfonate, sodium lauryl sarcosinate, sodium myreth sulfate, sodium pareth sulfate, sodium stearate, lignosulfonate, sodium lauryl sulfate, a olefin sulfonate, ammonium laureth sulfate and sodium ester lauryl sulfate. Cationic surfactants suitable for use in the present invention include, but are not limited to benzalkonium chloride, benzethonium chloride, methylbenzethonium chloride, cetylpyridinium chloride, alkyl-dimethyl dichlorobenzene ammonium chloride, dequalinium chloride, phenamylinium chloride, cetyl trimethylammonium bromide, cetyl trimethylammonium chloride, cetrimonium bromide and cethexonium bromide.

Amphoteric (zwitterionic) surfactants are any surfactant simultaneously carrying an anionic charge and a cationic charge. Amphoteric surfactants suitable for use in the present invention include, but are not limited to, alkyl or alkenyl-amphoacetates or ampho-diacetates, alkylamphopropionates or -dipropionates, alkyl amphohydroxypropyl sultaines wherein the alkyl groups contain 8 to 24 carbon atoms such as coco or lauryl.

Surfactants may be used in the present invention at a concentration above their critical micellar concentration. The critical micellar concentration for any particular surfactant may be calculated by a person of skill in the art. In a preferred embodiment, the concentration of surfactants in the present invention is from about 1.5% to about 7% w/v. The selection of nonionic, cationic, or anionic surfactants is based largely on 1) drug interaction; and 2) ability to permeate the cornea; where the surfactant quality combined with a viscosity agent is key to the nonlinear (non-newtonian) viscosity created.

Ophthalmological in situ gels which may be substituted for or added in addition to one or more surfactants include but are not limited to gelatin, carbomers of various molecular weights including carbomer 934 P and 974 P, xanthan gums, alginic acid (alginate), guar gums, locust bean gum, chitosan, pectins and other gelling agents well known to experts in the art.

In other preferred embodiments, the nonionic surfactant is polysorbate 80 at a concentration from about 0.5% to about 10% w/v, more preferably from about 1% to about 7% w/v and even more preferably from about 2% to about 5% w/v, yet more preferably from about 2.5% to about 4% w/v and most preferably at about 2.5% or 2.75% or 3% or 4% or 5% w/v.

Viscosity agents suitable for the present invention include, but are not limited to gums such as guar gum, hydroxypropyl-guar ("hp-guar"), and xanthan gum, alginate, chitosan, gelrite, hyauluronic acid, dextran, Carbopol® (polyacrylic acid or carbomer) including Carbopol® 900 series including Carbopol® 940 (carbomer 940), Carbopol® 910 (carbomer 910) and Carbopol® 934 (carbomer 934), cellulose derivatives such as carboxymethyl cellulose ("CMC"), methylcellulose, methyl cellulose 4000, hydroxymethyl cellulose, hydroxypropyl cellulose, hydroxypropylmethyl cellulose, hydroxyl propyl methyl cellulose 2906, carboxypropylmethyl cellulose, hydroxypropylethyl cellulose, and hydroxyethyl cellulose, polyethylene glycol, polyvinyl alcohol, polyvinyl pyrrolidone, gellan, carrageenan, alginic acid, carboxyvinyl polymer or combinations thereof.

Viscosity agents may be used in the present invention at a concentration necessary to achieve a viscosity of about 0.5 centipoise or less at a shear rate of 1/1000 per second at 25 degrees Celsius and a viscosity of about 150 centipoise or more, preferably 300 centipoise or more at at shear rate of 1 per second at 25 degrees Celsius when combined with a surfactant above its critical micellar concentration.

In certain other embodiments, the compositions of the present invention has a viscosity from about 75 to about 1,000 centipoise at a shear rate of 0.

In another embodiment the viscosity agent will have an equilibration viscosity less than 100 cps, preferably from about 15 to about 35 cps, and most preferably at about 30 cps. In a preferred embodiment the viscosity agent is Carbopol® 940 (carbomer 940) at a concentration from about 0.05% to about 1.5% w/v, preferably from about 0.09% to about 1.0% w/v, more preferably at 0.09%, 0.25%, 0.5%, 0.75%, 0.9% or 1.0% w/v. In certain combinations it has been surprisingly discovered nonionic surfactant/viscosity combinations may result in phase separation over time with precipitate formation. In such situations, particularly for polyoxyls, in a preferred embodiment polyoxyl 40 stearate, and cellulose derivatives, particularly hydroxypropylmethyl cellulose, use of a nonpolysaccharide derivative for viscosity enhancement, such as polyacrylic acid derivatives (carbomers, carbomer 934 or 940 in preferred embodiments) may prevent such separation; or alternatively use of a non polyoxyl nonionic surfactant, such as polysorbate 80 with either a cellulose derivative or noncellulose derivative viscosity agent may be substituted.

In another preferred embodiment, the viscosity agent is carboxymethyl cellulose at a concentration from about 1% to about 2% w/v, more preferably from 1.35% to about 1.45% w/v and most preferably 1.42% w/v or 1.40% w/v.

In another preferred embodiment, the viscosity agent is hydroxypropylmethyl cellulose at a concentration from about 0.5% to about 1.75%, and more preferably about 0.75% or 1.5%, still more preferably from about 1.0% to about 1.5%, and most preferably at about 1.25%.

Compositions of the present invention may further comprise cryoprotectants, polyols, bulking agents, solubilizers, antioxidants, tonicity adjustors, preservatives, Cryoprotectants are compounds that either prevent freezing or prevent damage to compounds during freezing. As used herein, the term "cryoprotectant" or "cryoprotectants" include lyoprotectants. Cryoprotectants suitable for use in the subject invention include, but are not limited to, a polyol, a sugar, an alcohol, a lower alkanol, a lipophilic solvent, a hydrophilic solvent, a bulking agent, a solubilizer, a surfactant, an antioxidant, a cyclodextrin, a maltodextrin, colloidal silicon dioxide, polyvinyl alcohol, glycine, 2-methyl-2,4-pentanediol, cellobiose, gelatin, polyethylene glycol (PEG), dimethyl sulfoxide (DMSO), formamide, antifreeze protein 752 or a combination thereof.

As used herein the term "polyol" refers to compounds with multiple hydroxyl functional groups available for organic reactions such as monomeric polyols such as glycerin, pentaerythritol, ethylene glycol and sucrose. Further, polyols may refer to polymeric polyols including glycerin, pentaerythritol, ethylene glycol and sucrose reacted with propylene oxide or ethylene oxide. In a preferred embodiment, polyols are selected from the group consisting of mannitol, glycerol, erythritol, lactitol, xylitol, sorbitol, isosorbide, ethylene glycol, propylene glycol, maltitol, threitol, arabitol and ribitol. In a more preferred embodiment, the polyol is mannitol.

Sugars suitable for use in the present invention as cryoprotectants include, but are not limited to, glucose, sucrose, trehalose, lactose, maltose, fructose and dextran.

In another preferred embodiment, alcohols include, but are not limited to, methanol.

In one embodiment, the present invention individually excludes each cryoprotectant from the definition of cryoprotectant.

Cryoprotectants may be at present in compositions of the present invention at a concentration from about 0.1% to about 99% w/v, preferably from about 1% to about 50% w/v, more preferably from about 1% to about 10% w/v.

As used herein "lower alkanols" include C1-C6 alkanols. Lower alkanols, suitable for use in the present invention include, but are not limited to, amyl alcohol, butanol, sec-butanol, t-butyl alcohol, n-butyl alcohol, ethanol, isobutanol, methanol. isopropanol and propanol.

Bulking agents suitable for use in the present invention include, but are not limited to, saccharide, polyvinylpyrrolidone, cyclodextrin and trehalose.

Solubilizers suitable for use in the present invention include, but are not limited to, cyclic amide, gentisic acid and cyclodextrins.

In a preferred embodiment, antioxidants suitable for use in the present invention include, but are not limited to, bisulfite, ascorbic acid, disodium- or tetrasodium ethylenediaminetetraacetic acid, citrate, butylated hydroxyanisole ("BHA"), butylated hydroxytoluene ("BHT"), a sulfoxylate, propyl gallate, an amino acid containing a thio group, and a thiol. In a preferred embodiment the antioxidant is disodium ethylenediaminetetraacetic acid at a concentration from about 0.005% to about 0.50% w/v, citrate at a concentration from about 0.01% to about 0.3% w/w, dicalcium diethylenetriamine pentaacetic acid ("Ca2DTPA") at a concentration from about 0.001% to about 0.2% w/v, preferably about 0.01% w/v Ca2DTPA which can be formulated by adding 0.0084% w/v Ca(OH)2 and 0.0032% w/v pentetic acid to the formulation and mixing slowly. Further combinations of antioxidants can be used. Other antioxidants that can be used with the present invention include those well known to experts in the art such as ethylenediaminetetraacetic acid at a concentration from about 0.0001% to about 0.015% w/v.

A tonicity adjustor can be, without limitation, a salt such as sodium chloride ("NaCl"), potassium chloride, mannitol or glycerin, or another pharmaceutically or ophthalmologically acceptable tonicity adjustor. In certain embodiments the tonicity adjustor is 0.037% w/v NaCl, Preservatives that can be used with the present invention include, but are not limited to, benzalkonium chloride ("BAK"), sorbic acid, oxychloro complex, citric acid, chlorobutanol, thimerosal, phenylmercuric acetate, disodium ethylenediaminetetraacetic acid, phenylmercuric nitrate, perborate or benzyl alcohol. In a preferred embodiment the preservative is BAK, sorbic acid, oxychloro complex or a combination thereof. In a yet more preferred embodiment BAK is at a concentration of about 0.001% to about 1.0% w/v, more preferably at a concentration of about 0.007%, 0.01% or 0.02% w/v. In another preferred embodiment the preservative is perborate at a concentration of 0.01% to about 1.0% w/v, more preferably at a concentration of about 0.02% w/v.

Various buffers and means for adjusting pH can be used to prepare ophthalmological compositions of the invention. Such buffers include, but are not limited to, acetate buffers, citrate buffers, phosphate buffers and borate buffers. It is understood that acids or bases can be used to adjust the pH of the composition as needed, preferably of 1 to 10 mM concentration, and more preferably about 3 mM or 5 mM. In a preferred embodiment the pH is from about 4.0 to about 8.0, in a more preferred embodiment the pH is from about 5.0 to about 7.0.

Aceclidine

One ophthalmic drug that may be stabilized by the methods of the present invention is aceclidine. Aceclidine is traditionally used as a treatment for glaucoma. When aceclidine is used to treat glaucoma it is normally stored in a two-bottle system; one bottle containing the lyophilized aceclidine and the second bottle containing the diluent necessary to reconstitute the lyophilized aceclidine before topical instillation. Romano J. H., Double-blind cross-over comparison of aceclidine and pilocarpine in open-angle glaucoma, *Brit J Ophthal*, August 1970, 54(8), 510-521. It is a further aspect of the present invention to provide an aqueous aceclidine composition that is stable in combination with cold chain storage. It is yet a further aspect of the present invention to provide a method of stabilizing aqueous aceclidine by combining effective excipients, pH ranges and temperature ranges.

The compositions and methods of the present invention treat presbyopia by improving depth of focus in patients with presbyopia by administering an ophthalmological composition to the eye that reduces pupil dilation in the dark or in dim light, produces a particular degree and duration of miosis without accommodation, provides cosmetic whitening and/or induce redness prophylaxis. The compositions and methods of the present invention also do not cause significant pupil rebound, tachyphylaxis, ciliary spasms, induction of myopia or reduction in distance vision. Additionally, the compositions and methods of the present invention allow for the further improvement in visual acuity and depth perception of binocular (both eyes) treatment. The ophthalmological composition of the present invention surprisingly creates a pupil of from about 1.5 to about 2.4 mm at the anterior iris plane and about 2.0 mm at the corneal surface. Not wishing to be held to particular theory the clinical effect appears to involve both with modulated increase in accommodative tone and enhanced pinhole near depth of focus for improved near vision, estimated to be about −1.25 D or less, but restricted in power to remain within the range of pinhole correction for distance, found to be about −1.00 D or less creating a sum increase that may in some cases create a near vision add of +2.00 D or more without distance blur; and with a reduction or ablation of the redness that is otherwise a hallmark of the use of miotic agents. The pupil miosis of the present invention with such modulation and restriction of peak accommodative tone is superior to the pinhole effect of the Kamra® and Flexivue Microlens® corneal inlays, allowing binocular treatment without peak dimming. Pupil miosis of the present invention with modulated accommodation is also superior to inlays because the constriction of the actual pupil does not result in the attendant severe night vision disturbance caused by the light scattering borders of the pre-corneal pinholes created by the inlays. Further pupil miosis provides a greater field of vision and transmission of more focused light, and in a discovered optimal pupil range of about 1.5 mm to 2.1 mm using formulation discoveries of the present invention does so with negligible to mild and very tolerable dimming and enhanced contrast, distance vision, reduced glare at night, and improved near vision.

The use of aceclidine has a minimal effect on the longitudinal ciliary muscle, thus reducing risk of retinal detachment when compared to the use of general muscarinic agonists such as pilocarpine and carbachol. The further inclusion of a cycloplegic agent resulted in only 0.04 mm of anterior chamber shallowing. Aceclidine, particularly as enhanced for the present invention, also has greater magnitude, duration, and control of minimum pupil diameter than conventional pilocarpine with or without alpha agonists, and less anterior chamber inflammation with chronic use. Compositions of the present invention achieve these advantages by allowing both pinhole near vision depth perception benefit and modest accommodative increase below the threshold of induced myopic distance blur through the miotic pupil, whereby, not wishing to be held to particular theory, it is believed the rate of miosis and the rate of accommodative increase maintain a synchronous balance in preferred embodiments allowing pinhole correction of otherwise induced accommodative blur in prior art applications of miotics for presbyopic correction. This combination thus is found to avoid the distance blur typically seen in patients as a response to pilocarpine and/or carbachol induced miosis without the formulation discoveries of the present invention, as well as the excessive accommodative myopia and ciliary spasm manifested as brow ache or generalized migraine-like headache.

Such conventional formulations of pilocarpine, in order to effect any reasonable duration of effect, are still restricted to less than or equal to about 4 hours in most cases, as the high ratio of accommodation to pupillary miosis requires minimal concentrations of pilocarpine of about 1.0% to minimize but not eliminate distance induced myopic blur and ciliary spasm. Further pilocarpine must be instilled monocularly to minimize intolerable distance blur to a still bothersome 2-3 lines of distance blur. Even instilled monocularly, pilocarpine still may create bothersome attendant distance blur and must be restricted to about 1.0%. Upon instillation of 1.0% pilocarpine pupil size is about 2.3 mm or larger in most subjects and thereby restricts any significant pinhole depth perception benefit as well as any pinhole filtering of induced myopic rays. The restriction to about 1.0% for these conventional formulations of pilocarpine with the attendant short duration and still bothersome but reduced distance blur in emmetropes or myopes (somewhat neutralized in low hyperopes) are attempts to prevent extremely strong accommodation of 5D to 11 D well known to occur at higher concentrations of pilocarpine.

Any effects on accommodation may be further reduced or totally eliminated in preferred embodiments by combining a miotic with a cycloplegic agent in a narrow and particular ratio of miotic to cycloplegic, where such ratios as discovered for U.S. Pat. No. 9,089,562, such as about 35:1 for a preferred embodiment, become greatly increased for the present invention in the presence of cryoprotectant as to a factor of about 300%-700%. Aceclidine is capable of producing the increased depth of focus by both pupil miosis below 2.3 mm and modest accommodation described in the present invention. Particularly enhanced miosis occurs with use of compositions of the present invention. This enhanced miosis makes it possible to use an α-2 agonist at very low concentrations if desired to reduce mild eye redness. Other combinations of inactive ingredients reduce or effectively eliminate induced redness without such agonists. Further, due to the apparent and surprisingly selective nature of aceclidine, and the commercially stable aceclidine formulation discoveries of the present invention, administration to the eye of compositions of the present invention result in a net strongly enhanced near vision acuity from both pupil miotic pinhole effect and moderate modulated ciliary accommodation. These beneficial effects are accompanied by a filtering pupil effect, which eliminates any distance blur from the accommodation, correcting residual refractive error and optical aberrations as may exist to in many cases improve distance vision as well. Thus, the administration of aceclidine results in pupil miosis without excessive accommodation and attendant distance blur. However, aceclidine alone may cause substantial redness and brow ache. Without formulation enhancement of the present invention such as requiring cycloplegic agent, cryoprotectant or both, aceclidine may produce either less than optimal pupil miosis at low concentrations or at higher concentrations require more than desired peak miosis to attain satisfactory duration of greater than 3-4 hours. However the use of a cycloplegic agent has been found to be highly sensitive to other inactive ingredients in the formulation not usually associated with effects on active agents, and particularly for cryoprotectants as found to be preferred commercially for aceclidine reduce or eliminate the need for this cycloplegic requirement to extremely low concentrations in a preferred embodiment, rendering 0.042% sufficiently high when a cryoprotectant is present (e.g. a polyol such as mannitol) to cause substantial loss of efficacy. Further, aceclidine without formulation enhancements of the present invention causes dimming of vision in dim or absent lighting as well as ciliary pain above a reasonably tolerable threshold that may last for an hour or more and be similar to a severe migraine headache.

Certain embodiments of the present invention enhance the discovered preferred degree of pupillary miosis by providing a consistent range of effect of about 1.50-2.20 mm for most patients using a preferred embodiment of a nonionic surfactant and viscosity agent. Similar benefit may be achieved using other permeation enhancers, particularly hydroxypropylmethyl cellulose, high viscosity carboxymethyl cellulose, Carbopol® (polyacrylic acid or carbomer), and various viscosity additives that increase drug residence time, such as xanthan gums, guar gum, alginate, and other in situ gels well known to experts in the art. It is well known to experts in the art that the exact concentration of a specific viscosity agent will depend on both the molecular weight for that agent selected and the concentration, such that for increased molecular weight a reduced concentration can have the same viscosity. The present invention further prevents nasal congestion otherwise occurring when substantial aceclidine levels reach the nasal mucosa, due to the rheologic properties of the preferred embodiment.

The combination of aceclidine and a low concentration of a selective α-2 adrenergic receptor agonist (α-2 agonist or α-2 adrenergic agonist), such as fadolmidine, brimonidine or guanfacine, allows for the desired miotic effect with diminished or no redness. The use of low concentrations of a selective α-2 agonist results in substantial reduction of hyperemia with greatly reduced risk of rebound hyperemia that is found in concentrations of about 0.06% w/v or more. Furthermore, the use of low concentrations of selective α-2 agonist does not adversely modify the pupil constriction caused by aceclidine. In contrast, the use of brimonidine 0.20% w/v, when topically applied for pupil modulation for night vision, result in tachyphylaxis of pupil modulation due to α-2 receptor upregulation in almost 100% of treated subjects within four weeks of use.

Unexpectedly, the addition of a cycloplegic agent results in reduction of any brow ache or associated discomfort by further reducing the degree of ciliary spasms on topical instillation without impairing the miotic response. More unexpectedly and surprisingly, the ratio of 1.40% aceclidine to about 0.040% tropicamide in a preferred embodiment of U.S. Pat. No. 9,089,562 (35:1) becomes about 1.75% aceclidine to about 0.004% to 0.010% tropicamide (350:1, 175:1 respectively) in the presence of mannitol, where 2.5% provides better effect than 4.0%.

The lack of impairment of the miotic response is an unexpected surprising discovery, as particular cycloplegic agents, such as tropicamide, have known pupil dilating effects at concentrations as low as 0.01% w/v (Grünberger J. et al., The pupillary response test as a method to differentiate various types of dementia, Neuropsychiatr, 2009, 23(1), pg 57). More specifically cycloplegic agents cause pupil mydriasis (i.e. dilation of the radial muscle of the iris). Further, the addition of a cycloplegic agent to the miotic agent unexpectedly increases the time at which the pupil maintains the desired size range without becoming too restricted. Peak miotic effect at 30-60 minutes can be titrated in inverse relation to the cycloplegic concentration. The concentrations of tropicamide discovered in the present invention apparently cause more relaxation of the ciliary muscle than the iris radial musculature. In fact, iris mydriasis is discovered to be suppressed by the addition of tropicamide to compositions containing concentrations of aceclidine used in the present invention, with instead a more consistent level of miosis for the duration of the miotic effect. Additionally and quite surprisingly, unexpectedly, and beneficially the addition of tropicamide can reduce the degree of peak pupil miosis without inducing mydriasis thereby creating a more constant and ideal pupil size throughout the drug induced miosis. This more consistent pupil size allows for beneficial near and distance vision without the adverse dimming or loss of resolution due to diffraction limits at the very reduced pupil sizes seen at peak pupil miosis (e.g. 1.25 mm).

Previously, in U.S. Pat. No. 9,089,562, it was surprisingly found that the addition of at least 0.04% w/v cycloplegic agent resulted in an abatement of ciliary side effects caused by the administration of aceclidine (1.40%) to the eye, in a preferred embodiment, but such formulations are not as constituted sufficiently stable for commercial use, and typically have a duration of about five to six hours maximum.

Several additional discoveries of the present invention allow for commercially stable aceclidine formulations with enhanced efficacy and duration:

Equally or more surprising than the synergistic effects of cyloplegics of 0.040% added to aceclidine 1.40%, is the discovery of the present invention that combination of aceclidine 1.50%-2.0%, and preferably about 1.75% and a cryoprotectant, preferably a polyol, in a preferred embodiment mannitol, particularly at 0.5% to 4.0% and most preferably about 2.5%, can achieve a similar pupil range with reduced or absent ciliary side effects. The cryoprotectant when combined with aceclidine can then be combined to allow lyophilization without degradation of aceclidine and simultaneously further reduce or eliminate the need for a cycloplegic agent for the present invention vs. the teachings of cycloplegic concentration ranges required in U.S. Pat. No. 9,089,562. Optionally, the addition of a cryoprotectant can therefore also be used to greatly reduce (i.e. no more than 0.025% w/v cycloplegic agent, preferably 0.004% to 0.015% and most preferably 0.005% to 0.010%) the concentration of cycloplegic required to further eliminate mild, but potentially bothersome, ciliary side effects particularly in younger presbyopes and further modulate pupil miosis over aceclidine and a cryoprotectant combinations alone, reducing and in most cases eliminating any bothersome peak concentration dimming, as found in preferred embodiments of the present invention. In preferred embodiments it is discovered that aceclidine about 1.50%-2.0% and more preferably 1.75% and mannitol about 0.5%-4.0% and more preferably 2.5% provide optimal concentration combinations for the present invention, that are necessary but not sufficient for about 3 lines of near improvement and 5 or more hours duration desired for an effective topical presbyopic composition, where additional formulation discoveries can further enhance the desired clinical near improvement magnitude and duration;

It is surprisingly discovered that adding a viscosity agent to compositions described in a. above only modestly improves magnitude and duration, however when first adding a nonionic surfactant, such as polyoxyl stearate or polysorbate 80, optimal concentrations are discovered that provide greatly improved magnitude and duration for the present invention, to which viscosity may then provide added duration much more substantially than when added alone. For polysorbate 80 or polyoxyl 40 stearate concentrations of 1.0% to 10.0%, and more preferably about 2.5% to 5.0% w/v have been found to be beneficial;

When formulation improvements of a. and b. above are combined, preferred embodiments such as aceclidine 1.75%, mannitol 2.5%, and polysorbate 80 2.75% result. Viscosity agents such as high viscosity carboxymethyl cellulose ("CMC") are surprisingly discovered to moderately enhance magnitude and greatly enhance duration, unlike with formulations in a. above alone. High molecular weight CMC concentrations of 0.75% to 1.75%, and most preferably about 1.40%, or hydroxypropylmethyl cellulose ("HPMC") at about 0.25% to 2.0%, more preferably about 0.50% or 1.50%, and most preferably about 1.0% to 1.25%, when combined result now in about +3 lines of near vision improvement or greater, at a duration of 5-10 hours, at a mean of about 7 hours or greater vs. pilocarpine 1.0% of about less than 4 hours;

Not wishing to be held to particular theory citrate in combination with EDTA as a preferred embodiment buffer appears to 1) reduce redness; 2) enhance sorbate preservative shelf life, and in combination of the above with BAK 0.005% to 0.02% (0.02% preferred) further enhances near vision lines to about 4 lines and duration to about 8 to 12 hours.

Additionally 0.5% or 1.5% sodium chloride is added in a preferred embodiment. Optionally, sodium chloride may be substituted with boric acid, preferably at 0.35% or potassium borate, preferably at 0.47%;

Not wishing to be held to particular theory, it appears the addition of nonionic surfactant at optimized concentration of about 2.5% to 5.0% enhances permeation of aceclidine into the eye, which may relate to optimal micellar size particularly once of micromicallar or nanomicellar range. This increased permeation coincides with the desirable increase in magnitude and duration and absent tropicamide but in the presence of mannitol with slight increases in ciliary sensation and dimming. Therefore in the presence of the combined formulation enhancements of a-d. above, where a cycloplegic agent is no longer required for a-d. above, addition of a nonionic surfactant at concentrations found to be preferred may be further improved with much lower concentrations of a cycloplegic agent than those found in U.S. Pat. No. 9,089,562, such as the use of about 0.042% tropicamide with aceclidine 1.40%. For the present invention then preferred embodiments include aceclidine of about 1.75%, mannitol 2.5%, polysorbate 80 of about 2.5% to 5.0%, CMC of about 1.42%, or HPMC of about 1.8% and tropicamide of about 0.004%-0.010%, more preferably about 0.005% to 0.007%, and most preferably about 0.005%-0.006%. Micelle formation above the critical micellar concentration may allow for micelles to spread across the tear film surface and spread at low concentrations to cover this surface, while at higher concentrations these micelles becoming increasingly contracted and "squeezed" along the surface. Not wishing to be held to particular theory, it is believed at an optimal concentration a minimal micelle diameter is achieved before significant multiple lamellae (layering) occurs. It is believed that at the optimal concentration nanomicelles of about 100 to 250 nm along the surface are achieved surrounding the highly charged and hydrophilic aceclidine, facilitating its penetration through the very lipophilic epithelium;

Not wishing to be held to particular theory the addition of BAK 0.02% to sorbate about 0.10%, EDTA about 0.10%, in a preferred composition of aceclidine 1.75%, mannitol 2.5%, tropicamide 0.01%, and citrate buffer (1 to 100 mM 3-5 mM preferred) is above the BAK critical micellar concentration. BAK, being a cationic surfactant, and BAK micelles, creating an ionic micellar gradient with + charge NH4+ quaternary nitrogen bring on the polar heads aggregating outside and lipophilic alkyl chain on the hydrophobic tails aggregating on the inside may cause significant similar aceclidine alignment due to its dipole with quaternary NH3 nucleophilic or NH4 protonated nitrogens oriented along the outside polar heads and more hydrophobic carbonyls C=O along hydrophobic BAK micellar tails these preventing, greatly reducing, or moderately reducing collisions of any nonionic aceclidine molecules—the nucleophiles—which if oriented in solution such that randomly they collide with another aceclidine carbonyl will result in chemical conversion of that aceclidine via nucleophilic attack at its targeted carbonyl, which can recur from such nucleophiles to other aceclidines so oriented repeatedly and cause loss of stability without such BAK orientation via 0.005% and preferably 0.01% to 0.02% most preferred micelles. The concentration of such nonionic nucleophiles at a preferred pH in the preferred embodiment is relatively low, but the ability of these nonionic nucleophiles to destabilize adjacent aceclidines repeatedly without themselves degrading is otherwise high. The result may be improved potency for 1 month plus of a mixed solution once opened in a dual chamber bottle and mixing occurs of lyophilized aceclidine/mannitol with the remainder of the formulation in the diluent and or improved stability sufficient for commercialization in solution, either at room temperature or via cold chain;

It is discovered that BAK alone does not provide sufficient bacterial and fungal preservative efficacy but that BAK and sorbate, or sorbate alone satisfactorily preserve diluent and or mixed solutions of the invention;

Not to be wishing to be held to particular theory preferred embodiments of the present invention such as containing 1.25% hydroxypropyl methyl cellulose may have a viscosity of about 400 cps prior to instillation, yet unlike conventional high viscosity artificial tear formulations such as Celluvisc® at about 400 cps, which may blur vision for 10-20 minutes or Liquigel® at about 100 cps, which causes similar but slightly reduced blurring causes only about 60 seconds of blur dissipating rapidly with an influx of tear secretion; where both a nonnewtonian reduction in viscosity at high shear (such as about ⅟₁₀₀₀ sec during a blink, and aceclidine parasympathetic trigger of tear secretion as a sialogen may contribute.

General miotic agents, such as pilocarpine, carbachol and phospholine diesterase, are capable of causing pupil miosis resulting in improved near vision of presbyopic patients. However, there is an inverse reduction in distance vision associated with these general miotic agents from miosis at peak effect and accommodation that is not seen with aceclidine. The co-administration of a cycloplegic agent with aceclidine surprisingly results in an attenuation of this reduction in distance vision.

Comfort, safety, and efficacy of a preferred embodiment of an ophthalmological composition of the present invention results from the presence of a nonionic surfactant, such as cyclodextrin alpha, beta, or gamma chains, preferably 2-hydroxypropyl beta-cyclodextrin ("HPβCD"), and, sulfobutyl ether derivative of β-cyclodextrin (Captisol®), a polyoxyl alkyl such as polyoxyl 40 stearate and polyoxyl 35 castor oil, or a poloxamer such as poloxamer 108 and poloxamer 407, a polysorbate such as polysorbate 80 or Brij® 35 (Brij is a registered trademark of Unigema Americas LLC); a viscosity enhancing agent, such as carboxymethyl cellulose ("CMC"); a tonicity adjustor, such as sodium chloride; a preservative, such as benzalkonium chloride and a pH from about 5.0 to about 8.0. Further, an increase in the concentration of the nonionic surfactant may result in reduced redness. Specifically, increasing polysorbate from 0.10% to 0.50-1.0% results in reduced redness. Further, increasing CMC or Carbopol® 940 from 0.50% to 1.5% w/v (preferably 1.40-1.43% w/v) results in enhanced near vision, both quantitative improvement and duration improvement.

The viscosity of compositions of the present invention comprising a viscosity agent may be from about 1 to about 10,000 cps prior to topical instillation in the eye. As a result of the shear force applied to the composition as it exits the device used for administration the viscosity is lowered to a range from about 1 to about 25 cps at the high shear of blinking, and 50 cps to 200 cps at the low shear between blinks, allowing greater drop retention with less spillage and less nasolacrimal drainage and systemic absorption upon topical instillation.

In one embodiment, the present invention is directed to an ophthalmological composition comprising aceclidine. In a preferred embodiment, aceclidine is at a concentration from about 0.25% to about 2.0% w/v, more preferably from about 0.50% to about 1.90% w/v, still more preferably from about 1.65% to about 1.85% w/v, and most preferably about 1.75% w/v. As aceclidine is a tertiary amine with asymmetry, both a + and − optical isomer exist (where in some studies (+) is more potent and in others it is felt (−) may be more potent). For the above concentrations polarimetry demonstrated an exactly equal ratio of (+) and (−) isomer for these concentrations. Altering this ratio could therefore alter this concentration range proportional to a change in ratio.

It is a discovery of the present invention that several modifications may singly or in combination be used to enhance cold chain stability storage, including in addition to in a preferred embodiment aceclidine 1.40%-1.75%, tropicamide 0.025%-0.10% and optionally a nonioinic surfactant such as polyoxyl 40 stearate 0.5%-10%, preferably 5.5% one or more of (See Table 1):

Acidic pH, preferably less than 5.5, preferably less than 5.0 and most preferably at a pH of about 4.75;

Viscosity agent, preferably at 25 C viscosity of about 15-50 cps, and more preferably 20-45 cps, where a preferred embodiment is carbomer 940 0.09%-1.5%;

Addition of a cryoprotectant, in a preferred embodiment a polyol, preferably Mannitol 2.5%-4.0%;

Addition of a buffer, where acetate or phosphate buffers are preferred, 2-100 mmole range with 3-5 mmole is preferred; and Addition of a preservative, where BAK 0.015% is preferred.

Muscarinic Agonists

The present invention is further directed to an ophthalmological composition comprising a muscarinic agonist, preferably a nonionic surfactant above its critical micellar concentration for the composition, and a viscosity enhancing agent; or alternatively an in situ gelling agent. In preferred embodiments the initial viscosity of the composition on topical application is above 20 cps, preferably 50 cps, and more preferably above 70 cps at low shear (1/s).

Muscarinic agonists include selective α-2 agonists, which may be included within the composition of the present invention or applied topically preferably just minutes before or less preferably just minutes afterward if additional means to reduce nasal congestion or redness is desired for sensitive subjects. Selective α-2 agonists suitable for the present invention have minimal α-1 agonist activity at low concentrations. For example, for brimonidine or fadolmidine, 1% to 2% w/v is considered extremely high, 0.5% to 1.0% w/v still highly inductive of α-1 receptors and toxic for purposes of the present invention. Further, 0.10% to 0.5% w/v is still too high and even 0.070% to 0.10% w/v is associated with a higher than preferred incidence of rebound hyperemia (however, for dexmedetomidine, its greater lipophilicity and intraocular penetration reduces rebound risk in this range). Only 0.065% w/v or below is potentially acceptable, where for most α-2 agonists, depending on degree of selectivity 0.050% w/v or even more preferably 0.035% w/v or less is desired. On the other hand some degree of useful activity may occur at one or more orders of magnitude further reduction of concentration. The preferred embodiments, brimonidine, fadolmidine and guanfacine, of the present invention preferentially stimulate α-2 adrenergic receptors, and even more preferably α-2b adrenergic receptors so that α-1 adrenergic receptors are not stimulated sufficiently enough to cause excessive large vessel arteriolar constriction and vasoconstrictive ischemia. In addition, it has been discovered that preventing or reducing redness for drugs that otherwise directly induce redness, such as the acetylcholine agonist, aceclidine, enhances compliance for sensitive subjects that may have induced redness or nasal congestion even with formulations of the present invention that do not include an α-2 agonist. However, because α-2 agonists are shifted to their ionized equilibrium an acidic pH is somewhat offset by the fact such agonists exert greater affect at neutral or alkaline pH. Therefore each α-2 agonist has a preferred pH range depending on its lipophilicity and pKa value when added to the inventive compositions with aceclidine. For the present invention while pH range of 5.0 to 8.0 is tolerated, preferred embodiments are at pH 5.5 to 7.5 and more preferably 6.5 to 7.0. Further, it has been discovered that cyclodextrins and/or polyoxyl 40 stearate as a nonionic surfactant component or as the sole nonionic surfactant, result in a greater whitening effect when the α-2 agonist is included in the composition rather than poloxamer 407. The α-2 agonist may optionally be applied separately or in certain preferred embodiments with formulations of the present invention that do not include an α-2 agonist, such as those formulas with polyoxyl 40 stearate 5.5% w/v as the non-ionic surfactant, although the α-2 agonist is not required except for occasional sensitive subjects. Fadolmidine represents the α-2 agonist with highest hydrophilicity and therefore high surface retention for the present invention. Guanfacine is also highly selective and hydrophilic. Brimonidine is highly selective with moderate lipophilicity. Finally, dexmedetomidine has high selectivity with high lipophilicity that may be used with less efficacy for reducing redness for the purposes of the present invention (although possibly inducing fatigue as a side effect in some patients). In a preferred embodiment using polyoxyl 40 stearate 5.5% w/v; CMC 0.80% w/v; NaCl 0.037% w/v; ethylenediaminetetraacetic acid ("EDTA") 0.015% w/v, borate buffer 5 mM and BAK 0.007% w/v results in redness of about 1.0 to 1.5 out of 4 which is transient lasting about ten minutes, and by 30 minutes returns to about baseline.

In one embodiment, the selective α-2 adrenergic receptor agonist is a compound which has binding affinity of about 900 fold or greater, even more preferably about 1000 fold or greater, and most preferably, about 1500 fold or greater.

The selective α-2 adrenergic receptor agonist may be present at a concentration from between about 0.0001% to about 0.065% w/v; more preferably, from about 0.001% to about 0.035% w/v; even more preferably, from about 0.01% to about 0.035% w/v; and even more preferably, from about 0.020% to about 0.035% w/v.

In one embodiment, the selective α-2 adrenergic receptor is selected from the group consisting of brimonidine, guanfacine, fadolmidine, dexmedetomidine, (+)-(S)-4-[1-(2,3-dimethyl-phenyl)-ethyl]-1,3-dihydro-imidazole-2-thione, 1-[(imidazolidin-2-yl)imino]indazole, and mixtures of these compounds. Analogues of these compounds that function as highly selective α-2 agonists may also be used in compositions and methods of the present invention.

In a more preferred embodiment, the selective α-2 agonist is selected from the group consisting of fadolmidine, guanfacine and brimonidine. In a yet more preferred embodiment the selective α-2 agonist is brimonidine in the form of a salt at a concentration of 0.025% to 0.065% w/v, more preferably from 0.03% to 0.035% w/v. In a preferred embodiment, the salt is a tartrate salt.

In another yet more preferred embodiment, the selective α-2 agonist is fadolmidine at a concentration from about 0.005% to about 0.05% w/v, more preferably from 0.02% to about 0.035% w/v in the form of a hydrochloride ("HCl") salt.

In another yet more preferred embodiment, the selective α-2 agonist is guanfacine at a concentration from about 0.005% to about 0.05% w/v, more preferably from 0.02% to about 0.035% w/v in the form of an HCl salt.

In another yet more preferred embodiment, the selective α-2 agonist is dexmedetomidine at a concentration from about 0.005% to about 0.05% w/v, more preferably from 0.04% to about 0.05% w/v in the form of an HCl salt.

In another preferred embodiment a pH less than physiologic pH is found to enhance the whitening effect for brimonidine, preferably pH 4.5 to 6.5, and more preferably pH 5.5 to 6.0.

However, redness reduction is achieved at all pHs, and enhancement of aceclidine absorption occurs at alkaline pH, such that more effect occurs from a given concentration, and therefore while effective at pH ranges from 4.5 to 8.0, pH range of 6.5 to 7.5 is preferred for the present invention, and 7.0 to 7.5 most preferred.

The present invention is further directed to an ophthalmological composition comprising a muscarinic agonist and further comprising a cycloplegic agent. It is a surprising and totally unexpected discovery of the present invention that certain cycloplegic agents can be combined with miotic agents, particularly for the present invention, aceclidine, without reducing miotic onset, magnitude, or duration; and further blunt the normally attendant spike in miotic effect coinciding with time of peak absorption in aqueous formulations to provide a constant miosis versus time after onset from 15 to 30 minutes to 6 to 10 hours depending on the desired formulation. The addition of the cycloplegic agent also reduces any residual associated discomfort that may otherwise occur soon after topical instillation, which presumably is a result of ciliary spasms or excessive pupillary miosis.

Cycloplegic agents suitable for the present invention include, but are not limited to, atropine, Cyclogyl® (cyclopentolate hydrochloride), hyoscine, pirenzepine, tropicamide, atropine, 4-diphenylacetoxy-N-methylpiperidine methobromide (4-DAMP), AF-DX 384, methoctramine, tripitramine, darifenacin, solifenacin (Vesicare), tolterodine, oxybutynin, ipratropium, oxitropium, tiotropium (Spriva), and otenzepad (a.k.a. AF-DX 116 or 11-{[2-(diethylamino)methyl]-1-piperidinyl}acetyl]-5,11-dihydro-6H-pyrido[2,3b][1,4]benzodiazepine-6-one). In a preferred embodiment the cycloplegic agent is tropicamide at a concentration from about 0.004% to about 0.025% w/v, more preferably from about 0.005% to about 0.015% w/v and still more preferably from about 0.005% to about 0.011% w/v, from about 0.005% to about 0.007% w/v and from about 0.005% to about 0.006% w/v. In another preferred embodiment the cycloplegic agent is a mixture of tropicamide at a concentration from about 0.04% to about 0.07% w/v or pirenzepine or otenzepad at a concentration from about 0.002% to about 0.05% w/v.

In a preferred embodiment, tropicamide 0.01% w/v was found to slightly reduce brow ache, 0.030% w/v to further reduce brow ache and from 0.04% to about 0.07% w/v to completely eliminate brow ache without reduction of the average pupillary miosis diameter over duration of effect. Tropicamide in preferred embodiments has demonstrated completely unexpected sensitivity of effect, where at about 0.04% w/v unexpectedly and very effectively reduces or eliminates brow ache and ciliary spasm pain, becoming very noticeably further reduced at 0.042% w/v and absent at 0.044% w/v in a preferred embodiment with no cycloplegia (surprising due to its common use as a pupil dilating agent). Yet, tropicamide did not reduce the mean degree of pupil miosis, the time of onset of pupil miosis or the subsequent visual benefits. On the contrary, tropicamide blunted the peak miosis seen in aqueous formulations to create a smooth consistent miotic effect over time. It allowed modulation of peak pupil miosis to achieve a more even effect over time with no dilation as has been found with its prior use. Specifically, tropicamide is useful to prevent transient constriction below 1.50 mm at 30 to 60 minutes following aceclidine in some embodiments and to reduce transient excessive and undesirable dimming of vision that may otherwise occur at peak onset of about 30 minutes. As an example, an ophthalmological composition comprising 1.53% w/v aceclidine, 5% w/v HPβCD, 0.75% w/v CMC, 0.25% w/v NaCl, 0.01% w/v BAK and a phosphate buffer at pH 7.0; or 1.45% w/v aceclidine; 5.5% w/v polyoxyl 40 stearate; 0.80% w/v CMC; 0.037% w/v NaCl; 0.015% w/v EDTA; 0.007% w/v BAK and 5 mM phosphate buffer at a pH 7.0; was varied from 0.040% w/v tropicamide, where moderate dimming was noted, to 0.044% w/v tropicamide where dimming became almost undetectable other than in extremely dim light conditions. This additional pupil size modulation with a cycloplegic agent allows aceclidine concentrations sufficient for prolonged effect while blunting the attendant peak excessive constriction that is undesirable as well as any uncomfortable brow ache. Surprisingly and due to its short-acting nature, tropicamide achieves this blunting effect without causing mydriasis. Further, in a preferred embodiment, tropicamide 0.014% w/v was found to reduce brow ache, 0.021% w/v to further reduce brow ache and from 0.028% to 0.060% w/v and in some embodiments up to 0.09% w/v to completely eliminate brow ache without cycloplegia (i.e. paralysis of ciliary muscle of the eye).

It has been found for a racemic 50:50 mixture of (+) and (−) aceclidine optical isomers (where in some studies (+) is more potent and in others it is felt (−) may be more potent) tropicamide effects may vary depending on the ratio of aceclidine to tropicamide. For example, in an ophthalmological composition of the present invention comprising 1.55% w/v aceclidine, 5.5% w/v HPβCD or in a preferred embodiment polyoxyl 40 stearate, 0.75% w/v CMC (1%=2,500 centipoise), 0.25% w/v NaCl, and 0.01% w/v BAK and at pH 7.5, 0.042% w/v tropicamide can be differentiated from even 0.035% w/v, with the former demonstrating normal indoor night vision and the latter slight dimming that becomes more noticeable at still lower concentrations. At higher concentrations, such as from about 0.075% to about 0.090% w/v tropicamide, loss of optimal range pupil constriction 1.50 mm to 1.80 mm range begins, and frank mydriasis at higher concentrations begins to occur. As isomer ratio may alter the effective concentration, this must be factored into the clinical efficacy anticipated using aceclidine; for preferred embodiments of the present invention a polarimeter was used to determine an exact 50:50 isomer ratio was used (personal communication Toronto Research Chemicals).

FIG. 1 shows the effect of a miotic agent with or without a cycloplegic agent and with or without a carrier. Subject is an emmetrope over the age of 45 with a baseline near vision of 20.100 and baseline distance vision of 20.20. Topical administration to the eye of 1% w/v pilocarpine in saline solution results in an improvement of near vision to 20.40 (8a), however this improvement comes at the expense of a reduction in distance vision to 20.100 (8b). The addition of 0.015% w/v tropicamide results in an improvement of near vision to 20.25 (9a) and a lessening of the reduction of distance vision to 20.55 (9b), though in certain instances with some induced irregular astigmatism (mildly blotched areas in reading field of vision). Topical administration of 1.55% w/v aceclidine in saline solution results in an improvement of near vision to 20.40 for an extended time period of 6 hrs (10a) without any effect on the baseline distance vision (10b). 10c and 10d show the effects of administering aceclidine in a carrier composed of 5.5% w/v 2-hydroxypropyl beta cyclodextrin, 0.75% w/v CMC (1%=2,500 centipoise), 0.25% w/v NaCl, and 0.01% w/v BAK. As seen in 10c the carrier increases the beneficial effect of aceclidine resulting in better than 20.20 near vision. As seen in 10d a similar increase in distance vision occurs. 10e and 10f show the effects of adding 0.042% w/v tropicamide to the aceclidine in the carrier. As seen in 10e near vision is improved to 20.15 with a quicker onset of maximum visual acuity. As seen in 10f a similar improvement is seen in distance vision. Taken together, FIG. 1 shows that aceclidine is capable of temporarily correcting near vision in a presbyopic subject without affecting the baseline distance vision. Similar results can be achieved with a different miotic agent, pilocarpine, with the addition of a cycloplegic agent such as tropicamide. A proper drug carrier can also have a beneficial effect.

It is a surprising and unexpected discovery that topical formulations of the present invention, particularly one of the preferred embodiments comprising aceclidine 1.35% to 1.55% w/v; 5.5% w/v polyoxyl 40 stearate; 0.80% w/v CMC; 0.037% w/v NaCl; 0.015% w/v EDTA; 0.007% w/v BAK; and 5 mM phosphate buffer at pH 7.0 result in considerably prolonged contact lens wear and comfort after a single topical instillation daily. The single daily use of the preferred embodiments allowed a subject with dry eye to sleep in his lenses for one week periods where previously even after a single night vision would be blurred and contact lenses coated with film requiring removal and cleaning or replacement (see Example 7).

In preferred embodiments, an ophthalmological composition of the present invention comprises aceclidine, a cryoprotectant, optionally a cycloplegic agent, a nonionic surfactant at a concentration from about 1% to about 5% w/v and a viscosity agent at a concentration of about 0.75% to about 1.6% w/v, preferably about 1.25% to about 1.5% w/v.

The following representative embodiments are provided solely for illustrative purposes and are not meant to limit the invention in any way.

REPRESENTATIVE EMBODIMENTS

In one embodiment, the ophthalmological composition comprises:
  aceclidine at a concentration of about 1.75% w/v; and
  mannitol at a concentration of about 2.5% w/v.

In another embodiment, the ophthalmological composition comprises:
  aceclidine at a concentration of about 1.75% w/v;
  mannitol at a concentration of about 2.5% w/v; and
  tropicamide at a concentration of about 0.02% w/v.

In another embodiment, the ophthalmological composition comprises:
  aceclidine at a concentration of about 1.75% w/v;
  mannitol at a concentration of about 2.5% w/v;
  polysorbate 80 at a concentration of about 5.0% w/v;
  carboxymethyl cellulose at a concentration of about 1.4% w/v;
  BAK at a concentration of about 0.015% w/v; and
  optionally, phosphate buffer at a concentration of about 3 mM,
  wherein the pH is about 5.

In another embodiment, the ophthalmological composition comprises:
  aceclidine at a concentration of about 1.75% w/v;
  mannitol at a concentration of about 2.5% w/v;
  polysorbate 80 at a concentration of about 0.5% w/v;
  NaCl at a concentration from about 0.10% to about 0.50% w/v;
  Carbopol® 940 at a concentration of about 0.95% w/v;
  BAK at a concentration of about 0.01% w/v; and
  optionally, phosphate buffer at a concentration of about 3 mM,
  wherein the pH is about 5.

In another embodiment, the ophthalmological composition comprises:
  aceclidine at a concentration of about 1.75% w/v;
  mannitol at a concentration of about 2.5% w/v;
  polysorbate 80 at a concentration of about 2.0% w/v;
  NaCl at a concentration of about 0.50% w/v Carbopol® 940 at a concentration of about 1.5% w/v;
BAK at a concentration of about 0.015% w/v; and
optionally, phosphate buffer at a concentration of about 3 mM,
wherein the pH is about 5.25.

In another embodiment, the ophthalmological composition comprises:
aceclidine at a concentration of about 1.75% w/v;
mannitol at a concentration of about 2.5% w/v;
polysorbate 80 at a concentration of about 0.25% w/v;
NaCl at a concentration of about 0.1% w/v;
boric acid at a concentration of about 0.12% w/v;
Carbopol® 940 at a concentration of about 0.95% w/v; and
BAK at a concentration of about 0.015% w/v;
wherein the pH is about 5.

In another embodiment, the ophthalmological composition comprises:
aceclidine at a concentration of about 1.75% w/v;
mannitol at a concentration of about 2.5% w/v;
polysorbate 80 at a concentration of about 0.50% w/v;
NaCl at a concentration of about 0.05% w/v;
boric acid at a concentration of about 0.2% w/v;
Carbopol® 940 at a concentration of about 0.95% w/v;
BAK at a concentration of about 0.01% w/v; and
optionally, phosphate buffer at a concentration of about 3 mM,
wherein the pH is about 5.

In another embodiment, the ophthalmological composition comprises:
aceclidine at a concentration of about 1.75% w/v;
mannitol at a concentration of about 2.5% w/v;
polysorbate 80 at a concentration of about 0.1% w/v;
boric acid at a concentration of about 0.2% w/v;
Carbopol® 940 at a concentration of about 0.9% w/v;
BAK at a concentration of about 0.05% w/v; and
optionally, phosphate buffer at a concentration of about 3 mM,
wherein the pH is about 5.

In another embodiment, the ophthalmological composition comprises:
aceclidine at a concentration of about 1.75% w/v;
mannitol at a concentration of about 2.5% w/v;
polysorbate 80 at a concentration of about 0.1% w/v;
NaCl at a concentration of about 0.1% w/v;
boric acid at a concentration of about 0.12% w/v;
Carbopol® 940 at a concentration of about 0.95% w/v;
BAK at a concentration of about 0.01% w/v; and
optionally, phosphate buffer at a concentration of about 3 mM,
wherein the pH is about 5.

In another embodiment, the ophthalmological composition comprises:
aceclidine at a concentration of about 1.75% w/v;
tropicamide at a concentration of about 0.01% w/v;
mannitol at a concentration of about 2.5% w/v;
polysorbate 80 at a concentration of about 5.0% w/v;
CMC at a concentration of about 1.4% w/v;
BAK at a concentration of about 0.015% w/v; and
optionally, phosphate buffer at a concentration of about 3 mM,
wherein the pH is about 5.

In another embodiment, the ophthalmological composition comprises:
aceclidine at a concentration of about 1.75% w/v;
tropicamide at a concentration of about 0.02% w/v;
mannitol at a concentration of about 2.5% w/v;
polysorbate 80 at a concentration of about 0.25% w/v;
NaCl at a concentration of about 0.1% w/v;
boric acid at a concentration of about 0.12% w/v;
Carbopol® 940 at a concentration of about 0.95% w/v; and
BAK at a concentration of about 0.01% w/v.
wherein the pH is about 5.

In another embodiment, the ophthalmological composition comprises:
aceclidine at a concentration of about 1.75% w/v;
tropicamide at a concentration of about 0.015% w/v;
mannitol at a concentration of about 2.5% w/v;
polysorbate 80 at a concentration of about 0.75% w/v;
NaCl at a concentration of about 0.05% w/v;
boric acid at a concentration of about 0.2% w/v;
Carbopol® 940 at a concentration of about 0.95% w/v;
BAK at a concentration of about 0.01% w/v; and
optionally, phosphate buffer at a concentration of about 3 mM.
wherein the pH is about 5.

In another embodiment, the ophthalmological composition comprises:
aceclidine at a concentration of about 1.75% w/v;
tropicamide at a concentration of about 0.025% w/v;
mannitol at a concentration of about 2.5% w/v;
polysorbate 80 at a concentration of about 0.1% w/v;
boric acid at a concentration of about 0.2% w/v;
Carbopol® 940 at a concentration of about 0.9% w/v;
BAK at a concentration of about 0.05% w/v; and
optionally, phosphate buffer at a concentration of about 3 mM.
wherein the pH is about 5.

In another embodiment, the ophthalmological composition comprises:
aceclidine at a concentration of about 1.75% w/v;
tropicamide at a concentration of about 0.02% w/v;
mannitol at a concentration of about 2.5% w/v;
polysorbate 80 at a concentration of about 0.1% w/v;
NaCl at a concentration of about 0.1% w/v;
boric acid at a concentration of about 0.12% w/v;
Carbopol® 940 at a concentration of about 0.95% w/v;
BAK at a concentration of about 0.01% w/v; and
optionally, phosphate buffer at a concentration of about 3 mM.
wherein the pH is about 5.

In another embodiment, the ophthalmological composition comprises:
aceclidine at a concentration of about 1.75% w/v;
tropicamide at a concentration of about 0.040% w/v;
polyoxyl 40 stearate at a concentration of about 5.0% w/v;
mannitol at a concentration of about 2.5% w/v;
optionally, acetate or phosphate buffer at a concentration of about 3.0 mM; and
BAK at a concentration of about 0.01% w/v,
wherein said composition has a pH of about 4.75.

In another embodiment, the ophthalmological composition comprises:
aceclidine at a concentration of about 1.55% w/v;
tropicamide at a concentration of about 0.040% w/v;
polyoxyl 40 stearate at a concentration of about 5.0% w/v;
citric acid monohydrate at a concentration of about 0.1% w/v;
mannitol at a concentration of about 4.0% w/v;
Carbopol® 940 at a concentration of about 0.09% w/v; and
optionally, acetate or phosphate buffer at a concentration of about 3.0 mM;
wherein said composition has a pH of about 5.0.

In another embodiment, the ophthalmological composition comprises:
   aceclidine at a concentration of about 1.50% w/v;
   tropicamide at a concentration of about 0.042% w/v;
   polyoxyl 40 stearate at a concentration of about 5.5% w/v;
   mannitol at a concentration of about 2.5% w/v;
   optionally, phosphate buffer at a concentration of about 3.0 mM;
   Carbopol® 940 at a concentration of about 0.85% w/v; and
   BAK at a concentration of about 0.01% w/v,
   wherein said composition has a pH of about 4.75.

In another embodiment, the ophthalmological composition comprises:
   aceclidine at a concentration of about 1.45% w/v;
   tropicamide at a concentration of about 0.042% w/v;
   polyoxyl 40 stearate at a concentration of about 5.5% w/v;
   citric acid monohydrate at a concentration of about 0.1% w/v;
   optionally, acetate buffer at a concentration of about 3.0 mM; and
   Carbopol® 940 at a concentration of about 0.75% w/v,
   wherein said composition has a pH of about 4.75.

In another embodiment, the ophthalmological composition comprises:
   aceclidine at a concentration of about 1.45% w/v;
   tropicamide at a concentration of about 0.042% w/v;
   polyoxyl 40 stearate at a concentration of about 5.5% w/v;
   mannitol at a concentration of about 2.0% w/v;
   citric acid monohydrate at a concentration of about 0.1% w/v;
   optionally, phosphate buffer at a concentration of about 3.0 mM; and
   Carbopol® 940 at a concentration of about 1.0% w/v,
   wherein said composition has a pH of about 4.75.

In another embodiment, the ophthalmological composition comprises:
   about 1.75% w/v aceclidine;
   about 2.5% w/v mannitol;
   about 2.75% w/v polysorbate 80; and
   about 1.25%; 1.0%-1.80% w/v hydroxypropylmethyl cellulose (depending on its molecular weight).

In another embodiment, the ophthalmological composition comprises:
   about 1.75% w/v aceclidine;
   about 0.005% to about 0.011% tropicamide;
   about 2.5% w/v mannitol;
   about 2.75% w/v polysorbate 80; and
   about 1.25%; 1.0%-1.80% w/v hydroxypropylmethyl cellulose (depending on its molecular weight).

In another embodiment, the ophthalmological composition comprises:
   about 1.75% w/v aceclidine;
   about 0.010% w/v tropicamide;
   about 2.5% w/v mannitol;
   about 5.0% w/v polysorbate 80;
   about 1.40% w/v carboxymethyl cellulose high viscosity;
   optionally, about 3 mM phosphate buffer; and
   about 0.010% BAK=as preservative,
   with a pH of about 5.0.

In another embodiment, the ophthalmological composition comprises:
   about 1.75% w/v aceclidine;
   about 0.006% w/v tropicamide;
   about 2.5% w/v mannitol;
   about 2.5% w/v polysorbate 80;
   about 1.25%; 1.0%-1.80% w/v hydroxypropylmethyl cellulose (depending on its molecular weight);
   optionally, about 3 mM phosphate buffer; and
   about 0.020% BAK=as preservative,
   with a pH of about 5.0.

In another embodiment, the ophthalmological composition comprises:
   about 1.75% w/v aceclidine;
   about 0.006% w/v tropicamide;
   about 2.5% w/v mannitol;
   about 2.5% w/v polysorbate 80;
   about 1.25%; 1.0%-1.80% w/v hydroxypropylmethyl cellulose (depending on its molecular weight);
   optionally, about 3 mM phosphate buffer;
   about 0.50% w/v NaCl; and
   about 0.020% BAK=as preservative,
   with a pH of about 5.0.

In another embodiment, the ophthalmological composition comprises:
   about 1.75% w/v aceclidine;
   about 2.5% w/v mannitol;
   about 3.5% w/v polysorbate 80;
   about 1.25%; 1.0%-1.80% w/v hydroxypropylmethyl cellulose (depending on its molecular weight);
   optionally, about 3 mM phosphate buffer;
   about 0.50% w/v NaCl; and
   about 0.020% BAK or 0.15% sorbic acid as preservative,
   with a pH of about 5.0.

In another embodiment, the ophthalmological composition comprises:
   about 1.75% w/v aceclidine;
   about 2.5% w/v mannitol;
   about 3.5% w/v polysorbate 80; and
   about 1.25%; 1.0%-1.80% w/v hydroxypropylmethyl cellulose (depending on its molecular weight);

In another embodiment, the ophthalmological composition comprises:
   about 1.75% w/v aceclidine;
   about 2.5% w/v mannitol;
   about 3.5% w/v polysorbate 80;
   about 1.25%; 1.0%-1.80% w/v hydroxypropylmethyl cellulose (depending on its molecular weight); and
   one or more excipient selected from the group consisting of about 0.50% w/v sodium chloride,
   about 0.02% w/v benzalkonium chloride, about 0.10% w/v sorbate, about 0.01% w/v ethylenediaminetetraacetic acid (EDTA) and 0.10% w/v citric acid.

In another embodiment, the ophthalmological composition comprises:
   about 1.75% w/v aceclidine;
   about 2.5% w/v mannitol;
   about 0.01% w/v tropicamide;
   about 0.1% w/v sodium citrate, anhydrous;
   about 0.02% w/v benzalkonium chloride;
   about 0.12% w/v sorbic acid;
   about 0.1% w/v disodium edetate dihydrate;
   about 4.0% w/v polysorbate 80; and
   about 1.25% w/v hydroxypropylmethyl cellulose,
   wherein the pH is about 5.0.

In another embodiment, the ophthalmological composition comprises:
   about 1.75% w/v aceclidine;
   about 2.5% w/v mannitol;
   about 0.01% w/v tropicamide;
   about 0.1% w/v sodium citrate, anhydrous;
   about 0.02% w/v benzalkonium chloride;
   about 0.1% w/v sorbic acid;

about 0.1% w/v EDTA;
about 3.5% w/v polysorbate 80; and
about 1.25%; 1.0%-2.25% w/v hydroxypropylmethyl cellulose (depending on its molecular weight),
wherein the pH is about 5.0.

In another embodiment, the ophthalmological composition comprises:
about 1.75% w/v aceclidine;
about 2.5% w/v mannitol;
about 0.01% w/v tropicamide;
optionally, about 3 mM phosphate buffer;
about 0.02% w/v benzalkonium chloride;
about 0.1% w/v sorbic acid;
about 0.10% w/v citrate;
about 3.5% w/v polysorbate 80; and about 1.25%; 0.25%-2.25% w/v hydroxypropylmethyl cellulose (depending on its molecular weight);
wherein the pH is about 5.0.

In another embodiment, the ophthalmological composition comprises:
aceclidine at a concentration of 1.5% w/v, mannitol at a concentration of 2.5% w/v.

In another embodiment, the ophthalmological composition comprises:
aceclidine at a concentration of 1.55% w/v, mannitol at a concentration of 2.5% w/v.

In another embodiment, the ophthalmological composition comprises:
aceclidine at a concentration of 1.6% w/v, mannitol at a concentration of 2.5% w/v.

In another embodiment, the ophthalmological composition comprises:
aceclidine at a concentration of 1.65% w/v, mannitol at a concentration of 2.5% w/v.

In another embodiment, the ophthalmological composition comprises:
aceclidine at a concentration of 1.7% w/v, mannitol at a concentration of 2.5% w/v.

In another embodiment, the ophthalmological composition comprises:
aceclidine at a concentration of 1.75% w/v, mannitol at a concentration of 2.5% w/v.

In another embodiment, the ophthalmological composition comprises:
aceclidine at a concentration of 1.80% w/v, mannitol at a concentration of 2.75% w/v and Carbopol® 940 at a concentration of 0.09% w/v.

In another embodiment, the ophthalmological composition comprises:
aceclidine at a concentration of 1.48% w/v, mannitol at a concentration of 1.5% w/v and Carbopol® 940 at a concentration of 0.50% w/v.

In another embodiment, the ophthalmological composition comprises:
aceclidine at a concentration of 1.80% w/v, mannitol at a concentration of 2.5% w/v and Carbopol® 940 at a concentration of 0.9% w/v.

In certain preferred embodiments, the present invention is directed to compositions for the treatment of presbyopia comprising about 1.75% w/w aceclidine, about 4.0% w/w polysorbate 80, about 2.5% w/w mannitol, about 1.2% w/w hydroxypropylmethyl cellulose, about 0.1% w/w ethylenediaminetetraacetic acid, about 0.02% w/w benzalkonium chloride, about 0.12% w/w potassium sorbate and about 0.077% w/w citrate, wherein the composition has a pH of about 5.0.

In certain preferred embodiments, the present invention is directed to compositions for the treatment of presbyopia comprising about 1.75% w/w aceclidine, about 4.0% w/w polysorbate 80, about 2.5% w/w mannitol, about 1.2% w/w hydroxypropylmethyl cellulose, about 0.1% w/w ethylenediaminetetraacetic acid, about 0.02% w/w benzalkonium chloride, about 0.12% w/w potassium sorbate and about 0.1% w/w citrate, wherein the composition has a pH of about 5.0.

In certain preferred embodiments, the present invention is directed to compositions for the treatment of presbyopia comprising about 1.40% w/w aceclidine, about 2.0% w/w polyoxyl stearate, about 2.5% w/w mannitol, about 0.1% w/w ethylenediaminetetraacetic acid, about 0.02% w/w benzalkonium chloride, about 0.12% w/w potassium sorbate and about 0.1% w/w citrate, wherein the composition has a pH of about 5.0.

The following Examples are provided solely for illustrative purposes and are not meant to limit the invention in any way.

EXAMPLES

Example 1 Effect of Aceclidine on Vision of Subjects Aged 47 to 67 Years

Table 1 demonstrates the effect on the near focus ability of presbyopic subjects before and after ophthalmological administration of a composition containing aceclidine. Each composition included aceclidine in the concentrations indicated and 5.5% w/v HPβCD, 0.75% w/v CMC, 0.25% w/v NaCl and 0.01% w/v BAK. Additionally compositions administered to subjects 4 and 5 included 0.125% w/v tropicamide. As aceclidine is an enantiomer, the clinical effectiveness may vary with different ratios. For the present studies a nearly exact 50:50 ratio of stereoisomers was measured as best determined by polarimetry.

TABLE 1

| | | Aceclidine | | Vision Baseline | | | | Post Gtt 15" | | | | |
|---|---|---|---|---|---|---|---|---|---|---|---|---|
| Effects of aceclidine on vision of presbyopic patients. | | | | | | | | | | | | |
| Date | # | Age | % | R Pre Dist | L Pre Dist | R Pre Near | L Pre Near | R Post Dist | L Post Dist | R Post Near: | L Post Near | Effect (h) |
| 8/21/2013 | 1 | 67 | 1.5 | 20.20 | 20.30 | 20.60 | 20.60 | 20.20 | 20.20 | 20.15 | 20.15 | 9.00 |
| 8/22/2013 | 2 | 52 | 1.5 | 20.30 | 20.30 | 20.50 | 20.50 | 20.25 | 20.25 | 20.25 | 20.20 | 8.00 |
| 8/23/2013 | 3 | 61 | 1.5 | 20.40 | 20.30 | 20.60 | 20.50 | 20.20 | 20.25 | 20.15 | 20.15 | 8.00 |
| 8/23/2013 | 4 | 61 | 1.1 | 20.20 | 20.25 | 20.80 | 20.50 | 20.15 | 20.15 | 20.20 | 20.15 | 12.00 |
| 8/23/2013 | 5 | 53 | 1.1 | 20.20 | 20.20 | 20.60 | 20.60 | 20.20 | 20.20 | 20.25 | 20.25 | 7.00 |
| 8/24/2013 | 6 | 47 | 1.5 | 20.25 | 20.25 | 20.100 | 20.100 | 20.20 | 20.20 | 20.15 | 20.15 | 8.00 |
| 8/25/2013 | 7 | 58 | 1.5 | 20.30 | 20.200 | 20.100 | 20.30 | 20.25 | 20.30 | 20.20 | 20.30 | 8.00 |

As seen in Table 1 all subjects had less than perfect near vision (20.20) in both the left and right eye (object at 15 inches from the eye) and most subjects had less than perfect distance vision before administration of the composition. After administration of the composition all subjects experienced an improvement in their near vision that lasted from 7 to 12 hours. Surprisingly, the majority of subjects also experienced improvement of their distance vision for the same time period. Still more surprisingly the improvement in near point was much closer than 16" typically required for comfortable reading, in some cases to about 8.5" more commonly seen in individuals 30 or less. The addition of tropicamide, a cycloplegic agent, had no additive or deleterious effect on vision correction.

Example 2 Effect of Concentration of Concentration of Aceclidine and Tropicamide the entire time vision was corrected. Switching the nonionic surfactant to HPβCD (formulas #2-6) further reduced the redness of the eye. Lowering of the concentration of aceclidine to 0.75% w/v (formula #3) further reduced eye redness but as mention above also reduced the vision correction duration of the formula.

A brow ache and stinging in the eye were noticeable in formulas #1-3 with a 2 out of 4 level of pain which was also associated with feelings of slight nausea, upset stomach and fatigue. Surprisingly, the addition of a cycloplegic agent, tropicamide, reduced brow ache and stinging to 0.5 out of 4 and 0 out of 4 respectively with brow ache dissipating after 60 minutes (formula #4). Further, the raising of the concentration of aceclidine to 1.1% w/v restored the longer duration of corrected vision seen in formulas #1-2 without increasing eye redness. However, upon re-topical instillation of formula #4 at the end of the 10 hours noticeable brow ache occurred. Topical instillation of formula #5 (OD) and (OS), with increased tropicamide concentrations, following formula #4 relieved the brow ache experienced with re-instal-

TABLE 2

Effect of concentration of concentration of aceclidine and tropicamide.

|  | #1 | #2 | #3 | #4 | #5 (OD) | #5 (OS) | #6 | #7 |
|---|---|---|---|---|---|---|---|---|
| Brsovadine | 0.03% | 0.03% | 0.03% | 0.03% | 0.03% | 0.03% | 0.03% |  |
| Polozamer 407 | 5.5% |  |  |  |  |  |  |  |
| HPBCD |  | 5.5% | 5.5% | 5.5% | 5.5% | 5.5% | 5.5% | 5.5% |
| Aceciliae | 1.5% | 1.5% | 0.75% | 1.1% | 1.1% | 1.1% | 1.1% | 11% |
| Tropicamide |  |  |  | 0.014% | 0.021% | 0.028% | 0.042% | 0.062% |
| Naci | 0.25% | 0.25% | 0.25% | 0.25% | 0.25% | 0.25% | 0.25% | 0.25% |
| CMC | 0.75% | 0.75% | 0.75% | 0.75% | 0.75% | 0.75% | 0.75% | 0.75% |
| BAK | 0.1% | 0.1% | 0.1% | 0.1% | 0.1% | 0.1% | 0.1% | 0.1% |
| Redness (15 m) | 3+ | 1 | 0.5 | 0.5 | 0 | 0 | 0 | 0 |
| Redness (30 m) | 1.5 | 0.5 | 0.25 | 0.25 | 0 | 0 | 0 | 0 |
| Brow Ache (60 m) | 2+ | 2+ | 2 | 0.5 | 0.5 | 0.0 | 0.0 | 0.0 |
| Stinging (10 m) | 2 | 2 | 0.5 | 0 | 0 | 0 | 0 | 0 |
| BD-OD | 20.20 | 20.20 | 20.20 | 20.20 | 20.20 | 20.20 | 20.20 | 20.20 |
| BD-OS | 20.25 | 20.25 | 20.25 | 20.25 | 20.25 | 20.25 | 20.25 | 20.25 |
| BN-OD | 8 pt | 8 pt | 8 pt | 8 pt | 8 pt | 8 pt | 8 pt | 8 pt |
| BN-OS | 7 pt | 7 pt | 7 pt | 7 pt | 7 pt | 7 pt | 7 pt | 7 pt |
| BP-photopic | 3 mm | 3 mm | 3 mm | 3 mm | 3 mm | 3 mm | 3 mm | 3 mm |
| BP-Mesopic | 5 mm | 5 mm | 5 mm | 5 mm | 5 mm | 5 mm | 5 mm | 5 mm |
| Miosis start (m) | 15 | 15 | 15 | 15 | 15 | 15 | 15 | 15 |
| Miosis (OU) (1 hr) | 1.63 mm | 1.63 mm | 20-25 mm | 1.63 mm | 1.63 mm | 1.63 mm | 1.63 mm | 1.70 mm |
| Distance (OU) (20 m) | 20.20 | 20.20 | 20.20 | 20.20 | 20.20 | 20.20 | 20.20 | 20.20 |
| Distance (OD) (1 hr) | 20.15 + 2 | 20.15 + 2 | 20.20 | 20.15 + 2 | 20.15 + 2 | 20.15 + 2 | 20.15 + 2 | 20.15 + 2 |
| Distance (OS) (1 hr) | 20.15 + 2 | 20.15 + 2 | 20.20 | 20.15 + 2 | 20.15 + 2 | 20.15 + 2 | 20.15 + 2 | 20.15 + 2 |
| Disance (OU) (1 hr) | 20.10 − 3 | 20.10 − 3 | 20.15 | 20.10 − 3 | 20.10 − 3 | 20.10 − 3 | 20.10 − 3 | 20.10 − 3 |
| Next (OU) (20 m) | 4 pt | 4 pt | 4 pt | 4 pt | 4 pt | 4 pt | 4 pt | 4 pt |
| Time (hr) | 12.5 | 12.5 | 6.5 | 11 | 10 | 10 |  |  |

Abbreviations: (C) indicates corrected vision, (m) indicates minutes, (hr) indicates hour, mm indicates millimeters, BD indicates baseline distance vision; BN indicates baseline near vision, BP indicates baseline pupil size, OD indicates right eye; OS indicates left eye and OU indicates both eyes.

Abbreviations: (C) indicates corrected vision, (m) indicates minutes, (hr) indicates hour, mm indicates millimeters, BD indicates baseline distance vision; BN indicates baseline near vision, BP indicates baseline pupil size, OD indicates right eye; OS indicates left eye and OU indicates both eyes.

All percentages are w/v. "pt" reflects size of print materials, 4 being equivalent to 20/20 vision and 3 to 20/15 vision.

"Time" refers to duration of the effect.

As seen in Table 2 aceclidine at a concentration of at least 1.100 w/v was able to reduce the size of the pupil to 1.63 mm 1 hour after topical instillation resulting in corrected near and distance vision for at least 10 hours. Lowering of the concentration of aceclidine to 0.75% w/v (formula #3) reduced the miotic effect to 2.0-2.5 mm after 1 hour and vision correction lasted only 6.5 hours. The addition of 0.03% w/v brimonidine reduced redness of the eye (4 out of 4 without brimonidine, not shown) to 1.5 out of 4 within 30 minutes after topical instillation which was maintained for lation of formula #4. Upon a $3^{rd}$ topical instillation, at the end of the effective duration of formula #5, re-topical instillation of formula #5 again led to considerable brow ache. Once again, in formula #6, raising the concentration of tropicamide was able to overcome the brow ache. Additionally and unexpectedly, tropicamide, despite being a cycloplegic agent, had no effect on pupil miosis or vision correction. Surprisingly, the addition of tropicamide resulted in a prolonged duration of optimal pupil size constriction.

To determine the effect of brimonidine on pupil miosis, formula #7, was administered. Administration of formula #7 resulted in only a slight decrease in pupil miosis to 1.70 mm with identical distance and near vision improvement to that of formula #5. A 2-3+ conjunctival injection was noted.

All baseline vision data was based on vision corrected with distance contact lenses. Near vision was noted by subject as outstanding from 8 inches to the horizon at 1.5 hours after installation. A Marco Autorefractor with infrared camera and superimposed pupil calibration scale was used for all pupil size measurements. Once an image was selected it remained on screen allowing accurate calibration.

Example 3 Effect of Concentration of Aceclidine, Brimonidine, Guanfacine, Fadolmidine, Tropicamide and Additives

TABLE 3

Effect of concentration of aceclidine, brimonidine, guanfacine, fadolmidine, tropicamide and additives.

|  | AB2T | AB4T | AB6T | AB11T | AB12T | PROPH13 |
|---|---|---|---|---|---|---|
| Aceclidine | 1.55 | 1.55 | 1.55 | 1.55 | 1.85 | 1.55 |
| Brimonidine | 0.037 | 0.037 | 0.037 | 0.037 | | |
| Fadolmidine | | | | | | 0.037 |
| Guanfacine | | | | | 0.037 | |
| HPBCD | 5.5 | 5.5 | 5.5 | 5.5 | 5.5 | 5 |
| Tropicamide | 0.043 | 0.043 | 0.043 | 0.043 | 0.042 | 0.043 |
| CMC* | 0.075 | 0.075 | 0.075 | 0.075 | 0.075 | 0.075 |
| NaCl | 0.025 | 0.025 | 0.025 | 0.025 | 0.025 | 0.025 |
| BAK | 0.01 | 0.01 | 0.01 | 0.01 | 0.01 | 0.01 |
| Glycerin | 0.1 | | 0.1 | | | 0.1 |
| Poloxamer 188 | 0.1 | 0.05 | | | | |
| Polyoxyl 40 stearate | | 0.05 | | | | |
| pH | 6.5 | 7.5 | 7.5 | 7.5 | 7.0 | 7.5 |
| nasal congestion | 0 | 0 | 0 | 0 | 0 | 0 |
| stinging initial | 0.75 | 0 | 1.5 | 3.5 | 0 | 1.5 |
| stinging 3 min | 0.5 | 0 | 0 | wash out | 0 | 0 |
| redness initial | 0 | 0 | 1 | D/C | 1 | 1 |
| redness 15 min | 0 | 0 | 0 | D/C | 0 | 0 |
| whitening | 0 | 0 | 0 | D/C | 1.5 | 1.5 |
| pain | 0 | 0 | 0 | D/C | 0 | 0 |
| vision near | 20.30 | 20.15 | 20.15 | D/C | 20.15 | 20.15 |
| vision distance | 20.20 | 20.20 | 20.20 | D/C | 20.20 | 20.20 |
| onset (min) | 20 | 12 | 16 | D/C | 12 | 16 |
| duration (hrs) | 5.5 | 7.5 | 7.5 | D/C | 7.5 | 7.5 |
| color | clear | yellow | yellow | yellow | yellow | yellow |
| OVERALL | 2.5 | 3.9 | 3.8 | 0 | 4 | 3.9 |

*1% = 2,500 cps
All percentages are w/v. Scores for nasal congestion, stinging initial, stinging, 3 min, redness initial, redness 15 min, whitening, pain and overall are out of 4.
"pt" reflects size of print materials, 4 being equivalent to 20/20 vision and 3 to 20/15 vision.
Baseline vision was 20.20 both eyes for distance; 20.70 right eye unaided for near; 20.80 left eye for near (best @ 16").
D/C stands for discontinued after eye washing due to intolerable stinging.

Aceclidine at a concentration of 1.55% w/v was able to reduce the size of the pupil to about 1.63 mm 30 minutes after topical instillation resulting in corrected near and distance vision to 20.20 or better for at least 6 hours, with noticeable affect lasting about 7.5 hours as seen in Table 3. Lowering of the concentration of aceclidine to 1.25% w/v (not shown) resulted in useful near vision improvement to about 20.25-20.30, but not as effective as at the higher dose range alkaline pH resulted in quicker onset, longer duration, and greater effect. The addition of 0.037% w/v brimonidine reduced redness of the eye (4 out of 4 without brimonidine, not shown) to baseline within 15 minutes after topical instillation which was maintained for the about the entire time vision was corrected. Adding glycerin 0.10% w/v noticeably reduced stinging. Adding instead poloxamer 188 0.05% w/v and polyoxyl 40 stearate 0.05% w/v however reduced initial stinging further but was more viscous. The combination of glycerin 0.1% w/v, poloxamer 188 0.1% w/v at a pH of 6.5 was noticeably reduced in onset, duration, comfort and effectiveness. AB11T did not include glycerin, poloxamer 188, or polyoxyl 40 stearate, which resulted in substantial stinging and discontinuation of the experiment with eye flush irrigation immediately after topical instillation. Substitution of guanfacine 0.037% w/v in AB12T for brimonidine resulted in minimal initial redness with prolonged redness reduction and some degree of whitening, and appeared to provide overall the best cosmesis though requiring slightly higher aceclidine concentration for optimal effect.

All baseline vision data was based on vision corrected with distance contact lenses. Near vision was noted by subject as outstanding from 8 to 10 inches to the horizon at 30 minutes after installation for AB4T and AB6T.

AB4T and AB6T were repeated both monocularly and binocularly. Substantial improvement in depth perception, near point acuity to 3 pt (20.15), and near point distance (8", 20.20) was noted when both eyes were treated vs. monocular treatment. Monocular treatment resulted in worsening of vision with both eyes open versus testing only the treated eye.

Example 4 Effect of Concentration of Aceclidine, Brimonidine, Tropicamide, and Additives

TABLE 4

Effect of concentration of aceclidine, brimonidine, tropicamide, and additives.

|  | #8 | #9 | #10 | #11 | #12 | #13 | #14 | #15 | #16 | #17 | #18 | #19 | #20 | #21 |
|---|---|---|---|---|---|---|---|---|---|---|---|---|---|---|
| Aceclidine | 1.61% | 1.61% | 1.61% | 1.61% | 1.61% | 1.53% | 1.53% | 1.53% | 1.53% | 1.53% | 1.53% | 1.45% | 1.65% | 1.75% |
| Tropicamide | 0.042% | 0.042% | 0.042% | 0.042% | 0.042% | 0.044% | 0.044% | 0.044% | 0.044% | 0.044% | 0.044% | 0.042% | 0.044% | 0.035% |
| Brimonidine | 0.042% | 0.042% | 0.042% | 0.042% | | | 0.042% | 0.042% | 0.042% | | 0.042% | 0.042% | 0.042% | 0.042% |
| CMC | 0.75% | 0.75% | 0.80% | 0.83% | 0.75% | 0.75% | 0.75% | 0.80% | 0.80% | 0.80% | 0.80% | 0.35% | 0.75% | 0.75% |
| NaCl | 0.25% | 0.25% | 0.50% | 0.50% | 0.25% | 0.50% | 0.50% | 0.50% | 0.75% | 0.75% | 1.00% | 0.25% | 0.25% | 0.25% |
| BAK | 0.01% | 0.01% | 0.01% | 0.01% | 0.01% | 0.01% | 0.01% | 0.01% | 0.01% | 0.01% | 0.01% | 0.01% | 0.01% | 0.01% |
| pH | 7.00 | 7.00 | 7.00 | 7.00 | 8.00 | 7.00 | 7.00 | 7.00 | 7.00 | 8.00 | 7.00 | 7.00 | 7.00 | 8.00 |
| phosphate buffer | 5 mM | | 5 mM | 5 mM | 6 mM | 5 mM | 5 mM | 5 mM | 5 mM | 5 mM | 5 mM | 5 mM | 5 mM | 6 mM |
| borate buffer | | 5 mM | | | | | | | | | | | | |
| Onset (min) | 15 | 13 | 15 | 15 | 13 | 15 | 13 | 13 | 15 | 15 | 13 | 15 | 15 | 13 |
| Duration (hrs) | 7 | 7 | 10-12 | 10-12 | 7 | 9 | 7 | 10-12 | 9 | 9 | 7 | 7 | 7 | 7 |
| Pupil range (mm) | 1.5-1.7 | 1.5-1.7 | 1.5-1.7 | 1.5-1.7 | 3.5-1.7 | 1.8-2.0 | 1.8-2.0 | 1.8-2.0 | 18-2.0 | 1.8-2.0 | 1.8-2.0 | 1.8-2.1 | 1.8-2.1 | 1.8-2.2 |
| Dimming 0-4 | 1.5 | 1.5 | 1.5 | 1.5 | 1.5 | 0.5 | 0.5 | 0.5 | 0.5 | 0.3 | 0.5 | 0.5 | 0.5 | 0.3 |

TABLE 4-continued

Effect of concentration of aceclidine, brimonidine, tropicamide, and additives.

| | #8 | #9 | #10 | #11 | #12 | #13 | #14 | #15 | #16 | #17 | #18 | #19 | #20 | #21 |
|---|---|---|---|---|---|---|---|---|---|---|---|---|---|---|
| Sting 0-4 | 1 | 1 | 1 | 1 | 1 | 1 | 1 | 1 | 1 | 1 | 1 | 1 | 1 | 1 |
| Ache 0-4 | 0.25 | 0.25 | 0.25 | 0.25 | 0.25 | 0.00 | 0.00 | 0.00 | 0.00 | 0.00 | 0.00 | 0.00 | 0.25 | 0.00 |
| Redness 0-4 | 0.3 | 0.5 | 0.3 | 0.5 | 1.5 | 1.0 | 0.3 | 0.5 | 0.3 | 1.0 | 0.3 | 0.5 | 0.3 | 0.5 |
| Other | watery | watery | sl thicker | sl residue | watery | watery | watery | sl thicker | sl thicker | sl thicker | thicker | watery | watery | watery |
| Overall 0-5 | 3.5 | 3.5 | 4 | 4 | 2.5 | 4.5 | 4.75 | 3 | 5 | 3 | 4 | 4 | 4 | 4 |

As seen in Table 4, formulas #8-9, an increase in brimonidine to 0.420% w/v resulted in redness reduction to 0.5, while 0.750% w/v CMC resulted in a watery consistency. Unexpectedly, increasing CMC from 0.7500 w/v to a range of 0.800% w/v to 0.87 w/v and increasing NaCl from 0.25% w/v to 0.75% w/v in formulas #10-11 resulted in a thicker consistency and an increased residence time from 7 hours to 10-12 hours and decreased the amount of drug that drained into the nasolacrimal duct. This decreased drug delivery to the nasal passages results in less nasal congestion.

In formulas #13-18 a decrease in the amount of aceclidine from 1.61% to 1.53% w/v resulted in a pupil size range from 1.8-2.0 mm. Dimming as a result of the restriction of the pupil decreased linearly from 1.5 to 0.5 with the decreased amount of aceclidine. Specifically, the 1.8 to 2.0 mm pupil created 41% more light than the 1.5 to 1.7 mm pupil. Surprisingly, the 1.8 to 2.0 mm pupil had a near depth increase of 1.75 D. This is only a 0.25 D loss from the beneficial 2.00 D seen with the 1.5-1.7 mm range. Thus, the 1.80 to 2.0 mm range produces 41% more light while still allowing the full benefit of increased near vision in individuals under 60 years of age; whereas, individuals 60 years of age and over still experience total computer benefit and some increased near benefit.

The increase in tropicamide concentration from 0.042% w/v (formulas #8-#11) to 0.044% w/v (formulas #13-#18) resulted in a decrease in ache to negligible amounts. The amount of ache may also be correlated with the age of the individual. For those individuals under the age of 45, an increase of tropicamide concentration to a range from 0.046% to 0.060 w/v may be preferred.

Further, Table 4 shows an unexpected result seen in formulas #13 and #17 where the increase of NaCl from 0.25% w/v to a range of 0.50 to 0.75% w/v resulted in an acceptable redness score of only 1.0 even without the addition of the redness reducing agent brimonidine.

Formulas #15, #16 and #17 each result in an overall maximum rating of 5 by combining the benefits of: (1) reduced aceclidine concentrations to improve the amount of light produced without significantly affecting the near vision benefits seen in formulas #8-#12; (2) increased NaCl concentrations resulting in a further reduction in redness even in the absence of brimonidine; and (3) increased CMC concentrations resulting in longer residency time on the eye.

Formula #19 is an excellent alternative for the minority of individuals that are high responders to formulas #15-#17 and get noticeable dimming with 1.53% w/v aceclidine. Formula #20 is an excellent alternative for the minority of individuals that are low responders to formula #19. Lastly, Formula #21 is an excellent alternative for the minority of individuals that are low responders and get poor pupil response with Formula #20.

Example 5 Comparison of Effects of Polyoxyl 40 Stearate, HPβCD and Poloxamer 407

TABLE 5

Comparison of Effects of Polyoxyl 40 Stearate, HPβCD and Poloxamer 407.

| | #22 | #23 | #24 |
|---|---|---|---|
| Aceclidine | 1.45% | 1.45% | 1.45% |
| Tropicamide | 0.044% | 0.044% | 0.044% |
| Brimonidine | 0.040% | 0.040% | 0.040% |
| Polyoxyl 40 Stearate | 5.5% | | |
| HPβCD | | 5.5% | |
| Poloxamer 407 | | | 5.5% |
| CMC | 0.80% | 0.80% | 0.80% |
| NaCl | 0.037% | 0.037% | 0.037% |
| EDTA | 0.015% | 0.015% | 0.015% |
| BAK | 0.007% | 0.007% | 0.007% |
| pH | 7.00 | 7.00 | 7.00 |
| phosphate buffer | 5 mM | 5 mM | 5 mmM |
| Nasal Congestion | 0.00 | 0.50 | 1.50 |
| Stinging | 0.25 | 0.25 | 0.25 |
| Wetting | 4.00 | 4.00 | 4.00 |
| Redness | 0.25 | 0.50 | 0.50 |
| Visual Blur (<15 sec) | 0.50 | 0.50 | 1.50 |
| Duration | 6-8 hrs | 6-8 hrs | 6-8 hrs |
| Overall 0-4 | 4.00 | 4.00 | 4.00 |

Clinical Protocol 20 presbyopic patients with full distance correction were each given one of the above formulas (#22-#23). All patients received pre- and post-drop distance and near acuity measurement, Zeiss Visante® (Visante is a registered trademark of Carl Zeiss Meditec AG) optical adherence tomography, axial length and contrast acuity testing (i.e. Colenbrander-Michelson 10% Lum target) with the following results:
  all patient achieved a miotic pupil of 1.5 to 2.20 mm;
  no patient experienced ciliary ache, ciliary spasm, or induced accommodation;
  all patients achieved 20/30+ visual acuity or better at 14" and were very satisfied with their high contrast near vision results and there was no significant complaint of burning or aching;
  the duration of effect lasted 6-8 hrs in all cases;
  binocular vision afforded all patients 1-1.5 additional lines of near acuity over monocular testing;
  the last 10 patients were tested at 20" (i.e. computer distance, cell phone distance) and all achieved 20/25 or better near visual acuity;
  moderately hyperopic (approx. +2.25 sphere) uncorrected presbyopes were very satisfied with distance visual acuity that improved to a 20/25 or better level at distance and near vision in the 20/30 range; and
  uncorrected distance acuity was often improved for those patients who chose not to routinely correct a small refractive error.

As seen in Table 5, the use of polyoxyl 40 stearate provides the most comfortable aceclidine formulation with the least amount of visual blur and redness. To achieve similar results to that of formula #22, formula #23 requires 10-15% higher concentrations of the non-ionic surfactant and formula #24 requires 15-20% higher concentrations of the non-ionic surfactant. HPβCD induced a color change over time, possibly indicative of oxidation. Captisol® (sulfobutylether β-cyclodextrin) was substituted with similar findings.

Example 6 Modulation of Aceclidine Concentrations in a Preferred Embodiment

Preferred Embodiment

Aceclidine 1.35%-1.55% w/v;
Polyoxyl 40 stearate 5.5% w/v;
NaCl 0.037% w/v;
a viscosity agent, preferably CMC 0.80% w/v or an amount of Carbopol® 934 or 940 sufficient to achieve a viscosity of from about 5 to about 35 cps upon topical instillation, such as Carbopol® 940 at a concentration from about 0.09% to about 1.0% w/v;
BAK 0.015% w/v; and
optionally, a phosphate, citrate, citrophosphate, or acetate buffer from about 3 to about 10 mM,
wherein the pH is from about 4.75 to about 6.0.
For 1.35% w/v aceclidine—
Stinging on topical instillation 0.25/4.0 (lasting about 2-5 seconds);
Induced redness at 10 minutes: 1.0 to 1.5/4.0;
Induced redness at 30 minutes: 0.0 to 0.25/4.0;
Comfort: very high.
Wetting: very high, the eye maintaining sensation of improved wetting for most of a 24 hour period after a single topical instillation.
Depth of Focus distance: excellent.
Depth of Focus near: excellent.

In testing the above formulations on several subjects it was discovered that there is a slight range in clinical effect depending on the concentration of aceclidine, where 1.35%-1.55% w/v aceclidine is preferred, but for which 1.35% w/v and 1.45% w/v confer the desired benefits on most subjects.

Further, it is discovered that the clinical effect of 1.35% w/v aceclidine can be improved when instilled as follows:

1) baseline effect: 1 drop to each eye.
2) enhanced effect: 2 drops to each eye.
3) greater effect: after 2) above repeat 1) above.
4) maximum effect: after 2) above repeat 2) above.

Example 7 Use of a Preferred Embodiment to Prolong Contact Lens Wear

Preferred Embodiment

Aceclidine 1.45% w/v;
Polyoxyl 40 stearate 5.5% w/v;
NaCl 0.037% w/v;
a viscosity agent, preferably CMC 0.80% w/v or an amount of Carbopol® 934 or 940 sufficient to achieve a viscosity of from about 5 to about 35 cps upon topical instillation, such as Carbopol® 940 at a concentration from about 0.09% to about 1.0% w/v;
BAK 0.02% w/v; and
optionally, a phosphate, citrate, citrophosphate, or acetate buffer from about 3 to about 10 mM,
wherein the pH is from about 4.75 to about 6.0.

As a baseline, the subject, who normally wore extended wear lenses (Air Optix®; Air Optix is a registered trademark of Novartis AG) for daily wear only, slept in these lenses overnight. On arising each morning the subject's vision was blurred and the contact lenses required removal and cleaning of film and deposits that had formed overnight. Average vision on arising at distance: 20.60; average vision at near on a Michelson contrast acuity chart: 20.80.

Then, for seven consecutive days the above formulation was instilled between 7 am and 10 am each day as a single dose. Subject wore the Air Optix® lenses throughout each day and slept in the lenses overnight. Upon arising each morning the subject's vision at distance: 20.20+; vision at near 20.40 unaided (consistent with subject's baseline presbyopia when the subject did not wear the lenses overnight and instead inserted the lenses upon arising).

Example 8 Comparison of Effects of Polyoxyl 40 Stearate and Captisol® (Sulfobutylether β-Cyclodextrin

TABLE 6

Comparison of Effects of Polyoxyl 40 Stearate and Captisol ® (sulfobutylether β-cyclodextrin).

| | #25 | #26 | #27 | #28 | #29 | #30 | #31 | #32 | #33 |
|---|---|---|---|---|---|---|---|---|---|
| Aceclidine | 1.35% | 1.35% | 1.35% | 1.35% | 1.35% | 1.35% | 1.35% | 1.35% | 1.35% |
| Tropicamide | 0.044% | 0.044% | 0.044% | 0.044% | 0.044% | 0.044% | 0.044% | 0.044 | 0.044% |
| Polyoxyl 40 stearate | 5.5% | 5.5% | 5.5% | 5.5% | 5.5% | 5.5% | 5.5% | | |
| Captisol ® | | | | | | | | 5.5% | 5.5% |
| Cocamidopropyl betaine | | | | | | | 0.10% | | |
| EDTA | | | 0.015% | 0.015% | 0.005% | 0.005% | 0.005% | 0.005% | 0.015% |
| CMC 1% = 2,500 cps | 0.80% | 0.80% | 0.80% | 0.80% | 0.80% | 0.80% | 0.80% | 0.80% | 0.80% |
| NaCl | 0.037% | 0.037% | 0.037% | 0.037% | 0.037% | 0.037% | 0.037% | 0.037% | 0.037% |
| Mannitol | | | | | | | | 4% | 4% |
| BAK | 0.007% | 0.007% | 0.007% | 0.007% | 0.007% | 0.007% | 0.007% | 0.007% | 0.007% |
| Boate buffer (mM) | 4 | | 4 | | 4 | 4 | 4 | 4 | 4 |
| Phosphate buffer (mM) | | 4 | | 4 | | | | | |
| pH | 7 | 7 | 7 | 7 | 7 | 7 | 7 | 7 | 7 |
| Redness, 10 min | 1.25 | 1.25 | 2 | 2 | 1.75 | 1.75 | 0 | 0 | 0 |
| Redness, 30 min | 0 | 0 | 1.5 | 1.5 | 1.25 | 1.25 | 0 | 0 | 0 |

TABLE 6-continued

Comparison of Effects of Polyoxyl 40 Stearate and Captisol ® (sulfobutylether β-cyclodextrin).

|  | #25 | #26 | #27 | #28 | #29 | #30 | #31 | #32 | #33 |
|---|---|---|---|---|---|---|---|---|---|
| Pupil, 30 min (mm) | <2 | <2 | <2 | <2 | <2 | <2 | <2 | <2 | <2 |
| Blur on instill (sec) | 10 | 10 | 10 | 10 | 10 | 10 | 10 | 10 | 10 |
| Ache | 0 | 0 | 0 | 0 |  | 0 | 1 | 0 | 0 |
| Rating | 4.00 | 4.00 | 2.00 | 2.00 | 2.50 | 2.50 | 1.00 | 5.00 | TBD |

As seen in Table 6, when using polyoxyl 40 stearate as the surfactant the exclusion of EDTA results in reduced redness and best overall rating among polyoxyl 40 stearate compositions (Formulas #25 and #26). The addition of cocamidopropyl betaine ("CAPB") further reduces redness however results in significant ache (Formula #31). Replacing polyoxyl 40 stearate with Captisol® (sulfobutylether β-cyclodextrin) and adding mannitol achieves similar results in redness reduction as the addition of CAPB to polyoxyl 40 stearate but without the attendant ache resulting in the highest overall rating among aceclidine compositions (Formula #32). After several weeks formulations with Captisol® (sulfobutylether β-cyclodextrin) had an orange hue, possibly indicative of oxidation.

Example 9 Preferred Cold Chain Composition

Composition
  aceclidine at a concentration of about 1.40%-1.80% w/v; and
  tropicamide at about 0.4200 w/v;
  polyoxyl 40 stearate at about 5.500 w/v;
  mannitol at a concentration of about 2.5% to 4.5% w/v;
  carbomer 940 at a concentration of about 0.09% to about 2.0% w/v;
  optionally, a preservative such as BAK at a concentration of about 0.2% w/v;
  optionally citrate at a concentration of about 0.1%;
  optionally with acetate or phosphate buffer at 2-100 mM, more preferably 3-5 mM
  wherein said composition has a pH of about 4.50 to about 5.0; and preferably, about 4.75 to about 5.0; and
  wherein w/v denotes weight by volume A composition as described above was administered to a 62 year old subject. It resulted in pupils of 1.8-1.9 mm ou, 20.20+ reading vision, and 20.20+ distance vision; whereas without carbomer 940 reduced effectiveness resulted at 2.5% mannitol, and no near vision effect resulted at 4.0% mannitol. No ciliary spasm or loss of distance vision resulted. Onset was within about 15 minutes. Transient redness of about 1+/out of 4 was noted for about 20 minutes without alpha agonist vasoconstrictor. The presence or absence of BAK had no clinical effect, and was used to provide an optional preservative.

Example 10 Stabile Aceclidine Formulations

Composition Tested:
  aceclidine at a concentration of about 1.50% w/v;
  tropicamide at a concentration of about 0.042% w/v;
  polyoxyl 40 stearate at a concentration of about 5.5% w/v;
  mannitol at a concentration of about 2.5% w/v;
  citrate at a concentration of about 3 mM;
  wherein said composition has a pH of about 4.75.

20 samples of the above composition were divided evenly and stored at 25° C. and 4° C. Prior to storage, initial concentrations of aceclidine were measured using high-pass liquid chromatography ("HPLC"). The amount of aceclidine in each solution was calculated by the area under the principal peak compared to a reference solution of aceclidine. Samples were then subject to storage for 3 months. Aceclidine measurements were taken at 1, 2 and 3 months. Results of the stability test are shown in Table 7.

TABLE 7

Stability of Aceclidine in Cold Chain Storage

|  | 25° C. | 4° C. |
|---|---|---|
| Initial | 100% | 100% |
| 1 month | 92% | 93% |
| 2 months | 75% | 92% |
| 3 months | 50% | 88% |

As seen in Table 7 "cold chain storage" or storage of the aceclidine composition at from 2° C. to 8° C. resulted in a significant increase in stability of aceclidine at all 3 time points.

Example 11 Use of Compositions Containing Little or No Cycloplegic Agent

Aceclidine alone causes incidence migraine-like severe ciliary spasm (brow ache) and myopic blur. These effects are inversely correlated to age with subjects age 40 reporting the highest incidence and subject age 60+ reporting the lowest incidence. The addition of a cycloplegic agent reduces ciliary spasms and attendant brow ache, migranious headache, squeezing pressure around eyes or other symptoms of ciliary spasms. The addition of the cycloplegic agent, surprisingly, does not reduce the myopic effect of aceclidine. The addition of 2.5% w/v mannitol however does reduce the myopic effect of aceclidine. Increasing the aceclidine concentration overcomes this reduction in myopic effect seen with the addition of mannitol. Surprisingly, however, the increase in aceclidine is not coincident with an increase in ciliary spasm. Even more surprising, the concentration of the cycloplegic agent can be reduced or even eliminated in the presence of mannitol without an increase in ciliary spasm. Thus, combining a higher concentration of aceclidine with little to no cycloplegic agent in the presence of mannitol results in an improvement of near vision acuity without attendant side effects on par with lower concentrations of aceclidine and higher concentrations of the cycloplegic agent in the absence of a cycloplegic agent.

Further and unexpectedly, the addition of a nonionic surfactant increases both the quantitative measure of near vision improvement and the duration. This effect is concentration sensitive. In a preferred embodiment the non-ionic surfactant is at least 1%, preferably at least 2%, more preferably from about 1% to about 5%, and most preferably about 5%. For example, polysorbate 80 or polyoxyl 40 stearate at a concentration from about 1% to about 5% w/v results in about 1.5 to about 2.0 lines of improvement and a duration from about 4 to about 5 hours.

Not to be held to particular theory, the increase in concentration of a surfactant may crowd the surface of the cornea, and at an optimal concentration this crowding result in small and probably nanometer diameters, which given the dual polarity of surfactants, where nonionic are most preferred, enhances corneal absorption of the entrapped highly polar aceclidine molecules.

Figure 2:
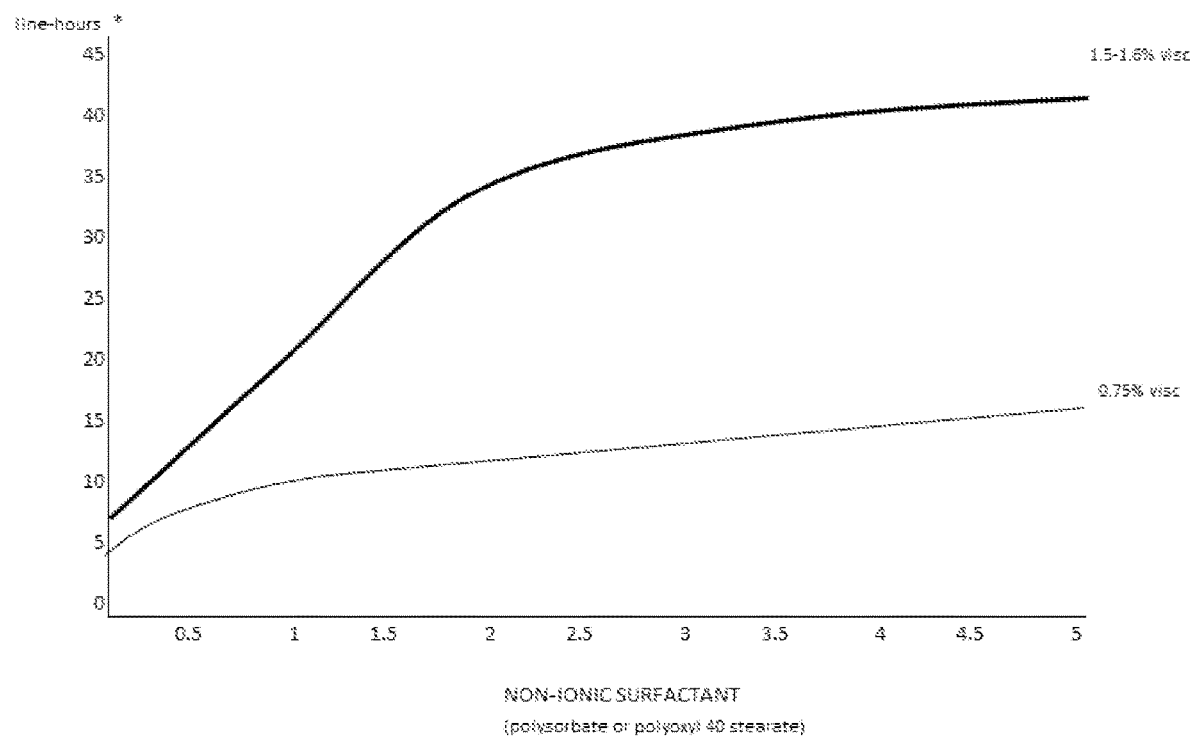
FIG. 2 is a graphical representation of the effects of addition of non-ionic surfactants and viscosity agents on near vision acuity and duration of effect. Line-Hours denotes lines improved times duration of effect.

The further addition of a viscosity agent by itself does not enhance duration. Surprisingly, the addition of a viscosity agent in a formulation with optimal ratios of aceclidine, tropicamide and a non-ionic surfactant dramatically improves duration. For example, a formulation of the present invention comprising 1.75% aceclidine, 2.5% mannitol, 0.01% tropicamide, 5% polysorbate 80 improves near vision in a presbyopic patient by up to 3 lines of vision acuity for about 4 to about 5 hours. The addition of 1.4% CMC further increases the near vision improvement to from about 7 to about 10 hours. Not to be held to a particular theory, a threshold above the critical micellar threshold greatly enhances permeation through the cornea by reducing micelle size from micrometers to nanometers. See FIG. 2.

Examples of compositions containing little or no cycloplegic agent are shown in Table 8 below.

TABLE 8

Compositions containing little or no cycloplegic agent

| | #L1 | #L2 | #L3 | #L4 | #L5 | #L6 | #L7 | #L8 | #L9 | #L10 |
|---|---|---|---|---|---|---|---|---|---|---|
| Aceclidine | 1.75% | 1.75% | 1.75% | 1.75% | 1.75% | 1.75% | 1.75% | 1.75% | 1.75% | 1.75% |
| Tropicamide | 0.02% | 0.02% | 0.02% | 0.02% | 0.02% | — | — | — | — | — |
| Mannitol | 2.5% | 2.5% | 2.5% | 2.5% | 2.5% | 2.5% | 2.5% | 2.5% | 2.5% | 2.5% |
| Polysorbate 80 | 0.75% | 0.25% | 0.25% | 0.1% | 0.1% | 0.50%# | 0.25% | 0.25% | 0.1% | 0.1% |
| Carbopol ® 940 or CMC | 0.95% | 0.95% | 0.95% | 0.9% | 0.95% | 0.95%* | 0.95%* | 0.95%* | 0.9%* | 0.95%* |
| Glycerine | | | | | | | | | | |
| Phosphate buffer | 3 mM | — | 3 mM | 3 mM | 3 mM | 3 mM | — | 3 mM | 3mM | 3mM |
| NaCl | 0.5% | 0.1% | 0.05% | — | 0.1% | 0.5%* | 0.1% | 0.05% | — | 0.1% |
| Boric acid | — | 0.12% | 0.2% | 0.2% | 0.12% | — | 0.12% | 0.2% | 0.2% | 0.12% |
| BAK | 0.015% | 0.01% | 0.01% | 0.05% | 0.01% | 0.015% | 0.01% | 0.01% | 0.05% | 0.01% |
| pH | 5.0 | 5.0 | 5.0 | 5.0 | 5.0 | 5.0 | 5.0 | 5.0 | 5.0 | 5.0 |

| | #L11 | #L12 | #L13 | #L14 | #L15 | #L16 | #L17 | #L18 | #L19 | #L20 | #L21 |
|---|---|---|---|---|---|---|---|---|---|---|---|
| Aceclidine | 1.65% | 1.65% | 1.75% | 1.75% | 1.65% | 1.75% | 1.75% | 1.75% | 1.75% | 1.75% | 1.75% |
| Tropicamide | 0.01% | — | — | 0.025% | 0.025% | 0.025% | 0.025% | 0.025% | 0.025% | 0.015% | 0.015% |
| Mannitol | 2.5% | 2.5% | 2.5% | 2.5% | 2.5% | 2.5% | 2.5% | 2.5% | 2.5% | 2.5% | 2.5% |
| Polysorbate 80 | 2% | 2% | 1% | 0.10% | 2.50% | 2.50% | 3.00% | 2.50% | 2.50% | 2.50% | 2.50% |
| Carbopol ® 940 or CMC | 0.75% | 0.75% | 0.75% | 0.75% | 0.75% | 0.75% | 0.75% | 1.50% | 0.75% | 0.75% | 0.75% |
| Glycerine | 0.10% | 0.10% | 0.10% | 0.10% | 0.10% | 0.10% | 0.10% | 0.10% | 0.20% | 0.20% | 0.20% |
| Phosphate buffer | 3 mM | 3 mM | 3 mM | 3 mM | 3 mM | 3 mM | 3 mM | 3 mM | 3 mM | 3 mM | 3 mM |
| NaCl | — | — | — | — | — | — | — | — | — | — | — |
| Boric acid | — | — | — | — | — | — | — | — | — | — | — |
| BAK | 0.01% | 0.01% | 0.01% | 0.01% | 0.015% | 0.015% | 0.015% | 0.015% | 0.015% | 0.015% | 0.015% |

| | #L22 | #L23 | #L24 | #L25 | #L26 | #L27 | #L28 | #L29 | #L30 | #L31 | #L32 |
|---|---|---|---|---|---|---|---|---|---|---|---|
| Aceclidine | 1.65% | 1.75% | 1.75% | 1.75% | 1.75% | 1.65% | 1.75% | 1.75% | 1.75% | 1.75% | 1.75% |
| Tropicamide | 0.025% | 0.275% | 0.020% | 0.015% | 0.027% | 0.0275% | 0.0275% | 0.0275% | 0.025% | 0.022% | 0.0175% |
| Mannitol | 2.5% | 2.5% | 2.5% | 2.5% | 2.5% | 2.5% | 2.5% | 2.5% | 2.5% | 2.5% | 2.5% |
| Polysorbate 80 | 5% | 5% | 5% | 5% | 5% | 5% | 5% | 5% | 5% | 5% | 5% |
| Carbopol ® 940 or CMC | 1.25% | 1.45% | 1.45% | 1.45% | 1.45% | 1.25% | 1.40% | 1.40% | 1.50% | 1.40% | 1.50% |
| Glycerine | | | | | | | | | | | |
| Phosphate buffer | 3 mM | 3 mM | 3 mM | 3 mM | 3 mM | 3 mM | 3 mM | 3 mM | 3 mM | 3 mM | 3 mM |
| NaCl | — | — | — | — | — | — | — | — | — | — | — |
| Boric acid | — | — | — | — | — | — | — | — | — | — | — |
| BAK | 0.01% | 0.01% | 0.01% | 0.01% | 0.01% | 0.01% | 0.01% | 0.01% | 0.01% | 0.01% | 0.01% |
| pH | 5.0 | 5.0 | 5.0 | 5.0 | 6.0 | 5.0 | 5.0 | 5.0 | 5.0 | 5.0 | 6.0 |
| Pupil Size (mm) | | | | | | | | | | | |
| Reading vs. Baseline 40 cm | 3+ | 3+ | 3+ | 3+ | 3+ | 3+ | 3+ | 3+ | | | 3+ |
| Duration (hours) | 7 | 10+ | 10+ | 10+ | 10+ | 7.0 | 10+ | 10+ | | | 10+ |
| Ciliary Spasms | 0.0 | tr | 0.5 | 1.0 | 1.0 | 0.0 | tr | 0.5 | | 1.0 | 1.0 |

TABLE 8-continued

Compositions containing little or no cycloplegic agent

| | | | | | | | | | | | |
|---|---|---|---|---|---|---|---|---|---|---|---|
| Stinging | 0.5 | 0.5 | 0.5 | 0.5 | 0.5 | 0.5 | 0.5 | 0.5 | | | 0.5 |
| Blur (min) | 1 | 1 | 1 | 1 | 1 | 1 | 1 | 1 | | | 1 |
| Distance Blur | | | | | | | | | | | |
| Onset (min) | 20 | 20 | 20 | 20 | 20 | 20 | 20 | 20 | | | 20 |
| Redness 1 hr (0-4) | 0.5 | 0.5 | 0.5 | 0.5 | 0.5 | 0.5 | 0.5 | 0.5 | | | 0.5 |
| Redness 4 hr (0-4) | | | | | | | | | | | |
| Overall Comfort | sl sticky | sl sticky | sl sticky | sl sticky | sl sticky | sl sticky | sl sticky | sl sticky | | | sl sticky |
| Osmolarity | | | | | | | | | | | |
| Efficacy index: read*dur | | | | | | | | | | | |
| OVERALL (1-5) | best | best | best | best | best | best | best | best | | | best |

| | #L33 | #L34 | #L35 | #L36 | #L37 | #L38 | #L47 | #L48 | #L49 | #L50 | #L51 |
|---|---|---|---|---|---|---|---|---|---|---|---|
| Aceclidine | 1.75% | 1.40% | 1.40% | 1.25% | 1.45% | 1.45% | 1.45% | 1.55% | 1.65% | 1.75% | 1.65% |
| Tropicamide | — | — | — | — | — | 0.0200% | — | 0.0200% | 0.0300% | 0.0300% | 0.0200% |
| Brimonidine | — | — | — | — | — | — | — | — | — | — | — |
| Mannitol | — | — | — | — | — | — | 2.5% | 4.0% | 2.5% | 2.5% | 2.5% |
| Polysorbate 80 | — | — | — | — | — | — | — | — | — | 5.00% | — |
| Polyoxyl 40 Stearate | — | — | — | — | 5.5% | 5.5% | 5.5% | 5.5% | 5.5% | — | 5.5% |
| Citrate | 0.10% | 0.10% | 0.10% | 0.10% | 0.10% | 0.10% | 0.10% | 0.10% | 0.10% | — | 0.10% |
| Glycerine | — | 0.10% | 0.10% | 0.10% | 0.10% | 0.10% | 0.10% | 0.10% | 0.10% | 0.10% | 0.10% |
| CMC | — | 1.45% | 0.75% | — | 0.85% | 0.75% | 0.75% | 0.75% | 0.75% | 0.75% | 0.75% |
| HPMC | — | — | — | — | — | — | — | — | — | — | — |
| Carbopol ® 940 | — | — | — | — | — | — | — | — | — | — | — |
| NaCl | 0.75% | 0.75% | 0.50% | 0.50% | 0.50% | 0.50% | 0.50% | 0.50% | 0.50% | 0.50% | 0.00% |
| Boric Acid | — | — | — | — | — | — | — | — | — | — | — |
| Postassium Borate | — | — | — | — | — | — | — | — | — | — | — |
| Phosphate buffer | 3 | 3 | 3 | 3 | 3 | 3 | 3 | 3 | 3 | 3 | 3 |
| Acetate | — | — | — | — | — | — | — | — | — | — | — |
| pH | 5.0 | 5.0 | 5.0 | 5.0 | 5.0 | 5.0 | 5.0 | 5.0 | 5.25 | 5.0 | 5.0 |
| BAK | 0.015% | 0.015% | 0.015% | 0.015% | 0.015% | 0.015% | 0.015% | 0.015% | 0.015% | 0.015% | 0.015% |
| Pupil Size (mm) | | | | | | | | | | | |
| Reading vs. Baseline 40 cm | 3 | 3.25 | 3 | 2 | 3 | 2.5 | 1.5 | 0.5 | 1.5 | 1.5 | 1 |
| Duration (hours) | 4 | 7 | 4.5 | | 6.5 | 6 | 3 | 2 | 4 | 4 | 2 |
| Ciliary Spasms | 4 | 4 | 3 | 2 | 3 | 2 | 0.5 | 0.5 | 0.5 | 0.5 | 0.5 |
| Stinging | 1.0 | | 1.0 | | 1.0 | 1.0 | 1 | 1 | 0.5 | 1 | 1 |
| Blur (min) | | | | | | | | | | | |
| Distance blur | none | none | none | none | none | none | none | none | none | none | none |
| Onset (min) | 20-11 | 20-12 | 20-13 | 20-14 | 20-15 | 20-16 | 20-25 | 20-25 | 20-25 | 20-25 | 20-25 |
| Redness 1hr (0-4) | 2.0 | | 1.5 | | 0.5 | 0.5 | 0.5 | 0.5 | 0.5 | 0.5 | 0.5 |
| Redness 4hr (0-4) | | | | | | | | | | | |
| Overall comfort | poor | poor | poor | fair | poor | poor | good | good | good | good | good |
| Osmolarity | hi | hi | hi | hi | hi | hi | hi | hi | hi | hi | hi |
| Efficacy index: read*dur | 12 | 23 | 14 | 0 | 20 | 15 | 5 | 1 | 6 | 6 | 2 |
| OVERALL (1-5) | * | ** ½ | * | — | * | ** | *** | * | * | * | * |

| | #L52 | #L53 | #L54 | #L55 | #L56 | #L57 | #L58 | #L59 | #L60 | #L61 | #L62 |
|---|---|---|---|---|---|---|---|---|---|---|---|
| Aceclidine | 1.65% | 1.65% | 1.65% | 1.75% | 1.75% | 1.65% | 1.65% | 1.65% | 1.65% | 1.65% | 1.75% |
| Tropicamide | 0.0100% | 0.0250% | 0.0000% | 0.0000% | 0.0250% | 0.0250% | 0.0250% | 0.0150% | 0.0400% | 0.0250% | 0.0300% |
| Brimonidine | — | — | — | — | — | — | — | — | — | — | — |
| Mannitol | 2.5% | 2.5% | 2.5% | 2.5% | 2.5% | 2.5% | 2.5% | 2.5% | 2.5% | 2.5% | 2.5% |
| Polysorbate 80 | 2.00% | 2.50% | 2.00% | 1.00% | 0.10% | 2.00% | 2.50% | 2.50% | 3.50% | 2.50% | 3.50% |

TABLE 8-continued

Compositions containing little or no cycloplegic agent

| | | | | | | | | | | | |
|---|---|---|---|---|---|---|---|---|---|---|---|
| Polyoxyl 40 Stearate | — | — | — | — | — | — | — | — | — | — | — |
| Citrate | — | 0.10% | — | — | — | — | — | — | — | — | — |
| Glycerine | 0.10% | 0.10% | 0.10% | 0.10% | 0.10% | 0.10% | 0.10% | 0.10% | 0.10% | 0.10% | 0.10% |
| CMC | 0.75% | 0.85% | 0.85% | 0.85% | 0.85% | 0.85% | 0.85% | 0.75% | 0.60% | 1.60% | 0.60% |
| HPMC | — | — | — | — | — | — | — | — | — | — | — |
| Carbopol ® 940 | — | — | — | — | — | — | — | 0.75% | 0.60% | — | 0.60% |
| NaCl | 0.50% | 0.50% | — | — | — | — | — | — | — | — | — |
| Boric Acid | — | — | — | — | — | — | — | — | — | — | — |
| Postassium Borate | — | — | — | — | — | — | — | — | — | — | — |
| Phosphate buffer | 3 | 3 | 3 | 3 | 3 | 3 | 3 | 3 | 3 | 3 | 3 |
| Acetate | — | — | — | — | — | — | — | — | — | — | — |
| pH | 5.0 | 5.0 | 5.0 | 5.3 | 5.3 | 5.3 | 5.00 | 5.00 | 5.00 | 5.00 | 5.00 |
| BAK | 0.015% | 0.015% | 0.015% | 0.015% | 0.015% | 0.015% | 0.015% | 0.015% | 0.015% | 0.015% | 0.015% |
| Pupil Size (mm) | | | | | | | | | | | |
| Reading vs. Baseline 40 cm | 2.5 | 3 | 3 | 2 | 1.5 | 2.5 | 3 | 2 | 1.5 | 2.5 | 2.5 |
| Duration (hours) | 6 | 5 | 6 | 4 | 4 | 6 | 5.5 | 7 | 3 | 7 | 7 |
| Ciliary Spasms | 0.5 | 0.5 | 2 | 2 | 0 | 0 | 0 | 0.5 | 0 | 0.5 | 0.5 |
| Stinging | 1 | 0.5 | 1 | 0.5 | 0.5 | 0.5 | 0.5 | 0.5 | 0.25 | 0.25 | 0.25 |
| Blur (min) | | | | | | | | | 1.5 | 1 | 2 |
| Distance blur | none | none | none | none | none | none | none | none | none | none | none |
| Onset (min) | 20-25 | 20-25 | 20-25 | 20-25 | 20-25 | 20-25 | 20-25 | 20-25 | 20-25 | 20-25 | 20-25 |
| Redness 1hr (0-4) | 0.5 | 0.5 | 0.5 | 0.5 | 1.0 | 0.5 | 0.5 | 0.5 | | 0.5 | 0.5 |
| Redness 4hr (0-4) | | | | | | | | | | | |
| Overall comfort | poor | poor | poor | poor | good | good | good | good | good | good | good |
| Osmolarity | hi | hi | nl | nl | nl | nl | nl | nl | nl | nl | nl |
| Efficacy index: read*dur | 15 | 15 | 18 | 8 | 6 | 15 | 17 | 14 | 5 | 18 | 18 |
| OVERALL (1-5) | ** | | | | | | | | | **** | **** |

| | #L63 | #L64 | #L65 | #L66 | #L67 | #L68 | #L69 | #L70 | #L71 | #L72 | #L73 |
|---|---|---|---|---|---|---|---|---|---|---|---|
| Aceclidine | 1.65% | 1.75% | 1.65% | 1.75% | 1.75% | 1.75% | 1.75% | 1.75% | 1.75% | 1.75% | 1.75% |
| Tropicamide | 0.0250% | 0.0250% | 0.0250% | 0.0275% | 0.0275% | 0.0275% | 0.0250% | 0.0180% | 0.0160% | 0.0160% | 0.0150% |
| Brimonidine | — | — | — | — | — | — | — | — | — | — | — |
| Mannitol | 2.5% | 2.5% | 2.5% | 2.5% | 2.5% | 2.5% | 2.5% | 2.5% | 2.5% | 2.5% | 2.5% |
| Polysorbate 80 | 2.50% | 3.50% | 4.00% | 5.00% | 5.00% | 2.00% | 2.00% | 2.00% | 2.25% | 4.00% | 4.00% |
| Polyoxyl 40 Stearate | — | — | — | — | — | — | — | — | — | — | — |
| Citrate | — | — | — | — | — | — | — | — | — | — | — |
| Glycerine | 0.10% | 0.10% | 0.10% | — | — | — | — | — | — | — | — |
| CMC | 0.75% | 0.50% | 0.75% | — | 1.35% | | 1.35% | 1.45% | 1.45% | 1.45% | 1.45% |
| HPMC | — | — | — | — | — | — | — | — | — | — | — |
| Carbopol ® 940 | — | 0.50% | — | 1.35% | — | 1.45% | — | — | — | — | — |
| NaCl | — | — | — | — | — | — | — | — | — | — | — |
| Boric Acid | — | — | — | — | — | — | — | — | — | — | — |
| Postassium Borate | — | — | — | — | — | — | — | — | — | — | — |
| Phosphate buffer | 3 | 3 | 3 | 3 | 3 | 3 | 3 | 3 | 3 | 3 | 3 |
| Acetate | — | — | — | — | — | — | — | — | — | — | — |
| pH | 5.00 | 5.00 | 5.00 | 5.0 | 5.0 | 5.0 | 5.0 | 5.0 | 5.0 | 5.0 | 5.0 |
| BAK | 0.015% | 0.015% | 0.015% | 0.015% | 0.015% | 0.015% | 0.015% | 0.015% | 0.01% | 0.01% | 0.01% |
| Pupil Size (mm) | | | | | | | | | | | |
| Reading vs. Baseline 40 cm | 2 | 2.5 | 2 | 2.75 | 2.75 | 2.75 | 2.75 | 2.75 | 2.75 | 2.75 | 3 |
| Duration (hours) | 4 | | 5 | 7 | 7 | 5.5 | 6 | 7 | 7 | 7 | 7.5 |
| Ciliary Spasms | 0.5 | 0.5 | 0.5 | 0.5 | 0.5 | 0.5 | 0.5 | 0.5 | 0.5 | 0.5 | 0.5 |

TABLE 8-continued

Compositions containing little or no cycloplegic agent

| | | | | | | | | | | | |
|---|---|---|---|---|---|---|---|---|---|---|---|
| Stinging Blur (min) | 0.5 | 0.5 | 0.5 | 0.5 | 0.5 | 0.5 | | | | 1 | |
| Distance blur | none | none | none | none | none | none | none | none | none | none | none |
| Onset (min) | 20-25 | 20-25 | 20-25 | 20-25 | 20-25 | 20-25 | 20-25 | 20-25 | 20-25 | 20-25 | 20-25 |
| Redness 1hr (0-4) | 0.5 | 0.5 | 0.5 | 0.5 | 0.5 | 0.5 | | | | | |
| Redness 4hr (0-4) | | | | | | | | | | | |
| Overall comfort | good | good | good | good | good | good | good | good | good | good | good |
| Osmolarity | nl | nl | nl | nl | nl | nl | nl | nl | nl | nl | nl |
| Efficacy index: read*dur | 8 | 0 | 10 | 19 | 19 | 15 | 17 | 19 | 19 | 19 | 23 |
| OVERALL (1-5) | poor | | ? | **½ | ** | | | | | **** | **** ½ |

| | #L74 | #L75 | #L76 | #L77 | #L78 | #L79 | #L80 | #L81 | #L82 | #L83 | #L84 |
|---|---|---|---|---|---|---|---|---|---|---|---|
| Aceclidine | 1.75% | 1.75% | 1.75% | 1.75% | 1.75% | 1.75% | 1.75% | 1.75% | 1.75% | 1.65% | 1.40% |
| Tropicamide | 0.0150% | 0.0150% | 0.0120% | 0.0110% | 0.0100% | 0.0000% | — | 0.0100% | 0.0150% | 0.0000% | 0.0000% |
| Brimonidine | — | — | — | — | — | 0.015% | — | — | — | — | — |
| Mannitol | 2.5% | 2.5% | 2.5% | 2.5% | 2.5% | 2.5% | 2.5% | 2.5% | 2.5% | 2.5% | 2.5% |
| Polysorbate 80 | 5.00% | 5.00% | 5.00% | 5.00% | 5.00% | 5.00% | — | 6.00% | 7.00% | 0.00% | 0.00% |
| Polyoxyl 40 Stearate | — | — | — | — | — | — | — | — | — | — | 5.5% |
| Citrate | — | — | — | — | — | — | — | — | — | — | — |
| Glycerine | — | — | — | — | — | — | — | — | — | — | — |
| CMC | 1.45% | 1.43% | 1.43% | 1.40% | 1.40% | 1.40% | 1.40% | 1.40% | 1.40% | 0.00% | 0.75% |
| HPMC | | | | | | | | | | | |
| Carbopol ® 940 | — | — | — | — | — | — | — | — | — | — | — |
| NaCl | — | — | — | — | — | — | — | — | 0.50% | — | — |
| Boric Acid | — | — | — | — | — | — | — | — | — | — | — |
| Postassium Borate | — | — | — | — | — | — | — | — | — | — | — |
| Phosphate buffer | 3 | 3 | 3 | 3 | 3 | 3 | 3 | 3 | 3 | 3 | 3 |
| Acetate | — | — | — | — | — | — | — | — | — | — | — |
| pH | 5.0 | 5.0 | 5.0 | 5.0 | 5.0 | 5.0 | | 5.0 | 5.0 | 5.0 | 5.0 |
| BAK | 0.01% | 0.01% | 0.01% | 0.01% | 0.01% | 0.01% | — | 0.01% | 0.01% | 0.010% | 0.010% |
| Pupil Size (mm) | | | | | | | | | | | |
| Reading vs. Baseline 40 cm | 3.25 | 3.25 | 3.5 | 3.5 | 3.75 | 2.5 | 2.5 | 2.75 | 2.5 | 1 | 1.5 |
| Duration (hours) | 7.5 | 7.5 | 7 | 8 | 9 | 8 | 7 | 5.5 | 5 | 3 | 3.5 |
| Ciliary Spasms | 0.5 | 0.5 | 1 | 1 | 1 | 2 | 2 | 0.5 | 0.5 | 1 | 1 |
| Stinging | | | | | | | | | | | 1.0 |
| Blur (min) | 1.5 | 1.5 | 1.5 | | | | | | | | |
| Distance blur | none | none | none | none | none | none | none | none | none | none | none |
| Onset (min) | 20-25 | 20-25 | 20-25 | 20-25 | 20-25 | 20-25 | 20-25 | 20-25 | 20-25 | 20-25 | 20-25 |
| Redness 1hr (0-4) | | | | | | | | | | | 2.0 |
| Redness 4hr (0-4) | | | | | | | | | | | |
| Overall comfort | good-exc | good-exc | good-exc | exc | exc | fair | fair | good | good | | fair |
| Osmolarity | nl | nl | nl | nl | nl | nl | nl | nl | hi | nl | nl |
| Efficacy index: read*dur | 24 | 24 | 25 | 28 | 34 | 20 | 18 | 15 | 13 | 3 | 5 |
| OVERALL (1-5) | ***** | ***** | *****! | *****!! | *****!! | **** | **** | *** | *** | | * |

| | #L85 | #L86 | #L87 | #L88 | #L89 | #L90 | #L91 | #L92 | #L93 | #L94 |
|---|---|---|---|---|---|---|---|---|---|---|
| Aceclidine | 1.75% | 1.75% | 1.75% | 1.75% | 1.75% | 1.75% | 1.75% | 1.75% | 1.75% | 1.75% |
| Tropicamide | 0.0000% | 0.0100% | 0.0900% | 0.0060% | 0.0060% | 0.0100% | 0.0060% | 0.0060% | 0.0060% | 0.0060% |
| Brimonidine | — | — | — | — | — | — | — | — | — | — |
| Mannitol | 2.5% | 2.5% | 2.5% | 2.5% | 2.5% | 2.5% | 2.5% | 2.5% | — | 2.5% |
| Polysorbate 80 | 5.00% | 2.5% | 2.5% | 2.5% | 2.5% | 2.50% | 2.50% | 2.75% | 2.75% | 3.50% |

TABLE 8-continued

Compositions containing little or no cycloplegic agent

| | | | | | | | | | | |
|---|---|---|---|---|---|---|---|---|---|---|
| Polyoxyl 40 Stearate | — | — | — | — | — | — | — | — | — | — |
| Citrate | — | — | — | — | — | — | — | — | — | — |
| Glycerine | — | — | — | — | — | — | — | — | — | — |
| CMC | 1.40% | — | — | — | — | — | — | — | — | — |
| HPMC | — | 1.75% | 1.75% | 1.75% | 1.75% | — | — | — | — | — |
| Carbopol ® 940 | — | — | — | — | — | 1.75% | 1.75% | 1.80% | 1.80% | 1.80% |
| NaCl | 0.00% | 0.50% | — | 0.50% | — | 0.50% | 0.50% | 0.50% | 0.50% | 0.50% |
| Boric Acid | — | — | 0.35% | — | — | — | — | — | 0.25% | — |
| Postassium Borate | — | — | 0.47% | — | — | — | — | — | 0.37% | — |
| Phosphate buffer | 3 | 3 | 3 | 3 | 4 | 3 | 3 | 3 | 3 | 3 |
| Acetate | — | — | — | — | — | — | — | — | — | — |
| pH | 5.0 | 5.0 | 5.0 | 5.0 | 6.0 | 5.0 | 5.0 | 5.0 | 5.0 | 5.0 |
| BAK | 0.010% | 0.020% | 0.020% | 0.020% | 0.020% | 0.02% | 0.02% | 0.02% | 0.02% | 0.02% |
| Pupil Size (mm) | | | | | | | | | | |
| Reading vs. Baseline 40 cm | 3.5 | 3.5 | 3.5 | 3.75 | 3.75 | 3.5 | 3.75 | 3.75 | 3.75 | 3.75 |
| Duration (hours) | 7 | 8 | 7 | 9 | 9 | 7 | 7 | 8 | 8 | 8.5 |
| Ciliary Spasms | 2 | 0.5 | 0.5 | 0.5 | 0.5 | 0.5 | 0.5 | 0 | 0 | 0 |
| Stinging | 0.5 | | | | | | | | | |
| Blur (min) | | | | | | | | | | |
| Distance blur | 2.0 | none | none | none | none | none | none | none | none | none |
| Onset (min) | 20-25 | 20-25 | 20-25 | 20-25 | 20-25 | 20-25 | 20-25 | 20-25 | 20-25 | 20-25 |
| Redness 1hr (0-4) | 1.0 | 1.0 | 0.5 | 0.5 | 0.5 | 0.5 | 0.5 | 0.5 | 0.5 | 0.5 |
| Redness 4hr (0-4) | | | | | | | | | | |
| Overall comfort | good | good | good | good | good | | | | | |
| Osmolarity | nl | nl | nl | nl | lo | | | | | |
| Efficacy index: read*dur | 25 | 28 | 25 | 34 | 34 | 25 | 26 | 30 | 30 | 32 |
| OVERALL (1-5) | **** | | | | | ***** | ***** | ***** | ****** | ***** |

All concentration in weight by volume.
mm denotes millimeters.
cm denotes centimeters.
min denotes minutes.
%* denotes amount can optionally vary from about 0.01% to about 1% w/v.
# denotes formulation can include polysorbate 80 or not include polysorbate 80.
Ciliary spasms scores correspond to the following: 0 = no discomfort; 0.5 = slight sting; 1 = noticeable squeeze/discomfort; 2 = pain for less than 30 minutes; 3 = pain for 1 hour or more; and 4 = severe to intolerable pain.

Figure 3:
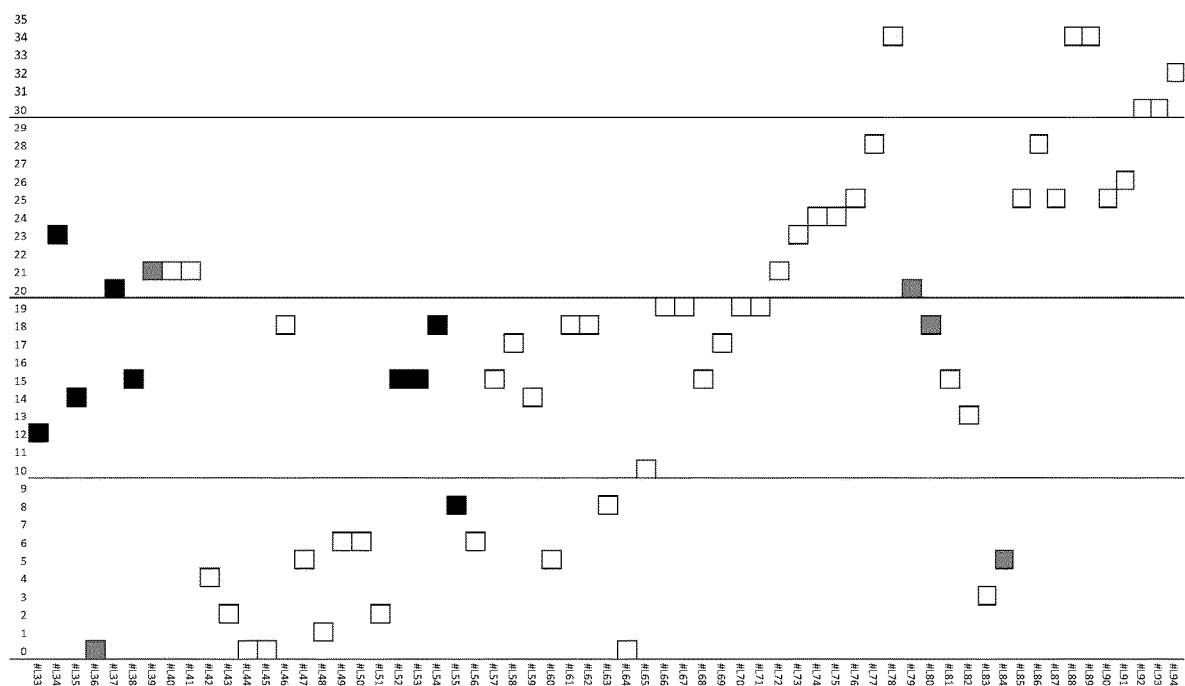
FIG. 3 is a graphical representation of the Efficacy Index for formulas #L33-#L94. Box color denotes a comfort level of good for white, fair for cross-hatched and poor for black.

The efficacy index is demonstrated in FIG. 3. In brief, the score is calculated by multiplying the lines of improvement in near visual acuity by the number of hours the improvement lasts. For example a score of: 5 is equal to +1 lines of improvement in near visual acuity for 5 hours; 10 is equal to +1.5 lines of improvement for 6.7 hours; 15 is equal to 2 lines of improvement for 7.5 hours; 20 is equal to 2.5 lines of improvement for 8 hours; 25 is equal to 3+ lines of improvement for 8.3 hours and 35 is equal to 3.75+ lines of improvement for 9 hours.

As demonstrated by comparing the Reading vs. Baseline at 40 cm and Efficacy Indexes of formulas #L33-#L37, formulas containing 1.40% or more aceclidine are better at correcting presbyopia than those formulas containing 1.25% aceclidine. Inversely, the lower concentration of aceclidine results in better overall comfort to the user. The addition of 2.5% mannitol to formulas with 1.45% aceclidine improves overall comfort but at the expense of reducing the presbyopic correcting effect (compare #L37 with #L47.) This reduction in near vision improvement is exacerbated with the addition of 4.0% mannitol (compare #L47 with #L48.) Increasing aceclidine concentrations to 1.65% or 1.75% overcome the reduction in near vision improvement seen with the addition of mannitol (compare #L47 with #L49 and #L50.)

Further, formulas containing 1.75% aceclidine and 2.5% mannitol have an increased efficacy and duration in treating presbyopia that is correlated with an increase in polysorbate 80 up to 5.0% and then inversely correlated with a decrease in CMC from 1.45% to 1.40% (compare formulas #L66 to #L78.) Optimal formulations are demonstrated by #L77, #L78 and #L85-#L94, which each have the highest improve reading at 40 cm at between 3.5 and 3.75 visual acuity lines and the highest Efficacy Index scores of 25 to 34, and the longest duration from 7 to 9 hours. The increase in effectiveness and duration of formulas from #L66 to #L78 are also inversely correlated with a decrease in tropicamide from 0.0275% to 0.01%. This same trend is demonstrated by the increase in effectiveness (i.e. Reading vs. Baseline 40 cm) when comparing #L85 through #L94.

This data demonstrates that mannitol can effectively reduce ciliary spasms caused by aceclidine, thus reducing the need for a cycloplegic agent such as tropicamide. Further, this data demonstrates that the addition of a non-ionic surfactant and viscosity agent can further enhance the efficacy and duration of compositions containing aceclidine, mannitol and low tropicamide. This data also demonstrates that the use of a cycloplegic agent in aceclidine compositions containing polysorbate 80 and CMC is most beneficial to presbyopic correction when the cycloplegic agent is closer to 0.006% than 0.025%. Finally, this data demonstrates that compositions comprising aceclidine and mannitol are sufficient to correct presbyopia with tolerable pain.

Example 12 Use of Further High Tropicamide Formulations

The following examples are of aceclidine formulations containing more than 0.0300 tropicamide.

TABLE 9

High tropicamide formulations

|  | #L39 | #L40 | #L41 | #L42 | #L43 | #L44 | #L45 | #L46 |
|---|---|---|---|---|---|---|---|---|
| Aceclidine | 1.45% | 1.45% | 1.40% | 1.40% | 1.40% | 1.40% | 1.40% | 1.40% |
| Tropicamide | 0.035% | 0.037% | 0.040% | 0.050% | 0.055% | 0.06% | 0.08% | 0.04% |
| Polyoxyl 40 Stearate | 5.5% | 5.5% | 5.5% | 5.5% | 5.5% | 5.5% | 5.5% | 5.5% |
| Citrate | 0.10% | 0.10% | 0.10% | 0.10% | 0.10% | 0.10% | 0.10% | 0.10% |
| Glycerine | 0.10% | 0.10% | 0.10% | 0.10% | 0.10% | 0.10% | 0.10% | 0.10% |
| CMC | 0.75% | 0.75% | 0.75% | 0.75% | 0.75% | 0.75% | 0.75% | 0.75% |
| NaCl | 0.50% | 0.50% | 0.50% | 0.50% | 0.50% | 0.50% | 0.50% | 0.50% |
| Phosphate buffer | 3 | 3 | 3 | 3 | 3 | 3 | 3 | 3 |
| pH | 5.0 | 5.0 | 5.0 | 5.25 | 5.5 | 5.25 | 5.0 | 5.0 |
| BAK | 0.015% | 0.015% | 0.015% | 0.015% | 0.015% | 0.015% | 0.015% | 0.015% |
| Reading vs. Baseline 40 cm | 3.5 | 3.5 | 3.5 | 2 | 1 | 1 | 1 | 3 |
| Duration (hours) | 6 | 6 | 6 | 2 | 2 | 1 | 1 | 6 |
| Ciliary Spasm | 1 | 0.5 | 0.5 | 0.5 | 0.5 | 0.5 | 0.5 | 0.5 |
| Stinging | 1.0 | 1.0 | 1.0 | 0.5 | 0.25 | 0.5 | 1 | 1 |
| Distance blur | none | none | none | none | none | none | none | none |
| Onset (min) | 20-17 | 20-18 | 20-19 | 20-20 | 20-21 | 20-22 | 20-23 | 20-24 |
| Redness 1hr (0-4) | 0.5 | 0.5 | 0.5 | 0.5 | 0.5 | 0.5 | 0.5 | 0.5 |
| Overall comfort | fair | good | good | good | good | good | good | good |
| Osmolarity | hi | hi | hi | hi | hi | hi | hi | hi |
| Efficacy index: read* dur | 21 | 21 | 21 | 4 | 2 | 1 | 1 | 18 |
| OVERALL (1-5) | ** | *** | *** | * | ½* | ¼* | ¼* | * |

Ciliary spasms scores correspond to the following: 0=no discomfort; 0.5=slight sting; 1=noticeable squeeze/discomfort; 2=pain for less than 30 minutes; 3=pain for 1 hour or more; and 4=severe to intolerable pain.

As demonstrated by formulas #L39-#L41 and compared to formulas #L74-#L78 in Table 8, formulas containing about 1.40% to about 1.45% aceclidine, about 0.035% to about 0.04% tropicamide, about 5.5% polyoxyl 40 stearate and about 0.75% CMC are almost, but not quite as effective at treating presbyopia as formulas containing about 1.65% to about 1.75% aceclidine, about 2.5% mannitol, about 5% polysorbate 80, about 1.40% CMC formulas. This effectiveness decreases dramatically when tropicamide is increased to about 0.05% to about 0.08% tropicamide.

Example 13. Use of a Compound Containing Mannitol

Formulation:
 aceclidine 1.75% w/v
 tropicamide 0.006% w/v
 mannitol 2.5% w/v
 polysorbate 80 2.75% w/v
 NaCl 0.5% w/v
 hydroxypropylmethyl cellulose 0.5%-1.80% w/v
 phosphate buffer 3 mM
 pH 5.0, and
 BAK 0.020% as preservative.
Method:
 The subject instilled 2 drops of the above formulation in each eye and the excess wiped from lids and lashes.
Results:
 Within 20 minutes, near vision improvement of about 3 lines of visual acuity was noted with very slight dimming. Throughout the day near vision remained enhanced with no loss of distance vision. Further, if the subject previously suffered from any mild refractive errors distance vision was improved. Over a 5-8 hour period the pupil begins to slightly recover, and after a few hours the minimal dimming was no longer noted. Both excellent near vision near onset, and possibly still slightly improved near vision continued as the pupil slightly begins to increase from its minimal size earlier in the day.

Example 14. Use of a Preferred Embodiment Optimizing Tropicamide and Hydroxypropyl Methyl Cellulose

| Composition | |
|---|---|
| Aceclidine | 1.75% w/v |
| Tropicamide | 0.010% w/v |
| Mannitol | 2.50% w/v |
| Polysorbate 80 | 3.50% w/v |
| NaCl | 0.50% w/v |
| HPMC | 1.25% w/v |
| BAK | 0.02% w/v |
| Phosphate buffer | 3 mM |
| pH | 5.00 |
| Method | |

The subject instilled 2 drops of the above formulation in each eye as 1 single drop each eye and a second drop after 5 minutes.

Results:

Comfort, duration and efficacy were assessed. Stinging upon instillation and over the first hour was minimal with a score of 0.25 out of 4. Redness over the first hour was also are based on a scale of 0 to 4 with 0 being none and 4 being the most severe. Other than Brij® 35 stinging and redness were mild to nearly absent. Duration was excellent for each nonionic surfactant tested.

TABLE 10

Comparing efficacy and comfort of various nonionic surfactants

| % w/v | Polysorbate 80 | Polyoxyl 35 castor oil | Polyoxyl 40 stearate | Poloxamer 407 | Brij® 35 | Tyloxapol (prophetic) | Polysorbate 20 (prophetic) | Poloxamer 188 (prophetic) | Solulan C-24 (prophetic) |
|---|---|---|---|---|---|---|---|---|---|
| Aceclidine | 1.75% | 1.75% | 1.75% | 1.75% | 1.75% | 1.75% | 1.75% | 1.75% | 1.75% |
| Tropicamide | 0.006% | 0.006% | 0.005% | 0.005% | 0.005% | 0.006% | 0.006% | 0.006% | 0.006% |
| Mannitol | 2.5% | 2.5% | 2.5% | 2.5% | 2.5% | 2.5% | 2.5% | 2.5% | 2.5% |
| Nonionic surfactant | 3.5% | 3.5% | 3.5% | 3.5% | 3.5% | 3.5% | 3.5% | 3.5% | 3.5% |
| NaCl | 0.50% | 0.50% | 0.50% | 0.50% | 0.50% | 0.50% | 0.50% | 0.50% | 0.50% |
| HPMC | 1.80% | 1.80% | 1.80% | 1.80% | 1.80% | 1.80% | 1.80% | 1.80% | 1.80% |
| BAK | 0.02% | 0.02% | 0.02% | 0.02% | 0.02% | 0.02% | 0.02% | 0.02% | 0.02% |
| Phosphate buffer | 3 mM | 3 mM | 3 mM | 3 mM | 3 mM | 3 mM | 3 mM | 3 mM | 3 mM |
| pH | 5.00 | 5.00 | 5.00 | 5.00 | 5.00 | 5.00 | 5.00 | 5.00 | 5.00 |
| Stinging | 0.25 | 0 | 0.5 | 0.5 | 2 | 0-2 | 0-2 | 0-2 | 0-2 |
| Redness 1hr | 0.5 | 0.25 | 0.75 | 1 | 2.5 | 0.25-2.5 | 0.25-2.5 | 0.25-2.5 | 0.25-2.5 |
| Reading vs. Baseline (40 cm) | 3.75 | 3.5 | 3 | 3 | 2 | 2-3.5 | 2-3.5 | 2-3.5 | 2-3.5 |
| Duration (hours) | 10 | 9 | 7 | 7 | 4 | 4-8 | 4-8 | 4-8 | 4-8 |
| Efficacy Index read* dur | 37.5 | 31.5 | 21 | 21 | 8 | 8-37.5 | 8-37.5 | 8-37.5 | 8-37.5 |
| Onset (min) | 20-25 | 20-25 | 20-25 | 20-25 | 30-40 | 20-40 | 20-40 | 20-40 | 20-40 | minimal with a score of 0.5 out of 4 assessed at 20 minutes. Onset of vision improvement occurred with the first 20 to 25 minutes after instillation. Baseline near vision (i.e. 40 centimeters) was improved by 3.5 lines of visual acuity. Improvement in near vision lasted for 8.5 hours. Comparing this formula to those in Table 8, the Efficacy Index score was 29.75. Substituting HPMC 1.80% w/v with HPMC 1.65% w/v resulted in a slight reduction in near vision improvement to 3.25 lines of visual acuity and a slight reduction in duration to just over about 6 hour. Comparing this formula to those in Table 8, the Efficacy Index score was 19.5.

Example 15. Use of a Compound Containing Mannitol with Various Nonionic Surfactants Compositions Table 10 lists the active ingredients, excipients and their concentrations for compositions with both tested and prophetic examples of nonionic surfactants.

Methods

The subject independently instilled 2 drops of the above compositions in each eye and the excess wiped from lids and lashes.

Results

All nonionic surfactants tested demonstrate substantial near vision improvement. Of those tested only Brij® 35 was marginal due to the significant corneal irritation, hyperemia and reduced duration that resulted. Polysorbate 80 and poly 35 castor oil were most preferred, polyoxyl 40 stearate and poloxamer 407 excellent as well. However, polyoxyl 40 stearate caused a precipitate reaction with cellulose viscosity agents and added other stability issues.

Comfort and duration for each non-ionic surfactant were also tested and are noted in Table 10. Stinging and Redness Example 16. Us of a Compound Containing Optimizing Nonionic Surfactant and Antioxidant Additives and Concentrations

| | Compositions |
|---|---|
| Aceclidine | 1.75% w/v |
| Tropicamide | 0.010% w/v |
| Mannitol | 2.50% w/v |
| Polysorbate 80 | 4.00% w/v |
| NaCl | 0.00% w/v |
| HPMC | 1.25% w/v |
| | (high MW equaling viscosity of about 400 cps units) |
| BAK | 0.02% w/v |
| Sorbate | 0.12% w/v |
| BAK | 0.02% w/v |
| EDTA | 0.01% |
| Citrate buffer | 3 mM |
| pH | 5.00 |
| Method | |

2 subjects instilled 2 drops each of the above formulation in each eye about 5 minutes apart.

Results:

Comfort, duration and efficacy were assessed. Stinging upon instillation and over the first hour was minimal for each subject with a score of 0.50 out of 4 for about 15 seconds. Redness over the first hour was also minimal for each subject with a score of 0.25 out of 4 assessed at 20 minutes. Onset of vision improvement occurred with the first 20 to 25 minutes after instillation. For subject 1 baseline near vision (i.e. 40 centimeters) was improved by 4.0-4.25 lines of visual acuity and lasted for 11.5 hours. For subject 2 baseline near vision was improved by 3.5 lines of visual acuity and lasted for 9.5 hours. The Efficacy Index score was 47.38 and 33.25, among the highest achieved for any formulation.

Example 17. Aceclidine Compositions for Cold Chain Storage (Prophetic)

TABLE 11

Cold Chain Storage Compositions

| Composition | CS#1 | CS#2 | CS#3 | CS#4 | CS#5 | CS#6 | CS#7 | CS#8 |
|---|---|---|---|---|---|---|---|---|
| Aceclidine | 1.75% | 1.75% | 2.50% | 4.00% | 2.00% | 1.65% | 1.75% | 1.75% |
| Mannitol | 2.50% | 2.50% | 2.50% | 2.50% | 2.50% | — | 2.50% | 2.50% |
| Polysorbate 80 | 4.00% | 4.00% | 4.00% | 4.00% | 4.00% | — | 4.00% | 4.00% |
| HPMC | 1.25% | 1.25% | 1.25% | 1.25% | 1.25% | 0.75% | 1.10% | 1.10% |
| Sodium Citrate | 0.10% | 0.10% | 0.10% | 0.10% | 0.10% | — | 0.10% | 0.10% |
| BAK | 0.02% | 0.02% | 0.02% | 0.02% | — | — | 0.02% | 0.02% |
| Sorbic Acid | 0.12% | 0.12% | 0.10% | 0.12% | 0.12% | 0.12% | 0.12% | 0.12% |
| Disodium Edetate Dihydrate | 0.10% | 0.10% | 0.10% | 0.10% | — | — | 0.10% | 0.10% |
| Sodium Ascorbate | — | — | 0.10% | — | — | — | — | — |
| Sodium bisulfate | — | — | — | 0.10% | — | — | — | — |
| Sodium metabisulfite | — | — | — | — | 0.10% | — | — | — |
| pH | 5.0 | 6.0 | 6.0 | 6.5 | 6.5 | 7.0 | 5.0 | 6.0 |
| N2 fill/purge | Yes | Yes | Yes | Yes | Yes | No | No | No |

| Composition | CS#9 | CS#10 | CS#11 | CS#12 | CS#13 | CS#14 | CS#15 | CS#16 |
|---|---|---|---|---|---|---|---|---|
| Aceclidine | 4.00% | 0.50% | 2.50% | 3.00% | 4.00% | 4.00% | 4.00% | 4.00% |
| Mannitol | — | — | — | — | — | — | — | — |
| Polysorbate 80 | — | — | — | — | — | — | — | — |
| HPMC | — | — | — | 0.75% | 1.25% | 1.25% | 1.25% | 1.25% |
| Sodium Citrate | — | — | — | — | — | 0.10% | — | — |
| BAK | — | — | — | — | — | — | — | — |
| Sorbic Acid | — | — | — | — | — | — | — | — |
| Disodium Edetate Dihydrate | — | — | — | — | — | — | — | — |
| Sodium Ascorbate | — | — | — | — | — | — | — | — |
| Sodium bisulfate | — | — | — | — | — | — | 0.10% | — |
| Sodium metabisulfite | — | — | — | — | — | — | — | 0.10% |
| pH | 5.0 | 7.0 | 6.0 | 6.0 | 6.0 | 6.0 | 6.0 | 6.0 |
| N2 fill/purge | No | No | Yes | Yes | Yes | Yes | Yes | Yes |

| Composition | CS#17 | CS#18 | CS#19 | CS#20 |
|---|---|---|---|---|
| Aceclidine | 4.00% | 4.00% | 4.00% | 4.00% |
| Mannitol | 2.50% | 2.50% | 2.50% | 2.50% |
| Polysorbate 80 | 4.00% | 4.00% | 4.00% | 4.00% |
| HPMC | 1.25% | 1.25% | 1.25% | 1.25% |
| Sodium Citrate | 0.10% | — | — | 0.25% |
| BAK | 0.02% | 0.02% | 0.02% | 0.02% |
| Sorbic Acid | 0.12% | 0.12% | 0.12% | 0.12% |
| Disodium Edetate Dihydrate | — | — | — | — |
| Sodium Ascorbate | — | — | — | — |
| Sodium bisulfate | — | 0.10% | — | — |
| Sodium metabisulfite | — | — | 0.10% | — |
| pH | 6.0 | 6.0 | 6.0 | 6.0 |
| N2 fill/purge | Yes | Yes | Yes | Yes |

Methods

Aceclidine cold chain storage compositions CS #1-5 and 11-20 were filled into vials each under a nitrogen overlay followed by a nitrogen purge of remaining headspace. CS #6-10 were filled into vials each under ambient air and headspace. 1 vial of each composition was stored at 25 degrees Celsius and the other was stored at 5 degrees Celsius.

Results

TABLE 12

Aceclidine Cold Chain Storage Composition Stability

| Composition | CS#9 | CS#10 | CS#11 | CS#12 | CS#13 | CS#14 |
|---|---|---|---|---|---|---|
| 25 Celsius 90% Stability (weeks) | 4 | 5 | — | — | — | — |
| 5 Celsius 90% Stability (months) | 7 | 8 | 12 | 12.5 | 15 | 18 |

| Composition | CS#15 | CS#16 | CS#17 | CS#18 | CS#19 | CS#20 |
|---|---|---|---|---|---|---|
| 25 Celsius 90% Stability (weeks) | — | — | — | — | — | — |
| 5 Celsius 90% Stability (months) | 18 | 18 | 20 | 20 | 20 | 22 |

Figure 4:
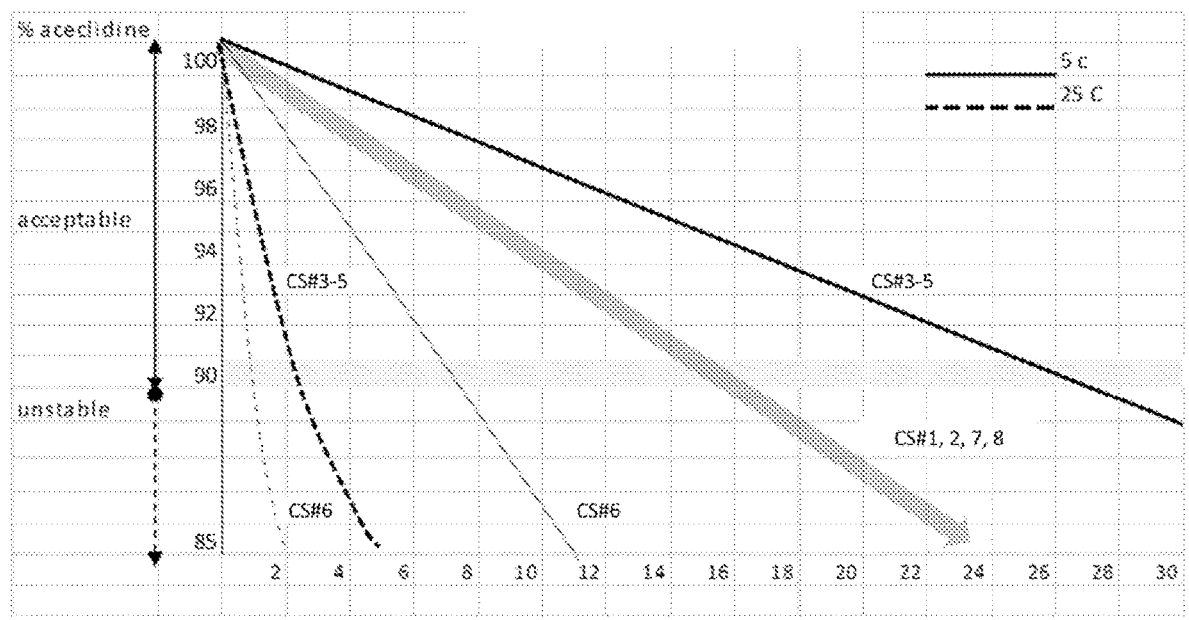
FIG. 4 is a graphical representation of percent stability of aceclidine cold storage compositions at 5 and 25 degrees Celsius over 30 months.

As seen in FIG. 4, CS #3-5 containing 0.10% sodium ascorbate, 0.10% sodium bisulfate or 0.10% sodium metabisulfite were stable for about 2 months at 25 degrees Celsius and for about 26 months at 5 degrees Celsius.

As seen in Table 12, filling vials under a nitrogen overlay and nitrogen purge of the headspace resulted in a cold storage stability increase of 4-5 months. The addition of HPMC further increased stability another 3 months; sodium citrate, sodium bisulfate or sodium metabisulfite another 3 months; and the further addition of sorbic acid and BAK another 2 months further increased the length of stability. CS #20 increased stability up to 22 months.

Example 18. Stability in Mylar® Lined Pouches

Aceclidine formulations of the present invention were placed in containers that were subsequently placed in biaxially-oriented polyethylene terephthalate lined pouches at −20, 5 and 25 C for up to 3 months. Aceclidine total related substances was recorded at 1, 2, 3 and 6 months. Results of this study can be seen in Table 13, below.

Mylar® was used as the source of biaxially-oriented polyethylene terephthalate. Mylar is a registered trademark of and available from DuPont Teijin Films US Limited.

TABLE 13

Aceclidine Total Related Substances after Storage

| Conditions | Initial Result | One Month Result | Two Month Result | Three Month Result | Six Month Result | Total % Change |
|---|---|---|---|---|---|---|
| Unpouched (5 C.) | 0.41% | 0.55% | 0.51% | 0.05% | 0.49% | 0.08% |
| Unpouched (25 C.) | | 0.58% | 1.45% | 1.39% | 4.87% | 4.46% |
| Pouched (5 C.) | | 0.54% | | 0.35% | 0.47% | 0.06% |
| Pouched (25 C.) | | 0.55% | | 1.26% | 0.36% | −0.05% |
| Pouched (−20 C.) | | 0.74% | | 0.25% | 0.00% | −0.41% |
| Pouched (5 C.) | | 0.50% | | 0.18% | 0.00% | −0.41% |
| Pouched (25 C.) | | 0.74% | | 0.31% | 0.00% | −0.41% |

As seen in Table 13, the use of a Mylar® lined pouches helped maintain aceclidine potency by reducing degradation rate. Specifically, compare Unpouched at room temperature (25 C) total % change of 4.46% to the −0.05% and 0.041% total % change of Pouched at room temperature (25 C).

Example 19. Aceclidine Potency Following Storage

Aceclidine formulations of the present invention were placed in containers that were subsequently placed in biaxially-oriented polyethylene terephthalate lined pouches at −20, 5 and 25 C for up to 3 months. Aceclidine potency was recorded at 1, 2, 3 and 6 months. Results of this study can be seen in Table 14, below.

TABLE 14

Aceclidine Potency after Storage

| Sample | Initial Result | One Month Result | Two Month Result | Three Month Result | Six Month Result | Percent Change Between Initial and Six Month Results |
|---|---|---|---|---|---|---|
| Unpouched (5 C.) | 99.70% | 99.3% | 102.0% | 100.0% | 100.5% | 0.8% |
| Unpouched (25 C.) | | 98.2% | 101.9% | 98.2% | 97.7% | −2.0% |
| Pouched (5 C.) | | 100.0% | | 99.7% | 100.8% | 1.1% |
| Pouched (25 C.) | | 98.4% | | 97.5% | 94.9% | −4.8% |
| Pouched (−25 C.) | 99.60% | 98.5% | | 101.4% | 103.1% | 3.5% |
| Pouched (5 C.) | | 99.5% | | 102.3% | 102.2% | 2.6% |
| Pouched (25 C.) | | 103.0% | | 99.0% | 96.0% | 3.6% |

As seen in Table 14, the use of 5 degrees Celsius storage helped maintain aceclidine potency. Specifically, compare Unpouched at room temperature (25 C) total % change of −2.0% potency to the 0.8% change of Unpouched in cold storage (5 C) for the initial result of 99.70% and compare Unpouched at room temperature (25 C) total % change of 3.6% potency to the 2.6% change of Unpouched in cold storage (5 C) for the initial result of 99.60%.

What is claimed is:

1. A method for treating presbyopia in a subject in need thereof, the method comprising:
    (a) providing an aqueous ophthalmological solution comprising aceclidine, wherein the aqueous ophthalmological solution does not comprise a cycloplegic agent;
    (b) storing the aqueous ophthalmological solution in a container having a headspace at a temperature from about 2 degrees Celsius to about 8 degrees Celsius for at least 7 months to provide a stored aqueous ophthalmological solution; and
    (c) administering the stored aqueous ophthalmological solution to the subject in need thereof, wherein upon administration, the stored aqueous ophthalmological solution comprises at least 90% of the aceclidine that the aqueous ophthalmological solution comprised at the onset of the storing;
    thereby treating the presbyopia in the subject.

2. The method of claim 1, wherein the aqueous ophthalmological solution is stored for at least 12 months.

3. The method of claim 2, wherein the aqueous ophthalmological solution is stored for at least 18 months.

4. The method of claim 3, wherein the aqueous ophthalmological solution is stored for at least 24 months.

5. The method of claim 1, wherein the aqueous ophthalmological solution has a viscosity of about 1 centipoise (cp) to about 25 cps at a high shear of blinking and a viscosity of about 50 cps to about 200 cps at a low shear between blinks.

6. The method of claim 1, wherein the aqueous ophthalmological solution comprises a pH from about 4.0 to about 8.0.

7. The method of claim 1, wherein the aceclidine is at a concentration from about 0.25% to about 4.0% w/v aceclidine, wherein w/v denotes weight by total volume of the aqueous ophthalmological solution.

8. The method of claim 7, wherein the aceclidine is at a concentration from about 0.50% to about 1.90% w/v aceclidine, wherein w/v denotes weight by total volume of the aqueous ophthalmological solution.

9. The method of claim 8, wherein the aceclidine is at a concentration from about 1.65% to about 1.85% w/v aceclidine, wherein w/v denotes weight by total volume of the aqueous ophthalmological solution.

10. The method of claim 1, wherein the aqueous ophthalmological solution further comprises a surfactant.

11. The method of claim 1, wherein the aqueous ophthalmological solution further comprises a viscosity enhancer.

12. The method of claim 11, wherein the aceclidine remains in the aqueous ophthalmological solution for at least 7 additional months in comparison to an aqueous ophthalmological solution not comprising the viscosity enhancer.

13. The method of claim 1, wherein the aqueous ophthalmological solution is stored for 7 months to 18 months.

14. The method of claim 1, wherein the aqueous ophthalmological solution is stored for 7 months.

15. The method of claim 1, wherein the aqueous ophthalmological solution is stored for about 12 months.

16. The method of claim 1, wherein the aqueous ophthalmological solution is stored for about 15 months.

17. The method of claim 1 wherein the aqueous ophthalmological solution further comprises a cryoprotectant.

18. The method of claim 1, wherein the aqueous ophthalmological solution further comprises a polyol.

19. The method of claim 1, wherein the aqueous ophthalmological solution further comprises mannitol.

20. The method of claim 1, wherein a cycloplegic agent is not administered to the subject.

* * * * *